US012747416B2

(12) United States Patent
Weide et al.

(10) Patent No.: US 12,747,416 B2
(45) **Date of Patent: *Sep. 29, 2026**

(54) CLEANING COMPOSITIONS COMPRISING DISPERSINS VI

(71) Applicant: Henkel AG & Co. KGaA, Duesseldorf (DE)

(72) Inventors: Mirko Weide, Duesseldorf (DE); Susanne Wieland, Zons/Dormagen (DE); Rune Nygaard Monrad, Bagsvaerd (DK); Jesper Salomon, Bagsvaerd (DK); Dorotea Raventos Segura, Bagsvaerd (DK); Rebecca Vejborg, Bagsvaerd (DK)

(73) Assignees: Henkel AG & Co. KGaA, Duesseldorf (DE); Novozymes A/S, Bagsvaerd (DK)

( * ) Notice: Subject to any disclaimer, the term of this patent is extended or adjusted under 35 U.S.C. 154(b) by 1072 days.

This patent is subject to a terminal disclaimer.

(21) Appl. No.: 17/786,562

(22) PCT Filed: Dec. 7, 2020

(86) PCT No.: PCT/EP2020/084947
§ 371 (c)(1),
(2) Date: Jun. 17, 2022

(87) PCT Pub. No.: WO2021/122118
PCT Pub. Date: Jun. 24, 2021

(65) Prior Publication Data

US 2023/0048546 A1 Feb. 16, 2023

(30) Foreign Application Priority Data

Dec. 20, 2019 (DE) ..................... 10 2019 135 349.1

(51) Int. Cl.

| | |
|---|---|
| ***C11D 3/386*** | (2006.01) |
| ***C11D 3/12*** | (2006.01) |
| ***C11D 3/22*** | (2006.01) |
| ***C11D 3/36*** | (2006.01) |
| ***C11D 3/39*** | (2006.01) |
| ***C12N 9/24*** | (2006.01) |
| ***C12N 9/52*** | (2006.01) |

(52) U.S. Cl.
CPC .......... *C11D 3/38636* (2013.01); *C11D 3/128* (2013.01); *C11D 3/222* (2013.01); *C11D 3/361* (2013.01); *C11D 3/3905* (2013.01); *C12N 9/2402* (2013.01); *C12N 9/52* (2013.01); *C12Y 302/01052* (2013.01); *C12Y 304/21062* (2013.01)

(58) Field of Classification Search
CPC .................................................... C12N 9/2402
See application file for complete search history.

(56) References Cited

U.S. PATENT DOCUMENTS

| | | | |
|---|---|---|---|
| 4,106,991 | A | 8/1978 | Markussen et al. |
| 4,435,307 | A | 3/1984 | Barbesgaard et al. |
| 4,661,452 | A | 4/1987 | Markussen et al. |
| 4,664,839 | A | 5/1987 | Rieck |
| 5,352,604 | A | 10/1994 | Wilson et al. |
| 5,389,536 | A | 2/1995 | Gray et al. |
| 5,453,372 | A | 9/1995 | Vetter et al. |
| 5,457,046 | A | 10/1995 | Wöldike et al. |
| 5,648,263 | A | 7/1997 | Schülein et al. |
| 5,686,593 | A | 11/1997 | Wöldike et al. |
| 5,691,178 | A | 11/1997 | Schülein et al. |
| 5,763,254 | A | 6/1998 | Wöldike et al. |
| 5,776,757 | A | 7/1998 | Schülein et al. |
| 5,827,718 | A | 10/1998 | Ishida et al. |
| 5,888,954 | A | 3/1999 | Haerer et al. |
| 5,942,431 | A | 8/1999 | Yoneda et al. |
| 5,977,053 | A | 11/1999 | Groth et al. |
| 6,197,589 | B1 | 3/2001 | Maurer et al. |
| 6,218,165 | B1 | 4/2001 | Estell et al. |
| 6,313,081 | B1 | 11/2001 | Lenting et al. |
| 6,461,849 | B1 | 10/2002 | Olsen et al. |
| 6,465,410 | B1 | 10/2002 | Bettiol et al. |
| 6,468,955 | B1 | 10/2002 | Smets et al. |
| 6,566,114 | B1 | 5/2003 | Kauppinen et al. |
| 7,062,042 | B1 | 6/2006 | Gilbert |
| 7,262,042 | B2 | 8/2007 | Weber et al. |
| 7,993,898 | B2 | 8/2011 | Andersen et al. |
| 8,202,831 | B2 | 6/2012 | Lant et al. |
| 8,399,235 | B2 | 3/2013 | Frank et al. |
| 8,821,862 | B2 | 9/2014 | Madhyastha et al. |
| 10,030,239 | B2 | 7/2018 | Gjermansen |

(Continued)

FOREIGN PATENT DOCUMENTS

| | | | |
|---|---|---|---|
| AU | 6559390 | A | 5/1991 |
| CA | 2202553 | A1 | 4/1997 |

(Continued)

OTHER PUBLICATIONS

Search Report dated Oct. 8, 2020 from parallel German patent application No. 10 2019 135 349.1, 7 pages, for Information purpose only.

(Continued)

*Primary Examiner* — Suzanne M Noakes
(74) *Attorney, Agent, or Firm* — CANTOR COLBURN LLP

(57) ABSTRACT

Cleaning compositions may include a mix of enzymes that include a mix of enzymes. Said compositions may be used in cleaning processes and/or for deep cleaning of organic stains, and for removal or reduction of components of organic matter.

8 Claims, No Drawings

Specification includes a Sequence Listing.

(56) References Cited

U.S. PATENT DOCUMENTS

| | | | |
|---|---|---|---|
| 11,732,220 | B2 | 8/2023 | Weide et al. |
| 2005/0261158 | A1 | 11/2005 | Kottwitz et al. |
| 2008/0153983 | A1 | 6/2008 | Boeckh et al. |
| 2009/0011970 | A1 | 1/2009 | Evers |
| 2009/0155215 | A1 | 6/2009 | Collins et al. |
| 2011/0196319 | A1 | 8/2011 | Arscott, II et al. |
| 2012/0258089 | A1 | 10/2012 | Madhyastha et al. |
| 2014/0080178 | A1 | 3/2014 | Schnorr et al. |
| 2014/0295522 | A1 | 10/2014 | Mussmann et al. |
| 2016/0017304 | A1 | 1/2016 | Cascao-Pereira et al. |
| 2017/0240877 | A1 | 8/2017 | Andersen et al. |
| 2017/0355931 | A1 | 12/2017 | Lant et al. |
| 2017/0355932 | A1 | 12/2017 | Lant et al. |
| 2017/0355933 | A1 | 12/2017 | Lant et al. |
| 2018/0155802 | A1 | 6/2018 | Lant |
| 2018/0163191 | A1 | 6/2018 | Cuevas et al. |
| 2019/0127663 | A1 | 5/2019 | Oehlenschlaeger et al. |
| 2019/0144792 | A1 | 5/2019 | Herbst et al. |
| 2019/0153417 | A1 | 5/2019 | Adams et al. |
| 2019/0161707 | A1 | 5/2019 | Vejborg et al. |
| 2019/0169547 | A1 | 6/2019 | Ooehlenschlaeger et al. |
| 2019/0284511 | A1 | 9/2019 | Oehlenschlaeger et al. |
| 2020/0347324 | A1 | 11/2020 | Wieland et al. |
| 2021/0222089 | A1 | 7/2021 | Blackman et al. |
| 2023/0024242 | A1 | 1/2023 | Weide et al. |
| 2023/0040230 | A1 | 2/2023 | Weide et al. |
| 2023/0045289 | A1 | 2/2023 | Weide et al. |
| 2023/0303953 | A1 | 9/2023 | Weide et al. |

FOREIGN PATENT DOCUMENTS

| | | | |
|---|---|---|---|
| CN | 109415665 | A | 3/2019 |
| DE | 102017125558 | A1 | 5/2019 |
| DE | 102017125559 | A1 | 5/2019 |
| EP | 0164514 | A1 | 12/1985 |
| EP | 0179486 | A2 | 4/1986 |
| EP | 0218272 | A1 | 4/1987 |
| EP | 0238216 | A1 | 9/1987 |
| EP | 0258068 | A2 | 3/1988 |
| EP | 0305216 | A1 | 3/1989 |
| EP | 0331376 | A2 | 9/1989 |
| EP | 0407225 | A1 | 1/1991 |
| EP | 0495257 | A1 | 7/1992 |
| EP | 0531372 | B1 | 2/1995 |
| EP | 0531315 | B1 | 3/1997 |
| EP | 0624154 | B1 | 9/1999 |
| EP | 1867708 | A1 | 12/2007 |
| EP | 1876226 | A1 | 1/2008 |
| EP | 1921147 | A2 | 5/2008 |
| EP | 1921148 | A2 | 5/2008 |
| EP | 2169040 | A1 | 3/2010 |
| EP | 3088506 | A1 | 11/2016 |
| EP | 3309244 | A1 | 4/2018 |
| EP | 3330353 | A1 | 6/2018 |
| EP | 3034596 | B1 | 8/2018 |
| EP | 2516606 | B1 | 1/2019 |
| EP | 3533859 | A1 | 9/2019 |
| EP | 3647397 | A1 | 5/2020 |
| EP | 3647398 | A1 | 5/2020 |
| GB | 1296839 | A | 11/1972 |
| GB | 1483591 | A | 8/1977 |
| JP | H02238885 | A | 9/1990 |
| JP | H07143883 | A | 6/1995 |
| JP | 2000210081 | A | 8/2000 |
| JP | 2005247981 | A | 9/2005 |
| NO | 9117243 | A1 | 11/1991 |
| WO | 8906279 | A1 | 7/1989 |
| WO | 8909259 | A1 | 10/1989 |
| WO | 9102792 | A1 | 3/1991 |
| WO | 9117244 | A1 | 11/1991 |
| WO | 9201046 | A1 | 1/1992 |
| WO | 9205249 | A1 | 4/1992 |
| WO | 9219729 | A1 | 11/1992 |
| WO | 9221760 | A1 | 12/1992 |
| WO | 9307263 | A2 | 4/1993 |
| WO | 9318140 | A1 | 9/1993 |
| WO | 9324618 | A1 | 12/1993 |
| WO | 9401541 | A1 | 1/1994 |
| WO | 9402597 | A1 | 2/1994 |
| WO | 9407998 | A1 | 4/1994 |
| WO | 9418314 | A1 | 8/1994 |
| WO | 9425578 | A1 | 11/1994 |
| WO | 9425583 | A1 | 11/1994 |
| WO | 9426859 | A1 | 11/1994 |
| WO | 9426860 | A1 | 11/1994 |
| WO | 9506720 | A1 | 3/1995 |
| WO | 9510602 | A1 | 4/1995 |
| WO | 9510603 | A1 | 4/1995 |
| WO | 9514783 | A1 | 6/1995 |
| WO | 9522615 | A1 | 8/1995 |
| WO | 9523221 | A1 | 8/1995 |
| WO | 9524471 | A1 | 9/1995 |
| WO | 9527046 | A2 | 10/1995 |
| WO | 9530744 | A2 | 11/1995 |
| WO | 9533836 | A1 | 12/1995 |
| WO | 9535381 | A1 | 12/1995 |
| WO | 9600292 | A1 | 1/1996 |
| WO | 9611262 | A1 | 4/1996 |
| WO | 9612012 | A1 | 4/1996 |
| WO | 9613580 | A1 | 5/1996 |
| WO | 9623873 | A1 | 8/1996 |
| WO | 9627002 | A1 | 9/1996 |
| WO | 9629397 | A1 | 9/1996 |
| WO | 9634946 | A1 | 11/1996 |
| WO | 9704079 | A1 | 2/1997 |
| WO | 9704102 | A1 | 2/1997 |
| WO | 9707202 | A1 | 2/1997 |
| WO | 9708325 | A2 | 3/1997 |
| WO | 9723606 | A1 | 7/1997 |
| WO | 9743424 | A1 | 11/1997 |
| WO | 9808940 | A1 | 3/1998 |
| WO | 9812307 | A1 | 3/1998 |
| WO | 9815257 | A1 | 4/1998 |
| WO | 9817767 | A1 | 4/1998 |
| WO | 9820115 | A1 | 5/1998 |
| WO | 9820116 | A1 | 5/1998 |
| WO | 9850512 | A1 | 11/1998 |
| WO | 9901544 | A1 | 1/1999 |
| WO | 9911768 | A1 | 3/1999 |
| WO | 9919467 | A1 | 4/1999 |
| WO | 9932595 | A1 | 7/1999 |
| WO | 9957155 | A1 | 11/1999 |
| WO | 9957157 | A1 | 11/1999 |
| WO | 9964619 | A2 | 12/1999 |
| WO | 0001793 | A1 | 1/2000 |
| WO | 0034450 | A1 | 6/2000 |
| WO | 0060063 | A1 | 10/2000 |
| WO | 0116285 | A2 | 3/2001 |
| WO | 0144452 | A1 | 6/2001 |
| WO | 0162903 | A1 | 8/2001 |
| WO | 0166712 | A2 | 9/2001 |
| WO | 0179458 | A2 | 10/2001 |
| WO | 0179459 | A2 | 10/2001 |
| WO | 0179460 | A2 | 10/2001 |
| WO | 0179461 | A2 | 10/2001 |
| WO | 0192502 | A1 | 12/2001 |
| WO | 0210355 | A2 | 2/2002 |
| WO | 0216547 | A2 | 2/2002 |
| WO | 02099091 | A2 | 12/2002 |
| WO | 03006602 | A2 | 1/2003 |
| WO | 03040279 | A1 | 5/2003 |
| WO | 2004003186 | A2 | 1/2004 |
| WO | 2004041979 | A2 | 5/2004 |
| WO | 2004061117 | A2 | 7/2004 |
| WO | 2004067737 | A2 | 8/2004 |
| WO | 2005003274 | A1 | 1/2005 |
| WO | 2005003275 | A1 | 1/2005 |
| WO | 2005003276 | A1 | 1/2005 |
| WO | 2005040372 | A1 | 5/2005 |
| WO | 200556782 | A2 | 6/2005 |
| WO | 2005052146 | A2 | 6/2005 |
| WO | 2005052161 | A2 | 6/2005 |
| WO | 2006031554 | A2 | 3/2006 |
| WO | 2006034710 | A1 | 4/2006 |

(56) References Cited

FOREIGN PATENT DOCUMENTS

| | | | |
|---|---|---|---|
| WO | 2006066594 | A2 | 6/2006 |
| WO | 2006108856 | A2 | 10/2006 |
| WO | 2006113314 | A1 | 10/2006 |
| WO | 2006130575 | A2 | 12/2006 |
| WO | 2007006305 | A1 | 1/2007 |
| WO | 2007044993 | A2 | 4/2007 |
| WO | 2007087242 | A2 | 8/2007 |
| WO | 2007087243 | A2 | 8/2007 |
| WO | 2007087244 | A2 | 8/2007 |
| WO | 2007087257 | A2 | 8/2007 |
| WO | 2007087258 | A2 | 8/2007 |
| WO | 2007087259 | A2 | 8/2007 |
| WO | 2007087508 | A2 | 8/2007 |
| WO | 2007138054 | A1 | 12/2007 |
| WO | 2008043175 | A1 | 4/2008 |
| WO | 2008153815 | A2 | 12/2008 |
| WO | 2008157350 | A2 | 12/2008 |
| WO | 2009021867 | A2 | 2/2009 |
| WO | 2009043709 | A1 | 4/2009 |
| WO | 2009061380 | A2 | 5/2009 |
| WO | 2009067279 | A1 | 5/2009 |
| WO | 2009087523 | A2 | 7/2009 |
| WO | 2009102854 | A1 | 8/2009 |
| WO | 2009109500 | A1 | 9/2009 |
| WO | 2009121183 | A1 | 10/2009 |
| WO | 2010065455 | A2 | 6/2010 |
| WO | 2010100028 | A2 | 9/2010 |
| WO | 2010104675 | A1 | 9/2010 |
| WO | 2010107560 | A2 | 9/2010 |
| WO | 2010111143 | A2 | 9/2010 |
| WO | 2011036263 | A1 | 3/2011 |
| WO | 2011036264 | A1 | 3/2011 |
| WO | 2011084412 | A1 | 7/2011 |
| WO | 2011084417 | A1 | 7/2011 |
| WO | 2011084599 | A1 | 7/2011 |
| WO | 2011098531 | A1 | 8/2011 |
| WO | 2011150157 | A2 | 12/2011 |
| WO | 2011163325 | A1 | 12/2011 |
| WO | 2012129515 | A1 | 9/2012 |
| WO | 2012137147 | A1 | 10/2012 |
| WO | 2013001078 | A1 | 1/2013 |
| WO | 2013001087 | A2 | 1/2013 |
| WO | 2013016368 | A1 | 1/2013 |
| WO | 2013060621 | A1 | 5/2013 |
| WO | 2013087545 | A1 | 6/2013 |
| WO | 2013184577 | A1 | 12/2013 |
| WO | 2013188331 | A1 | 12/2013 |
| WO | 2014110675 | A1 | 7/2014 |
| WO | 2014124927 | A2 | 8/2014 |
| WO | 2014207227 | A1 | 12/2014 |
| WO | 2015014790 | A2 | 2/2015 |
| WO | 2015014803 | A1 | 2/2015 |
| WO | 2015014804 | A1 | 2/2015 |
| WO | 2015040159 | A2 | 3/2015 |
| WO | 2015158723 | A1 | 10/2015 |
| WO | 2015196299 | A1 | 12/2015 |
| WO | 2016001449 | A1 | 1/2016 |
| WO | 2016075078 | A2 | 5/2016 |
| WO | 2016087617 | A1 | 6/2016 |
| WO | 2016096711 | A2 | 6/2016 |
| WO | 2016096714 | A1 | 6/2016 |
| WO | 2016097350 | A1 | 6/2016 |
| WO | 2016097352 | A1 | 6/2016 |
| WO | 2016097354 | A1 | 6/2016 |
| WO | 2016097357 | A1 | 6/2016 |
| WO | 2016174234 | A2 | 11/2016 |
| WO | 2016176240 | A1 | 11/2016 |
| WO | 2016176241 | A1 | 11/2016 |
| WO | 2016176280 | A1 | 11/2016 |
| WO | 2017021515 | A1 | 2/2017 |
| WO | 2017021516 | A1 | 2/2017 |
| WO | 2017021517 | A1 | 2/2017 |
| WO | 2017021518 | A1 | 2/2017 |
| WO | 2017079751 | A1 | 5/2017 |
| WO | 2017097866 | A1 | 6/2017 |
| WO | 2017156098 | A1 | 9/2017 |
| WO | 2017186936 | A1 | 11/2017 |
| WO | 2017186937 | A1 | 11/2017 |
| WO | 2017186943 | A1 | 11/2017 |
| WO | 2017207770 | A1 | 12/2017 |
| WO | 2017210295 | A1 | 12/2017 |
| WO | 2017214240 | A2 | 12/2017 |
| WO | 2018002194 | A1 | 1/2018 |
| WO | 2018085524 | A2 | 5/2018 |
| WO | 2018102478 | A1 | 6/2018 |
| WO | 2018184816 | A1 | 10/2018 |
| WO | 2018184873 | A1 | 10/2018 |
| WO | 2019086520 | A1 | 5/2019 |
| WO | 2019086521 | A1 | 5/2019 |
| WO | 2019086526 | A1 | 5/2019 |
| WO | 2019086528 | A1 | 5/2019 |
| WO | 2019086530 | A1 | 5/2019 |
| WO | 2020007863 | A1 | 1/2020 |
| WO | 2020007875 | A1 | 1/2020 |
| WO | 2021122117 | A1 | 6/2021 |

OTHER PUBLICATIONS

Search Report dated May 11, 2021 from parallel PCT-application No. PCT/EP2020/084947, 9 pages, for information purpose only.
International Search Report for International Application PCT/EP2020/084940; International Filing Date: May 4, 2021; 9 pages.
International Search Report for International Application PCT/EP2020/084950; International Filing Date: Aug. 30, 2021; 10 pages.
International Search Report for International Application PCT/EP2020/084952; International Filing Date: May 4, 2021; 9 pages.
International Search Report for International Application PCT/EP2021/068393; International Filing Date: Oct. 25, 2021; 14 pages.
UniProtKB—A0A075LPR4 (https://www.uniprot.org/uniprotkb/A0A075LPR4/entry) (Last sequence update: Oct. 29, 2014) 4 pages.
"SubName: Full=Uncharacterized protein {ECO:0000313 EMBL:AIF67972.1}"; Uniprot, Oct. 29, 2014; 1 page.
"SubName: Full=Uncharacterized protein {ECO:0000313 EMBL:KKI62758.1}"; Uniprot, Nov. 11, 2015.
Branden et al.; Introduction to Protein Structure, Garland Publishing Inc., New York, p. 247 (1991).
Durkin et al.; EBI Accession No. J4TU99 (2012).
EP Communication pursuant to Rule 164(2)(b) and Article 94(3) EPC for Application No. 20824151.3 dated Sep. 25, 2024.
Gillaspy et al.; EBI Accession No. X2JMQ1 (2014).
International Search Report and Written Opinion for International Application PCT/EP2018/079836; International Filing Date: Oct. 31, 2018; Date of Mailing: Mar. 29, 2019; 15 pages.
International Search Report and Written Opinion for International Application PCT/EP2018/079845; International Filing Date: Oct. 31, 2018; Date of Mailing: Feb. 28, 2019; 16 pages.
Jackson et al.; EBI Accession No. P86956 (2011).
Joubert et al.; EBI Accession No. H2A0L6 (2012).
Kaplan et al.; "Detachment of Actinobacillus actinomycetemcomitans Biofilm Cells by an Endogenous ß-Hexosaminidase Activity"; J Bacteriol, vol. 185, Issue No. 16; pp. 4693-4698 (2003).
Kaplan et al.; EBI Accession No. Q6GYA5 (2003).
Keeling, et al.; UniProt Accession No. U4URB2 (2013).
Kurata, N. et al.; "Surfactant-associated bacteria in the near-surface layer of the ocean"; Sci Rep, vol. 6, 19123; DOI:10.1038/srep19123 (2016).
Liu et al; "*Terribacillus aidingensis* sp. nov., a moderately halophilic bacterium"; Int Sys Evol Microbiol, vol. 60, Issue No. 12; pp. 2940-2945 (2010).
Liu, Y. et al.; "Biochemical Characterization & Structural Analysis of a B-N-Acetylglucosaminidase from Paenibacillus barengoltzii for Efficient Production of N-Acetyl-D-glucosamine"; J Agric Food Chem 68; pp. 5648-5657; DOI: 10.1021/acs.jafc.9b08085 (2020).
Macinnes et al.; EBI Accession No. A0A0A7IMHS5 (2015).
Macinnes et al.; EBI Accession No. K0G581 (2012).
Mckinlay, et al.; UniProt Accession No. A6VMN2 (2007).
NCBI No. WP_005560708 (2013).
NCBI No. WP_017886882.1 (2013).

(56) References Cited

OTHER PUBLICATIONS

NCBI No. WP_018652103 (2013).
NCBI No. WP_051596815.1 (2015).
Probiotic, New Probiotic liquid laundry detergents with unique AcitveProbiotics technology, published online May 9, 2017.
Ramasubbu et al; "Structural Analysis of Dispersin B, a Biofilm-releasing Glycoside Hydrolase from the Periodontopathogen Actinobacillus actinomycetemcomitans"; J Mol Biol, vol. 349, Issue No. 3; pp. 475-486; DOI:10.1016/j.jmb.2005.03.082 (2005).
RapidTables, Percent (%) to ppm conversion calculator, accessed online at "https://www.rapidtables.com/convert/number/Percent_to_PPM.html" on Sep. 24, 2020.
Sadowski et al.; "The sequence-structure relationship and protein function prediction"; Current Opinion in Structural Biology, vol. 19, Issue No. 3; pp. 357-362; DOI: 10.1016/j.sbi.2009.03.008 (2009).
Seffernick et al.; "Melamine deaminase and atrazine chlorohydrolase: 98 percent identical but functionally different"; J Bacteriol, vol. 183, Issue No. 8; pp. 2405-2410; DOI: 10.1128/JB.183.8.2405-2410.2001 (2001).
Tang, et al.; "Identification of Dehalobacter reductive dehalogenases that catalyse dechlorination of chloroform, 1,1,1-trichloroethane and 1,1-dichloroethane"; Phil Trans R Soc B, vol. 368, Mar. 18, 2012; pp. 1-10; DOI: 10.1098/rstb.2012.0318 (2013).
Tews et al.; EBI Accession No. Q54468 (1998).
Uniprot Accession No. A0A0Q5CMZ8 (www.uniprot.org/uniprotkb/A0A0Q5CMZ8/entry) Last update: Jan. 20, 2016; 4 pages.
Uniprot Accession No. A0A0Q5KJC4 (https://www.uniprot.org/uniprotkb/A0A0Q5KJC4/history) Last update: Aug. 12, 2020; 2 pages (2020).
Uniprot Protein Database, protein Accession A0A5DOEMY6_AGGAC, Beta-N-acetylhexosaminidase (2021).
Varghese; GenBank Accession No. SEN27755, published Oct. 29, 2016.
Ward, et al.; UniProt Accession No. D7N318; May 25, 2022.
Weinstock et al.; UniProt Accession No. E4HHI5; Jan. 24, 2024.
Witkowski et al.; "Conversion of a beta-ketoacyl synthase to a malonyl decarboxylase by replacement of the active-site cysteine with glutamine"; Biochemistry, vol. 38; pp. 11643-11650; DOI: 10.1021/bi990993h (1999).
Zhan et al.; UniProt Accession No. D9PABO; Jun. 7, 2017.
Needleman, Saul B. et al., "A General Method Applicable to the Search for Similarities in the Amino Acid Sequence of Two Proteins", J. Mol. Biol., 1970, pp. 443-453, vol. 48.
Rice, Peter et al. "EMBOSS: The European Molecular Biology Open Software Suite", TIG Jun. 2000, pp. 276-277, vol. 16, No. 6, Elsevier Science Ltd.
Siezen, Roland J. et al., "Homology modelling and protein engineering strategy of subtilases, the family of subtilisin-like serine proteinases", Protein Engineering, 1991, pp. 719-737, vol. 4, No. 7, Oxford University Press.
Siezen R.J. et al., "Subtilases: The superfamily of subtilisin-like serine proteases", Protein Sci., 1997, pp. 501-523, vol. 6, Cold Spring Harbor Laboratory Press.

CLEANING COMPOSITIONS COMPRISING DISPERSINS VI

CROSS-REFERENCE TO RELATED APPLICATIONS

The present application is a national stage entry according to 35 U.S.C. § 371 of PCT application No.: PCT/EP2020/084947 filed on Dec. 7, 2020; which claims priority to German patent application 10 2019 135 349.1, filed on Dec. 20, 2019; all of which are incorporated herein by reference in their entirety and for all purposes.

REFERENCE TO A SEQUENCE LISTING SUBMITTED VIA EFS-WEB

The content of the ASCII text file of the sequence listing named "2019P00533WOUS_P83437_seqlist_final", which is 91 kb in size was created on Dec. 20, 2019. The sequence listing was corrected on Jun. 15, 2022 to correctly define the source of the genetic material; the corrected sequence listing is electronically submitted via EFS-Web herewith; the original sequence listing and the corrected sequence listing are incorporated by reference in their entirety.

TECHNICAL FIELD

The present invention relates to specific cleaning compositions comprising a mix of enzymes. The invention further relates to the use of said compositions in cleaning processes and/or for deep cleaning of organic stains, and to methods of using said compositions for removal or reduction of components of organic matter.

BACKGROUND

Enzymes have been used in detergents for decades. Usually a cocktail of various enzymes is added to detergent compositions, wherein each enzyme targets a specific substrate, e.g. amylases are active towards starch stains, proteases on protein stains and so forth. The effectiveness of these commercial enzymes provides detergents which remove much of the soiling. However, components of organic matters such as biofilm and EPS (extracellular polymeric substance) constitute a challenging type of staining due to the complex nature of such organic matter, and commercially available cleaning compositions are not able to effectively remove or reduce EPS and/or biofilm related stains. Textile surfaces and hard surfaces, such as dishes or the inner space of a laundry machine enduring a number of wash cycles, become soiled with many different types of soiling which may compose of proteins, grease, starch etc. One type of stain may be associated with organic matter such as biofilm, EPS (extracellular polymeric substance), etc. Organic matter may be composed of different molecules such as polysaccharides, extracellular DNA (eDNA), and proteins. Some organic matter comprises an extracellular polymeric matrix, which may be sticky or glueing, which when present on textile attracts soils and may cause redeposition or backstaining of soil, resulting in a greying of the textile. Additionally, organic matters such as biofilms often cause malodor issues as various malodor molecules can be adhered by the polysaccharides, extracellular DNA (eDNA) and proteins in the complex extracellular matrix and be slowly released to cause a noticeable malodor. There is thus still a need for cleaning compositions which effectively prevent, reduce or remove stains e.g. associated with biofilms, such as protein and polysaccharides, e.g. PNAG (poly-β(1-6)-N-acetylglucosamine). The present invention provides new compositions fulfilling such need.

SUMMARY

A first aspect of the present invention relates to a cleaning composition, as defined herein, comprising a dispersin and a protease, as per the appended claims.

The cleaning composition of the invention that comprises a dispersin and a protease, (a) is a solid, preferably granular, laundry detergent composition and further comprises (a1) at least one zeolite builder, preferably in an amount of 10 to 50 wt.-%, more preferably 20-30 wt.-%;

(a2) at least one phosphonate builder, preferably in an amount of 0.1 to 5 wt.-%, more preferably 0.4 to 1.5 wt.-%;

(a3) at least one further enzyme, preferably a cellulase, preferably in an amount of active enzyme of 100 to 5000 ppb, more preferably 1000 to 2000 ppb; and (a4) at least one polymer, preferably a polyvinylpyrrolidon polymer, preferably in an amount of 0.01 to 1 wt.-%, more preferably 0.1 to 0.3 wt.-%; or (b) is a solid laundry detergent composition and further comprises (b1) at least one silicate builder, preferably in an amount of 2 to 20 wt.-%, more preferably 5-10 wt.-%;

(b2) optionally carboxymethylcellulose, preferably in an amount of 0.1 to 10 wt.-%, more preferably 0.1 to 4 wt.-%;

(b3) at least one further enzyme, preferably a cellulase, preferably in an amount of active enzyme of 0.1 to 100 ppm, more preferably 0.1 to 10 ppm;

(b4) optionally at least one soil release polymer, preferably a polyvinylpyrrolidon polymer, in an amount of 0.1 to 3 wt.-%, more preferably 0.1 to 1.0 wt.-%; and (b5) at least one bleaching system, comprising a bleaching agent, a bleach activator and a bleach catalyst, preferably in an amount of 0.1 to 50 wt.-%, more preferably 0.1 to 30 wt.-%; or (c) is liquid laundry detergent composition and further comprises (c1) at least one surfactant, preferably nonionic surfactant, preferably in an amount of 1 to 20 wt.-%, preferably 3 to 15 wt.-%;

(c2) optionally at least one phosphonate builder, preferably in an amount of 0.1 to 3 wt.-%, more preferably 0.25 to 1.5 wt.-%

(c3) optionally at least at least one further enzyme, preferably a cellulase, preferably in an amount of enzyme composition of 0.001 to 1 wt.-%, more preferably 0.001 to 0.6 wt.-%; and (c4) optionally at least one organic solvent, preferably glycerol, preferably in an amount of 0.1 to 10 wt.-%, more preferably 0.1 to 5 wt.-%; or (d) is a liquid laundry detergent in unit dose form, preferably a pouch comprising a water-soluble film, and further comprises (d1) water in an amount of up to 20 wt.-%, preferably 5 to 15 wt.-%;

(d2) optionally at least one bittering agent, preferably Benzyldiethyl(2,6-xylylcarbamoyl)-methylammoniumbenzoate, preferably in an amount of 0.00001 to 0.04 wt.-%;

(d3) optionally at least one optical brightener, preferably in an amount of 0.01 to 2 wt.-%, more preferably 0.01 to 1 wt.-%; and (d4) optionally at least one polymer, preferably in an amount of 0.01 to 7 wt.-%, more preferably 0.1 to 5 wt.-%; or (e) is a fabric finisher and further comprises (e1) at least one softening silicone, preferably an amino-functionalized silicone, preferably in an amount of 0.1 to 10 wt.-%, more preferably 0.1 to 2 wt.-%;

(e2) at least one perfume, preferably at least partially encapsulated in microcapsules, more preferably at least partially encapsulated in melamine-formaldehyde microcapsules, preferably in an amount of 0.01 to 3 wt.-%, more preferably 0.1 to 1 wt.-%;

(e3) optionally polyquaternium 10 in an amount of 0.1 to 20 wt.-%, preferably 0.1 to 13 wt.-%;

(e4) optionally polyquaternium 37 in an amount of 0.1 to 20 wt.-%, preferably 0.1 to 13 wt.-%;

(e5) optionally a plant-based esterquat, preferably a canola- or palm-based esterquat, in an amount of 0.1 to 20 wt.-%, preferably 0.1 to 13 wt.-%; and (e6) optionally adipic acid, in an amount of 0.1 to 20 wt.-%, preferably 0.1 to 13 wt.-%; or (f) is an acidic cleaning agent, preferably having a pH less than 6, and further comprises (f1) plant-based or bio-based surfactants, preferably each in an amount of 0.1 to 5, more preferably each in an amount of 0.1 to 2 wt.-%;

(f2) at least one acidic biocide, preferably selected from acids, more preferably HCl and formic acid; and (f3) at least one soil release, water repellant or water spreading polymer, preferably in an amount of 0.01 to 3 wt.-%, more preferably 0.01 to 0.5 wt.-%; or (g) is a neutral cleaning agent, preferably having a pH between 6.0 and 7.5, and further comprises (g1) plant-based or bio-based surfactants, preferably each in an amount of 0.1 to 5, more preferably each in an amount of 0.1 to 2 wt.-%;

(g2) at least one biocide, preferably selected from quaternary ammonium compounds and alcohols; and (g3) at least one soil release, water repellant or water spreading polymer, preferably in an amount of 0.01 to 3 wt.-%, more preferably 0.01 to 0.5 wt.-%; or (h) is an alkaline cleaning agent, preferably having a pH of more than 7.5, and further comprises (h1) plant-based or bio-based surfactants, preferably each in an amount of 0.1 to 5, more preferably each in an amount of 0.1 to 2 wt.-%; or (i) is a hand dishwashing agent, preferably liquid hand dishwashing agent, and further comprises (i1) at least one anionic surfactant, preferably in an amount of 0.1 to 40 wt.-%, more preferably 5 to 30 wt.-%;

(i2) at least one amphoteric surfactant, preferably betain, preferably in an amount of 0.1 to 25 wt.-%, more preferably 1 to 15 wt.-%;

(i3) at least one nonionic surfactant, preferably in an amount of 0.1 to 25 wt.-%, more preferably 2 to 10 wt.-%;

(i4) at least one further enzyme, preferably selected from amylases, preferably in an amount of enzyme composition of up to 1 wt.-%, more preferably up to 0.6 wt.-%; or (j) is an automatic dishwashing composition and further comprises (j1) at least one builder selected from citrate, aminocarboxylates and combinations thereof, preferably in an amount of 5 to 30 wt.-%, more preferably 10 to 20 wt.-%;

(j2) at least one phosphonate builder, preferably in an amount of 0.1 to 5 wt.-%, more preferably 0.4 to 1.5 wt.-%;

(j3) at least one nonionic surfactant, preferably in an amount of 0.1 to 10 wt.-%, more preferably 1 to 5 wt.-%;

(j4) at least one bleaching system, comprising a bleaching agent, a bleach activator and a bleach catalyst, preferably in an amount of 0.1 to 50 wt.-%, more preferably 0.1 to 30 wt.-%; and (j5) at least one polymer selected from sulfopolymers, cationic polymers and polyacrylates, preferably in an amount of 0.01 to 15 wt.-%, more preferably 2 to 10 wt.-%; or (k) further comprises (k1) at least one sulfopolymer, preferably in an amount of 1 to 15, more preferably 2 to 10 wt.-% and is preferably a dishwashing, more preferably an automatic dishwashing composition; or (l) further comprises at least one adjunct ingredient selected from probiotics, preferably microbes, spores or combinations thereof; or (m) is in unit dose form and comprises at least 2, preferably 2, 3, 4 or 5 separate compartments; or (n) is a phosphate-free composition.

When in the following reference is made to "(cleaning) compositions of the invention" or "(cleaning) compositions as described herein" or "(cleaning) compositions as defined herein", the above-specified compositions (a)-(n) are meant. Furthermore, if not indicated otherwise, all references to percentages in relation to the disclosed compositions relate to wt % relative to the total weight of the respective composition. It is understood that when reference is made to compositions that contain enzymes as defined herein, the respective composition contains at least one of each of the specified enzymes but can also comprise two or more of each enzyme type, such as two or more dispersins and/or two or more proteases.

The invention further relates to the use of a cleaning composition, as defined herein, comprising a dispersin and a protease for deep cleaning of an item, wherein the item is a textile or a surface.

The invention further relates to a method of deep cleaning of an item, comprising the steps of:

a) contacting the item with a cleaning composition, as defined herein, comprising a dispersin and a protease; and b) optionally rinsing the item, wherein the item is preferably a textile.

DETAILED DESCRIPTION

Components of organic matter such as biofilm and EPS (extracellular polymeric substance) constitute a challenging type of staining due to the complex nature of such organic matters, and commercially available cleaning compositions are unable to effectively remove or reduce EPS and/or biofilm related stains. Biofilm may be produced when a group of microorganisms' cells stick to each other or stick to a surface, such as a textile, dishware or hard surface. These adherent cells are frequently embedded within a self-produced matrix of extracellular polymeric substance (EPS), which constitute 50% to 90% of the biofilm's total organic matter. EPS is mostly composed of polysaccharides (exopolysaccharides) and proteins, but include other macromolecules such as eDNA, lipids and other organic substances. These proteins and polysaccharides such as PNAG are difficult to remove with the traditional cleaning compositions. Further, organic matter such EPS or biofilm may be sticky or glueing, which when present on textile may give rise to redeposition or backstaining of soil, resulting in a greying of the textile. When dirty laundry items are washed together with less dirty laundry items the dirt present in the wash liquor tends to stick to organic matter such as biofilm or biofilm components, and as a result the laundry item may be more "soiled" after wash than before wash, which is termed re-deposition. Another drawback of the presence organic matter e.g. biofilm is the malodor.

The compositions of the invention comprise a blend of dispersin and protease and effectively reduce or remove organic components, such as protein and PNAG, from surfaces such as textiles and hard surfaces e.g. dishes.

The compositions of the invention comprising a blend of dispersin and protease and effectively reduce or limit redeposition when applied in e.g. a laundry process.

The compositions of the invention comprising a blend of dispersin and protease and effectively reduce or limit malodor of e.g. textiles or hard surfaces such as dishes.

The compositions of the invention comprising a blend of dispersin and protease and improve whiteness of textiles.

A composition of the invention is preferably a cleaning composition, as defined herein, comprising at least one dispersin and at least one protease. Examples of useful dispersins and proteases are mentioned below in the sections "Polypeptides having hexosaminidase activity" and "Polypeptides having protease activity" respectively.

As shown in the example herein, it has been found that a combination of a dispersin and a protease is able to provide improved deep-cleaning of a textile compared to the individual enzymes. It is contemplated that this may be the result of the different EPS components targeted by these enzymes being localized in complex macromolecular structures which shield each other from enzymatic hydrolysis, and that use of the two different enzymes allows these complex structures to be degraded, thereby facilitating removal of the EPS biofilm.

Polypeptides Having Hexosaminidase Activity (Hexosaminidases)

The term hexosaminidase includes "dispersin" and the abbreviation "Dsp", and means a polypeptide having hexosaminidase activity, EC 3.2.1., that catalyzes the hydrolysis of β-1,6-glycosidic linkages of N-acetyl-glucosamine polymers found e.g. in biofilm. The term hexosaminidase includes polypeptides having N-acetylglucosaminidase activity and β-N-acetylglucosaminidase activity. The term "polypeptide having hexosaminidase activity" may be used interchangeably with the term hexosaminidases and similarly the term "polypeptide having β-N-acetylglucosaminidase activity" may be used interchangeably with the term β-N-acetylglucosaminidases. For purposes of the present invention, hexosaminidase activity is determined according to the procedure described in Assay II. In a preferred embodiment, the polypeptide having hexosaminidase activity is a dispersin. In a preferred embodiment, the polypeptide having hexosaminidase activity is a β-N-acetylglucosaminidase targeting poly-β-1,6-N-acetylglucosamine.

In one embodiment, the invention relates to a composition comprising a protease, a hexosaminidase, preferably a β-N-acetylglucosaminidase e.g. a dispersin, and a cleaning component.

One embodiment of the invention relates to a composition, as defined herein, comprising a hexosaminidase polypeptide, preferably a β-N-acetylglucosaminidase, e.g. a dispersin, wherein the polypeptide is selected from the group consisting of:

a) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 1, b) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 2, c) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 3, d) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 4, e) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 5, f) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 6, g) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 7, h) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 8, i) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 9, j) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 10, k) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 11, l) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 12, m) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 13, n) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 14, o) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 15, p) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 16, q) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 17, r) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 18, and wherein the polypeptide cleaves β-substituted N-acetyl glucosaminide, s) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 19, and wherein the polypeptide cleaves β-substituted N-acetyl glucosaminide, t) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 20, and wherein the polypeptide cleaves β-substituted N-acetyl glucosaminide, u) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 21, and wherein the polypeptide cleaves β-substituted N-acetyl glucosaminide, v) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 22, and wherein the polypeptide cleaves β-substituted N-acetyl glucosaminide, and w) a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 23 and wherein the polypeptide cleaves β-substituted N-acetyl glucosaminide.

A polypeptide having hexosaminidase activity may be obtained from microorganisms of any genus. Preferably the hexosaminidase or the β-N-acetylglucosaminidase targeting poly-β-1,6-N-acetylglucosamine e.g. a dispersin, is obtained from *Terribacillus, Curtobacterium, Aggregatibacter, Haemophllus, Actinobacillus, Lactobacillus* or *Staphylococcus*, preferably *Terribacillus* or *Lactobacillus. Alternatively, it may e.g. be obtained from Neisseria, Otariodibacter, Lactococcus, Frigoribacterium, Basfia, Weissella, Macrococcus* or *Leuconostoc*.

In another embodiment, the polypeptide is an *Aggregatibacter* polypeptide, e.g., a polypeptide obtained from *Aggregatibacter actinomycetemcomitans*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 1 and is obtained from *Aggregatibacter*, preferably *Aggregatibacter actinomycetemcomitans*.

In another embodiment, the polypeptide is a *Haemophilus* polypeptide, e.g., a polypeptide obtained from *Haemophilus sputorum*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 2 and is obtained from *Haemophilus*, preferably *Haemophilus sputorum*.

In another embodiment, the polypeptide is an *Actinobacillus* polypeptide, e.g., a polypeptide obtained from *Actinobacillus suis*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 3 and is obtained from *Actinobacillus*, preferably *Actinobacillus suis*.

In another embodiment, the polypeptide is an *Actinobacillus* polypeptide, e.g., a polypeptide obtained from *Actinobacillus capsulatus* DSM 19761. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 4 and is obtained from *Actinobacillus*, preferably *Actinobacillus capsulatus* DSM 19761.

In another embodiment, the polypeptide is an *Actinobacillus* polypeptide, e.g., a polypeptide obtained from *Actinobacillus equuli* subsp. *equuli*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 5 and is obtained from *Actinobacillus*, preferably *Actinobacillus equuli* subsp. *equuli*.

In another embodiment, the polypeptide is an *Aggregatibacter* polypeptide, e.g., a polypeptide obtained from *Aggregatibacter actinomycetemcomitans*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 6 and is obtained from *Aggregatibacter*, preferably *Aggregatibacter actinomycetemcomitans*.

In another embodiment, the polypeptide is an *Aggregatibacter* polypeptide, e.g., a polypeptide obtained from *Aggregatibacter actinomycetemcomitans*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 7 and is obtained from *Aggregatibacter*, preferably *Aggregatibacter actinomycetemcomitans*.

In another embodiment, the polypeptide is an *Actinobacillus* polypeptide, e.g., a polypeptide obtained from *Actinobacillus pleuropneumoniae*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 8 and is obtained from *Actinobacillus*, preferably *Actinobacillus pleuropneumoniae*.

In another embodiment, the polypeptide is a *Curtobacterium* polypeptide, e.g., a polypeptide obtained from *Curtobacterium oceanosedimentum*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 9 and is obtained from *Curtobacterium*, preferably *Curtobacterium oceanosedimentum*.

In another embodiment, the polypeptide is a *Curtobacterium* polypeptide, e.g., a polypeptide obtained from *Curtobacterium flaccumfaciens*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 10 and is obtained from *Curtobacterium*, preferably *Curtobacterium flaccumfaciens*.

In another embodiment, the polypeptide is a *Curtobacterium* polypeptide, e.g., a polypeptide obtained from *Curtobacterium luteum*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 11 and is obtained from *Curtobacterium*, preferably *Curtobacterium luteum*.

In another embodiment, the polypeptide is a *Curtobacterium* polypeptide, e.g., a polypeptide obtained from *Curtobacterium oceanosedimentum*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 12 and is obtained from *Curtobacterium*, preferably *Curtobacterium oceanosedimentum*.

In another embodiment, the polypeptide is a *Curtobacterium* polypeptide, e.g., a polypeptide obtained from *Curtobacterium* leaf154. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 13 and is obtained from *Curtobacterium*, preferably *Curtobacterium* leaf154.

In another embodiment, the polypeptide having hexosaminidase activity is a *Terribacillus* polypeptide, e.g., a polypeptide obtained from *Terribacillus saccharophilus*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 14 and is obtained from *Terribacillus*, preferably *Terribacillus saccharophilus*.

In another embodiment, the polypeptide is a *Terribacillus* polypeptide, e.g., a polypeptide obtained from *Terribacillus goriensis*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 15 and is obtained from *Terribacillus*, preferably *Terribacillus goriensis*.

In another embodiment, the polypeptide is a *Terribacillus* polypeptide, e.g., a polypeptide obtained from *Terribacillus saccharophilus*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 16 and is obtained from *Terribacillus*, preferably *Terribacillus saccharophilus*.

In another embodiment, the polypeptide is a *Terribacillus* polypeptide, e.g., a polypeptide obtained from *Terribacillus saccharophilus*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 17 and is obtained from *Terribacillus*, preferably *Terribacillus saccharophilus*.

In another embodiment, the polypeptide is a *Terribacillus* polypeptide, e.g., a polypeptide obtained from *Terribacillus saccharophilus*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 18 and is obtained from *Terribacillus*, preferably *Terribacillus saccharophilus*.

In another embodiment, the polypeptide is a *Lactobacillus* polypeptide, e.g., a polypeptide obtained from *Lactobacillus paraplantarum*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 19 and is obtained from *Lactobacillus*, preferably *Lactobacillus paraplantarum*.

In another embodiment, the polypeptide is a *Lactobacillus* polypeptide, e.g., a polypeptide obtained from *Lactobacillus apinorum*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 20 and is obtained from *Lactobacillus*, preferably *Lactobacillus apinorum*.

In another embodiment, the polypeptide is a *Lactobacillus* polypeptide, e.g., a polypeptide obtained from *Lactobacillus paraplantarum*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 21 and is obtained from *Lactobacillus*, preferably *Lactobacillus paraplantarum*.

In another embodiment, the polypeptide is a *Staphylococcus* polypeptide, e.g., a polypeptide obtained from *Staphylococcus cohnii*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 22 and is obtained from *Staphylococcus*, preferably *Staphylococcus cohnii*.

In another embodiment, the polypeptide is a *Staphylococcus* polypeptide, e.g., a polypeptide obtained from *Staphylococcus fleurettii*. In a preferred embodiment, the polypeptide is a polypeptide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to SEQ ID NO: 23 and is obtained from *Staphylococcus*, preferably *Staphylococcus fleurettii*.

The polypeptides useful in the present invention belong to the Glycoside Hydrolase family 20 (GH20, www.cazy.org). This family includes dispersins such as Dispersin B (DspB) which are β-N-acetylglucosaminidases belonging to the Glycoside Hydrolase 20 family.

The hexosaminidase can be included in the cleaning composition of the present invention at a level of from 0.01 to 1000 ppm, from 1 ppm to 1000 ppm, from 10 ppm to 1000 ppm, from 50 ppm to 1000 ppm, from 100 ppm to 1000 ppm, from 150 ppm to 1000 ppm, from 200 ppm to 1000 ppm, from 250 ppm to 1000 ppm, from 250 ppm to 750 ppm, from 250 ppm to 500 ppm.

The hexosaminidase can be included in the wash liquor solution of the present invention at a level of from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, from 0.1 ppm to 10 ppm, from 0.2 ppm to 10 ppm, from 0.5 ppm to 5 ppm.

The dispersins above may be combined with any of the proteases below to form a blend to be added to a composition according to the invention. In various embodiments, the dispersin is a polypeptide having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide shown in SEQ ID NO: 17.

Polypeptides Having Protease Activity

Suitable proteases may be of any origin, but are preferably of bacterial or fungal origin, optionally in the form of protein engineered or chemically modified mutants. The protease may be an alkaline protease, such as a serine protease or a metalloprotease. A serine protease may for example be of the S1 family, such as trypsin, or the S8 family such as a subtilisin. A metalloprotease may for example be a thermolysin, e.g. from the M4 family, or another metalloprotease such as those from the M5, M7 or M8 families.

The term "subtilases" refers to a sub-group of serine proteases according to Siezen et al., *Protein Eng.* 4 (1991) 719-737 and Siezen et al., *Protein Sci.* 6 (1997) 501-523. Serine proteases are a subgroup of proteases characterized by having a serine in the active site, which forms a covalent adduct with the substrate. The subtilases may be divided into six subdivisions, the Subtilisin family, the Thermitase family, the Proteinase K family, the Lantibiotic peptidase family, the Kexin family and the Pyrolysin family.

Although proteases suitable for detergent use may be obtained from a variety of organisms, including fungi such as *Aspergillus*, detergent proteases have generally been obtained from bacteria and in particular from *Bacillus*. Examples of *Bacillus* species from which subtilases have been derived include *Bacillus lentus, Bacillus alkalophilus, Bacillus subtilis, Bacillus amyloliquefaciens, Bacillus licheniformis, Bacillus pumilus* and *Bacillus gibsonii*. Particular subtilisins include subtilisin lentus, subtilisin Novo, subtilisin Carlsberg, subtilisin BPN', subtilisin 309, subtilisin 147 and subtilisin 168 and e.g. protease PD138 (described in WO 93/18140). Other useful proteases are e.g. those described in WO 01/16285 and WO 02/16547.

Examples of trypsin-like proteases include the *Fusarium* protease described in WO 94/25583 and WO 2005/040372, and the chymotrypsin proteases derived from Cellumonas described in WO 2005/052161 and WO 2005/052146.

Examples of metalloproteases include the neutral metalloproteases described in WO 2007/044993 such as those derived from *Bacillus amyloliquefaciens*, as well as e.g. the metalloproteases described in WO 2015/158723 and WO 2016/075078.

Examples of useful proteases are the variants described in WO 89/06279 WO 92/19729, WO 96/34946, WO 98/20115, WO 98/20116, WO 99/11768, WO 01/44452, WO 03/006602, WO 2004/003186, WO 2004/041979, WO 2007/006305, WO 2011/036263, WO 2014/207227, WO 2016/087617 and WO 2016/174234. Preferred protease variants may, for example, comprise one or more of the mutations selected from the group consisting of: S3T, V4I, S9R, S9E, A15T, S24G, S24R, K27R, N42R, S55P, G59E, G59D, N60D, N60E, V66A, N74D, S85R, A96S, S97G, S97D, S97A, S97SD, S99E, S99D, S99G, S99M, S99N, S99R, S99H, S101A, V102I, V102Y, V102N, S104A, G116V, G116R, H118D, H118N, A120S, S126L, P127Q, S128A, S154D, A156E, G157D, G157P, S158E, Y161A, R164S, Q176E, N179E, S182E, Q185N, A188P, G189E, V193M, N198D, V199I, Q200L, Y203W, S206G, L211Q, L211D, N212D, N212S, M216S, A226V, K229L, Q230H, Q239R, N246K, S253D, N255W, N255D, N255E, L256E, L256D T268A and R269H, wherein position numbers correspond to positions of the *Bacillus lentus* protease shown in SEQ ID NO: 1 of WO 2016/001449. Protease variants having one or more of these mutations are preferably variants of the *Bacillus lentus* protease (Savinase®, also known as subtilisin 309) shown in SEQ ID NO: 1 of WO 2016/001449 or of the *Bacillus amyloliquefaciens* protease (BPN') shown in SEQ ID NO: 2 of WO 2016/001449. Such protease variants preferably have at least 80% sequence identity to SEQ ID NO: 1 or to SEQ ID NO: 2 of WO 2016/001449.

Another protease of interest is the alkaline protease from *Bacillus lentus* DSM 5483, as described for example in WO 91/02792, and variants thereof which are described for example in WO 92/21760, WO 95/23221, EP 1921147, EP 1921148 and WO 2016/096711.

The protease may alternatively be a variant of the TY145 protease having SEQ ID NO: 1 of WO 2004/067737, for example a variant comprising a substitution at one or more positions corresponding to positions 27, 109, 111, 171, 173, 174, 175, 180, 182, 184, 198, 199 and 297 of SEQ ID NO: 1 of WO 2004/067737, wherein said protease variant has a sequence identity of at least 75% but less than 100% to SEQ ID NO: 1 of WO 2004/067737. TY145 variants of interest are described in e.g. WO 2015/014790, WO 2015/014803, WO 2015/014804, WO 2016/097350, WO 2016/097352, WO 2016/097357 and WO 2016/097354.

In one embodiment, the protease useful in the present invention is selected from the group consisting of:

i) a protease variant of a protease parent, wherein the protease variant comprises one or more alteration(s) compared to a protease shown in SEQ ID NO: 24 or SEQ ID NO: 25 in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO: 24 and wherein the protease variant has at least 60%, at least 65%, at least 70%, at least 75% at least 80%, at least 85%, at least 90%, at least 95%, at least 98% but less than 100% sequence identity to SEQ ID NO: 24 or SEQ ID NO: 25;

ii) a protease variant of a protease parent, wherein the protease variant comprises one or more mutation selected from the group consisting of: X3T, X4I, X9R, X9E, X15T, X24G, X24R, X27R, X42R, X55P, X59E, X59D, X60D, X60E, X66A, X74D, X85R, X96S, X97G, X97D, X97A, X97XD, X99E, X99D, X99G, X99M, X99N, X99R, X99H, X101A, X102I, X102Y, X102N, X104A, X116V, X116R, X118D, X118N, X120S, X126L, X127Q, X128A, X154D, X156E, X157D, X157P, X158E, X161A, X164S, X176E, X179E, X182E, X185N, X188P, X189E, X193M, X198D, X1991, X203W, X206G, X211Q, X211D, X212D, X212S, X216S, X226V, X229L, X230H, X239R, X246K, X255W, X255D, X255E, X256E, X256D X268A and X269H, wherein the positions correspond to the positions of the protease shown in SEQ ID NO: 24, wherein the protease variant has at least 60%, at least 65%, at least 70%, at least 75% at least 80%, at least 85%, at least 90%, at least 95%, at least 98% but less than 100% sequence identity to SEQ ID NO: 24 or SEQ ID NO: 25;

iii) a protease comprising a substitution at one or more positions corresponding to positions 171, 173, 175, 179, or 180 of SEQ ID NO: 26, compared to the protease shown in SEQ ID NO: 26, wherein the protease variant has a sequence identity of at least 60%, at least 65%, at least 70%, at least 75% at least 80%, at least 85%, at least 90%, at least 95%, at least 98% but less than 100% sequence identity to the amino acid sequence 1 to 311 of SEQ ID NO: 26, iv) a protease comprising the amino acid sequence shown in SEQ ID NO: 24, 25, 26 or a protease having at least 60%, at least 65%, at least 70%, at least 75% at least 80%, at least 85%, at least 90%, at least 95%, at least 98% or 100% sequence identity to; the polypeptide comprising amino acids 1-269 of SEQ ID NO: 24, the polypeptide comprising amino acids 1-311 of SEQ ID NO: 26 the polypeptide comprising amino acids 1-275 of SEQ ID NO: 25;

v) a protease comprising the amino acid sequence shown in SEQ ID NO: 27, SEQ ID NO: 28, SEQ ID NO: 29, SEQ ID NO: 30, SEQ ID NO: 31 or a protease having at least 60%, at least 65%, at least 70%, at least 75% at least 80%, at least 85%, at least 90%, at least 95%, at least 98% or preferably 100% sequence identity hereto;

vi) one or more of the following protease variants selected from the group consisting of:

SEQ ID NO: 24+T22R+S99G+S101A+V102I+A226V+Q239R,

SEQ ID NO: 25+S24G+S53G+S78N+S101N+G128A+Y217Q,

SEQ ID NO: 25+S24G+S53G+S78N+S101N+G128S+Y217Q,

SEQ ID NO: 24+S9E+N42R+N74D+V199I+Q200L+Y203W+S253D+N255W+L256E,

SEQ ID NO: 24+S9E+N42R+N74D+H118V+Q176E+A188P+V199I+Q200L Y203W+S250D+S253D+N255W+L256E

SEQ ID NO: 24+S9E+N42R+N74D+Q176E+A188P+V199I+Q200L+Y203W S250D+S253D+N255W+L256E

SEQ ID NO: 24+S3V+N74D+H118V+Q176E+N179E+S182E+V199I+Q200L Y203W+S210V+S250D+S253D+N255W+L256E

SEQ ID NO: 24+T22A+N60D+S99G+S101A+V102I+N114L+G157D+S182D+T207A+A226V+Q239R+N242D+E265F,

SEQ ID NO: 24+S9E+N42R+N74D+H118V+Q176E+A188P+V199I+Q200L+Y203W+S250D+S253D+N255W+L256E,

SEQ ID NO: 24+S9E+N42R+N74D+Q176E+A188P+V199I+Q200L+Y203W+S250D+S253D+N255W+L256E,

SEQ ID NO: 24+S9E+N42R+N74D+H118V+Q176E+A188P+V199I+Q200L+Y203W+S250D+N255W+L256E+*269aH+*269bH,

SEQ ID NO: 24+S3V+N74D+H118V+Q176E+N179E+S182E+V199I+Q200L+Y203W+S210V+S250D+N255W+L256E,

SEQ ID NO: 24+S9E+N74D+G113W+G157P+Q176E+V199I+Q200L+Y203W+S250D+T254E+N255W+L256E,

SEQ ID NO: 24+S3V+S9R+N74D+H118V+Q176E+N179E+S182E+V199I+Q200L+Y203W+S212V+S250D+N255W+L256E,

SEQ ID NO: 24+S99E, and

SEQ ID NO: 25+L217D.

Substitutions indicated with an "X" preceding a position number means that any original natural amino acid in a parent protease may be substituted at the corresponding indicated position in the parent protease. For example, "X3T" means that any amino acid residue at position 3 of a parent protease other than T is substituted with T. If the protease in this case already comprises threonine in position 3, it will be apparent to the skilled person that there will be no replacement.

The term "corresponding to" reflects the numbering system used and that various starting proteases (parent proteases) may have different lengths. Thus, a given starting protease may be aligned with e.g. SEQ ID NO: 24 and the position corresponding to e.g. position 3 is determined.

Indication of a SEQ ID NO+mutation(s) is to be understood as a variant of a parent protease comprising the specified mutations compared to the relevant parent sequence, e.g. SEQ ID NO: 25+L217D is a variant of a protease shown in SEQ ID NO: 25, which compared to SEQ ID NO: 25 comprises the mutation L217D (substitution of leucine in position 217 of SEQ ID NO: 25 with aspartic acid).

Examples of preferred proteases include:

(a) variants of SEQ ID NO: 1 of WO 2016/001449 comprising two or more substitutions selected from the group consisting of S9E, N43R, N76D, Q206L, Y209W, S259D and L262E, for example a variant with the substitutions S9E, N43R, N76D, V2051, Q206L, Y209W, S259D, N261W and L262E, or with the substitutions S9E, N43R, N76D, N185E, S188E, Q191N, A194P, Q206L, Y209W, S259D and L262E, wherein position numbers are based on the numbering of SEQ ID NO: 2 of WO 2016/001449;

(b) a variant of the polypeptide of SEQ ID NO: 1 of WO 2016/001449 with the mutation S99SE, wherein position numbers are based on the numbering of SEQ ID NO: 2 of WO 2016/001449;

(c) a variant of the polypeptide of SEQ ID NO: 1 of WO 2016/001449 with the mutation S99AD, wherein position numbers are based on the numbering of SEQ ID NO: 2 of WO 2016/001449;

(d) a variant of the polypeptide of SEQ ID NO: 1 of WO 2016/001449 with the substitutions Y167A+R170S+A194P, wherein position numbers are based on the numbering of SEQ ID NO: 2 of WO 2016/001449;

(e) a variant of the polypeptide of SEQ ID NO: 1 of WO 2016/001449 with the substitutions S9R+A15T+V68A+N218D+Q245R, wherein position numbers are based on the numbering of SEQ ID NO: 2 of WO 2016/001449;

(f) a variant of the polypeptide of SEQ ID NO: 1 of WO 2016/001449 with the substitutions S9R+A15T+G61E+V68A+A194P+V2051+Q245R+N261D, wherein position numbers are based on the numbering of SEQ ID NO: 2 of WO 2016/001449;

(g) a variant of the polypeptide of SEQ ID NO: 1 of WO 2016/001449 with the substitutions S99D+S101R/E+S103A+V1041+G160S; for example a variant of SEQ ID NO: 1 of WO 2016/001449 with the substitutions S3T+V4I+S99D+S101E+S103A+V1041+G160S+V2051, wherein position numbers are based on the numbering of SEQ ID NO: 2 of WO 2016/001449;

(h) a variant of the polypeptide of SEQ ID NO: 2 of WO 2016/001449 with the substitutions S24G+S53G+S78N+S101N+G128A/S+Y217Q, wherein position numbers are based on the numbering of SEQ ID NO: 2 of WO 2016/001449;

(i) the polypeptide disclosed in GENESEQP under accession number BER84782, corresponding to SEQ ID NO: 302 in WO 2017/210295;

(j) a variant of the polypeptide of SEQ ID NO: 1 of WO 2016/001449 with the substitutions S99D+S101E+S103A+V1041+S156D+G160S+L262E, wherein position numbers are based on the numbering of SEQ ID NO: 2 of WO 2016/001449;

(k) a variant of the polypeptide of SEQ ID NO: 1 of WO 2016/001449 with the substitutions S9R+A15T+G61E+V68A+N76D+S99G+N218D+Q245R, wherein position numbers are based on the numbering of SEQ ID NO: 2 of WO 2016/001449;

(l) a variant of the polypeptide of SEQ ID NO: 1 of WO 2016/001449 with the substitutions V68A+S106A, wherein position numbers are based on the numbering of SEQ ID NO: 2 of WO 2016/001449;

(m) a variant of the polypeptide of SEQ ID NO: 1 of WO 2004/067737 with the substitutions S27K+N109K+S111E+S171E+S173P+G174K+S175P+F180Y+G182A+L184F+Q198E+N199+T297P, wherein position numbers are based on the numbering of SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase™ Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Blaze Evity® 200T, Neutrase®, Everlase®, Esperase®, Progress® Uno, Progress® In and Progress® Excel (Novozymes A/S), those sold under the tradename Maxatase™, Maxacal™, Maxapem®, Purafect® Ox, Purafect® OxP, Puramax®, FN2™, FN3™, FN4$^{ex}$™, Excellase®, Excellenz™ P1000, Excellenz™ P1250, Eraser™, Preferenz® P100, Purafect Prime, Preferenz P110™, Effectenz P1000™, Purafect®, Effectenz P1050™, Purafect® Ox, Effectenz™ P2000, Purafast™, Properase®, Opticlean™ and Optimase® (Danisco/DuPont), BLAP (sequence shown in FIG. 29 of U.S. Pat. No. 5,352,604) and variants hereof (Henkel AG), and KAP (*Bacillus alkalophilus* subtilisin) from Kao.

Compositions

The invention relates to cleaning compositions, as defined herein, comprising a dispersin and a protease as per the appended claims.

One embodiment of the invention relates to a cleaning composition, as defined herein, comprising a dispersin, a protease and at least one cleaning component. The protease may be any of the proteases mentioned under the heading "Polypeptides having protease activity". Preferably, the protease is a subtilase and even more preferably the protease belongs to the subtilisin sub group of subtilases. One embodiment relates to a cleaning composition comprising a dispersin and a protease, wherein the protease is a subtilase, preferably a subtilisin.

The most relevant cleaning proteases are those obtainable from *Bacillus*, as such proteases have shown to be active at high pH and to effectively remove protease stains. It is contemplated that the subtilisin proteases of the genus *Bacillus* may act synergistically with the dispersin in reduction and removal of biofilm or components hereof. Biofilm is a complex structure comprising e.g. protein and PNAG, where the target substrate e.g. the PNAG may be embedded in the biofilm structure, and it is believed that when the dispersins and proteases are acting together on respective parts of the biofilm structure, the PNAG and protein components may be more effectively removed. It is thus advantageous to formulate dispersins with proteases in cleaning compositions, as defined herein, e.g. for deep cleaning.

As mentioned above the most relevant proteases used in the cleaning industry today are obtained from *Bacillus*, e.g. *Bacillus lentus* and *Bacillus amyloliquefaciens*. One embodiment of the invention relates to a cleaning composition, as defined herein, comprising a dispersin and a protease, wherein the protease is obtained from *Bacillus*, preferably from *Bacillus lentus, Bacillus amyloliquefaciens, Bacillus licheniformis, Bacillus pumilus, Bacillus halodurans* or *Bacillus subtilis.*

Proteases suitable for combining with the dispersins in the cleaning composition of the invention are preferably proteases suitable for cleaning and which have high stain removal capacity under the relative cleaning conditions, e.g. in the presence of surfactants, builders or other cleaning components.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25 or SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 27.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 28.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 29.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 30.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 31.

One embodiment relates to a cleaning composition, a defined herein, comprising a dispersin and a protease, wherein the protease is obtained from *Bacillus*, preferably from *Bacillus lentus, Bacillus amyloliquefaciens, Bacillus licheniformis, Bacillus pumilus, Bacillus halodurans* or *Bacillus subtilis*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25 or SEQ ID NO: 26.

One embodiment relates to a cleaning composition, as defined herein, comprising a dispersin and a protease, wherein the protease is obtained from *Bacillus*, preferably from *Bacillus lentus*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24.

One embodiment relates to a cleaning composition, as defined herein, comprising a dispersin and a protease, wherein the protease is obtained from *Bacillus*, preferably from *Bacillus amyloliquefaciens*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25.

One embodiment relates to a cleaning composition, as defined herein, comprising a dispersin and a protease, wherein the protease is obtained from *Bacillus* sp and has at least 60%, at least 65%, at least 70%, at least 75%, at least 80%, at least 85%, at least 90%, at least 95%, at least 98% or 100% sequence identity to the amino acid sequence shown in SEQ ID NO: 26.

Thus, as mentioned the protease should be compatible with cleaning components and likewise, the dispersins to be formulated together with the protease or to be used together with the protease should also be compatible with cleaning components. Dispersins are at present not standard ingredients in cleaning compositions. However, dispersins suitable for use in cleaning compositions have been identified, e.g. in WO 2017/186936, WO 2017/186937 and WO 2017/186943. Enzymes such as dispersins should not only be compatible with the cleaning components, the dispersins should also be compatible with other enzymes which may be present in a typical cleaning composition. It is well known that proteases may negatively influence the performance of other enzymes as the protease may degrade these enzymes (being themselves proteins). Surprisingly, it has been found that proteases and dispersins not only are compatible but can even act synergistically in respect of biofilm stain reduction and removal e.g. in deep cleaning.

Particularly useful dispersins may be those of microbial origin. One embodiment of the invention relates to a cleaning composition, as defined herein, comprising a dispersin and a protease, wherein the dispersin is microbial, preferably obtained from bacteria or fungi. In one embodiment, the cleaning composition, as defined herein, comprises a dispersin from bacteria. One embodiment of the invention relates to a cleaning composition, as defined herein, comprising a dispersin and a protease, wherein the dispersin is obtained from *Terribacillus, Curtobacterium, Aggregatibacter, Haemophilus, Actinobacillus, Lactobacillus* or *Staphylococcus* preferably *Terribacillus* or *Lactobacillus.*

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22.

One embodiment of the invention relates to a cleaning composition, as defined herein, comprising a dispersin and a protease, wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23.

One embodiment relates to a cleaning composition, as defined herein, comprising a *Terribacillus* dispersin and a protease, wherein the protease is obtained from *Bacillus*, preferably from *Bacillus lentus*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24.

One embodiment relates to a cleaning composition, as defined herein, comprising a *Terribacillus* dispersin and a protease, wherein the protease is obtained from *Bacillus*, preferably from *Bacillus amyloliquefaciens*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25.

One embodiment relates to a cleaning composition, as defined herein, comprising a *Terribacillus* dispersin and a protease, wherein the protease is obtained from *Bacillus* sp and has at least 60%, at least 65%, at least 70%, at least 75%, at least 80%, at least 85%, at least 90%, at least 95%, at least 98% or 100% sequence identity to the amino acid sequence shown in SEQ ID NO: 26.

One embodiment relates to a cleaning composition, as defined herein, comprising a *Terribacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 27.

One embodiment relates to a cleaning composition, as defined herein, comprising a *Terribacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 28.

One embodiment relates to a cleaning composition, as defined herein, comprising a *Terribacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 29.

One embodiment relates to a cleaning composition, as defined herein, comprising a *Terribacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 30.

One embodiment relates to a cleaning composition, as defined herein, comprising a *Terribacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 31.

One embodiment relates to a cleaning composition, as defined herein, comprising a *Curtobacterium* dispersin and a protease, wherein the protease is obtained from *Bacillus*, preferably from *Bacillus lentus*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24.

One embodiment relates to a cleaning composition, as defined herein, comprising a *Curtobacterium* dispersin and a protease, wherein the protease is obtained from *Bacillus*, preferably from *Bacillus amyloliquefaciens*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25.

One embodiment relates to a cleaning composition, as defined herein, comprising a *Curtobacterium* dispersin and a protease, wherein the protease is obtained from *Bacillus* sp and has at least 60%, at least 65%, at least 70%, at least 75%, at least 80%, at least 85%, at least 90%, at least 95%, at least 98% or 100% sequence identity to the amino acid sequence shown in SEQ ID NO: 26.

One embodiment relates to a cleaning composition, as defined herein, comprising a *Curtobacterium* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 27.

One embodiment relates to a cleaning composition, as defined herein, comprising a *Curtobacterium* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 28.

One embodiment relates to a cleaning composition, as defined herein, comprising a *Curtobacterium* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 29.

One embodiment relates to a cleaning composition, as defined herein, comprising a *Curtobacterium* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 30.

One embodiment relates to a cleaning composition, as defined herein, comprising a *Curtobacterium* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 31.

One embodiment relates to a cleaning composition, as defined herein, comprising a *Aggregatibacter* dispersin and a protease, wherein the protease is obtained from *Bacillus* preferably from *Bacillus lentus* and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24.

One embodiment relates to a cleaning composition, as defined herein, comprising a *Aggregatibacter* dispersin and a protease, wherein the protease is obtained from *Bacillus* preferably from *Bacillus amyloliquefaciens* and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25.

One embodiment relates to a cleaning composition, as defined herein, comprising a *Aggregatibacter* dispersin and a protease, wherein the protease is obtained from *Bacillus* preferably from *Bacillus* sp and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26.

One embodiment relates to a cleaning composition, as defined herein, comprising a *Aggregatibacter* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 27.

One embodiment relates to a cleaning composition, as defined herein, comprising a *Aggregatibacter* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 28.

One embodiment relates to a cleaning composition, as defined herein, comprising a *Aggregatibacter* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 29.

One embodiment relates to a cleaning composition, as defined herein, comprising a *Aggregatibacter* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 30.

One embodiment relates to a cleaning composition, as defined herein, comprising a *Aggregatibacter* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 31.

One embodiment relates to a cleaning composition, as defined herein, comprising a *Haemophilus* dispersin and a protease, wherein the protease is obtained from *Bacillus*, preferably from *Bacillus lentus*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24.

One embodiment relates to a cleaning composition, as defined herein, comprising a *Haemophilus* dispersin and a protease, wherein the protease is obtained from *Bacillus*, preferably from *Bacillus amyloliquefaciens*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25.

One embodiment relates to a cleaning composition, as defined herein, comprising a *Haemophilus* dispersin and a protease, wherein the protease is obtained from *Bacillus* sp and has at least 60%, at least 65%, at least 70%, at least 75%, at least 80%, at least 85%, at least 90%, at least 95%, at least 98% or 100% sequence identity to the amino acid sequence shown in SEQ ID NO: 26.

One embodiment relates to a cleaning composition, as defined herein, comprising a *Haemophilus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 27.

One embodiment relates to a cleaning composition, as defined herein, comprising a *Haemophilus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 28.

One embodiment relates to a cleaning composition, as defined herein, comprising a *Haemophilus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 29.

One embodiment relates to a cleaning composition, as defined herein, comprising a *Haemophilus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 30.

One embodiment relates to a cleaning composition, as defined herein, comprising a *Haemophilus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 31.

One embodiment relates to a cleaning composition, as defined herein, comprising a *Actinobacillus* dispersin and a protease, wherein the protease is obtained from *Bacillus*, preferably from *Bacillus lentus*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24.

One embodiment relates to a cleaning composition, as defined herein, comprising a *Actinobacillus* dispersin and a protease, wherein the protease is obtained from *Bacillus*, preferably from *Bacillus amyloliquefaciens*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25.

One embodiment relates to a cleaning composition, as defined herein, comprising a *Actinobacillus* dispersin and a protease, wherein the protease is obtained from *Bacillus* sp and has at least 60%, at least 65%, at least 70%, at least 75%, at least 80%, at least 85%, at least 90%, at least 95%, at least 98% or 100% sequence identity to the amino acid sequence shown in SEQ ID NO: 26.

One embodiment relates to a cleaning composition, as defined herein, comprising a *Actinobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 27.

One embodiment relates to a cleaning composition, as defined herein, comprising a *Actinobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 28.

One embodiment relates to a cleaning composition, as defined herein, comprising a *Actinobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 29.

One embodiment relates to a cleaning composition, as defined herein, comprising a *Actinobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 30.

One embodiment relates to a cleaning composition, as defined herein, comprising a *Actinobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 31.

One embodiment relates to a cleaning composition, as defined herein, comprising a *Lactobacillus* dispersin and a protease, wherein the protease is obtained from *Bacillus*, preferably from *Bacillus lentus*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24.

One embodiment relates to a cleaning composition, as defined herein, comprising a *Lactobacillus* dispersin and a protease, wherein the protease is obtained from *Bacillus*, preferably from *Bacillus amyloliquefaciens*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25.

One embodiment relates to a cleaning composition, as defined herein, comprising a *Lactobacillus* dispersin and a protease, wherein the protease is obtained from *Bacillus* sp and has at least 60%, at least 65%, at least 70%, at least 75%, at least 80%, at least 85%, at least 90%, at least 95%, at least 98% or 100% sequence identity to the amino acid sequence shown in SEQ ID NO: 26.

One embodiment relates to a cleaning composition, as defined herein, comprising a *Lactobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 27.

One embodiment relates to a cleaning composition, as defined herein, comprising a *Lactobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 28.

One embodiment relates to a cleaning composition, as defined herein, comprising a *Lactobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 29.

One embodiment relates to a cleaning composition, as defined herein, comprising a *Lactobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 30.

One embodiment relates to a cleaning composition, as defined herein, comprising a *Lactobacillus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 31.

One embodiment relates to a cleaning composition, as defined herein, comprising a *Staphylococcus* dispersin and a protease, wherein the protease is obtained from *Bacillus*, preferably from *Bacillus lentus*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24.

One embodiment relates to a cleaning composition, as defined herein, comprising a *Staphylococcus* dispersin and a protease, wherein the protease is obtained from *Bacillus*, preferably from *Bacillus amyloliquefaciens*, and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25.

One embodiment relates to a cleaning composition, as defined herein, comprising a *Staphylococcus* dispersin and a protease, wherein the protease is obtained from *Bacillus* sp and wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26.

One embodiment relates to a cleaning composition, as defined herein, comprising a *Staphylococcus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 27.

One embodiment relates to a cleaning composition, as defined herein, comprising a *Staphylococcus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 28.

One embodiment relates to a cleaning composition, as defined herein, comprising a *Staphylococcus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 29.

One embodiment relates to a cleaning composition, as defined herein, comprising a *Staphylococcus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 30.

One embodiment relates to a cleaning composition, as defined herein, comprising a *Staphylococcus* dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 31

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1. One embodiment relates to a cleaning composition, as defined herein, comprising a dispersin and a protease, wherein the dispersin comprises or consists of the polypeptide comprising the amino acid sequence shown in SEQ ID NO: 1 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1. One embodiment relates to a cleaning composition, as defined herein, comprising a dispersin and a protease, wherein the dispersin comprises or consists of the polypeptide comprising the amino acid sequence shown in SEQ ID NO: 1 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1. One embodiment relates to a cleaning composition, as defined herein, comprising a dispersin and a protease, wherein the dispersin comprises or consists of the polypeptide comprising the amino acid sequence shown in SEQ ID NO: 1 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2. One embodiment relates to a cleaning composition, as defined herein, comprising a dispersin and a protease, wherein the dispersin comprises or consists of the polypeptide comprising the amino acid sequence shown in SEQ ID NO: 2 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2. One embodiment relates to a cleaning composition, as defined herein, comprising a dispersin and a protease, wherein the dispersin comprises or consists of the polypeptide comprising the amino acid sequence shown in SEQ ID NO: 2 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2. One embodiment relates to a cleaning composition, as defined herein, comprising a dispersin and a protease, wherein the dispersin comprises or consists of the polypeptide comprising the amino acid sequence shown in SEQ ID NO: 2 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3. One embodiment relates to a cleaning composition, as defined herein, comprising a dispersin and a protease, wherein the dispersin comprises or consists of the polypeptide comprising the amino acid sequence shown in SEQ ID NO: 3 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3. One embodiment relates to a cleaning composition, as defined herein, comprising a dispersin and a protease, wherein the dispersin comprises or consists of the polypeptide comprising the amino acid sequence shown in SEQ ID NO: 3 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3. One embodiment relates to a cleaning composition, as defined herein, comprising a dispersin and a protease, wherein the dispersin comprises or consists of the polypeptide comprising the amino acid sequence shown in SEQ ID NO: 3 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4. One embodiment relates to a cleaning composition, as defined herein, comprising a dispersin and a protease, wherein the dispersin comprises or consists of the polypeptide comprising the amino acid sequence shown in SEQ ID NO: 4 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4. One embodiment relates to a cleaning composition, as defined herein, comprising a dispersin and a protease, wherein the dispersin comprises or consists of the polypeptide comprising the amino acid sequence shown in SEQ ID NO: 4 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4. One embodiment relates to a cleaning composition, as defined herein, comprising a dispersin and a protease, wherein the dispersin comprises or consists of the polypeptide comprising the amino acid sequence shown in SEQ ID NO: 4 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5. One embodiment relates to a cleaning composition, as defined herein, comprising a dispersin and a protease, wherein the dispersin comprises or consists of the polypeptide comprising the amino acid sequence shown in SEQ ID NO: 5 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5. One embodiment relates to a cleaning composition, as defined herein, comprising a dispersin and a protease, wherein the dispersin comprises or consists of the polypeptide comprising the amino acid sequence shown in SEQ ID NO: 5 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5. One embodiment relates to a cleaning composition, as defined herein, comprising a dispersin and a protease, wherein the dispersin comprises or consists of the polypeptide comprising the amino acid sequence shown in SEQ ID NO: 5 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6. One embodiment relates to a cleaning composition, as defined herein, comprising a dispersin and a protease, wherein the dispersin comprises or consists of the polypeptide comprising the amino acid sequence shown in SEQ ID NO: 6 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6. One embodiment relates to a cleaning composition, as defined herein, comprising a dispersin and a protease, wherein the dispersin comprises or consists of the polypeptide comprising the amino acid sequence shown in SEQ ID NO: 6 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6. One embodiment relates to a cleaning composition, as defined herein, comprising a dispersin and a protease, wherein the dispersin comprises or consists of the polypeptide comprising the amino acid sequence shown in SEQ ID NO: 6 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7. One embodiment relates to a cleaning composition, as defined herein, comprising a dispersin and a protease, wherein the dispersin comprises or consists of the polypeptide comprising the amino acid sequence shown in SEQ ID NO: 7 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7. One embodiment relates to a cleaning composition, as defined herein, comprising a dispersin and a protease, wherein the dispersin comprises or consists of the polypeptide comprising the amino acid sequence shown in SEQ ID NO: 7 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7. One embodiment relates to a cleaning composition, as defined herein, comprising a dispersin and a protease, wherein the dispersin comprises or consists of the polypeptide comprising the amino acid sequence shown in SEQ ID NO: 7 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8. One embodiment relates to a cleaning composition, as defined herein, comprising a dispersin and a protease, wherein the dispersin comprises or consists of the polypeptide comprising the amino acid sequence shown in SEQ ID NO: 8 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8. One embodiment relates to a cleaning composition, as defined herein, comprising a dispersin and a protease, wherein the dispersin comprises or consists of the polypeptide comprising the amino acid sequence shown in SEQ ID NO: 8 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8. One embodiment relates to a cleaning composition, as defined herein, comprising a dispersin and a protease, wherein the dispersin comprises or consists of the polypeptide comprising the amino acid sequence shown in SEQ ID NO: 8 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9. One embodiment relates to a cleaning composition, as defined herein, comprising a dispersin and a protease, wherein the dispersin comprises or consists of the polypeptide comprising the amino acid sequence shown in SEQ ID NO: 9 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9. One embodiment relates to a cleaning composition, as defined herein, comprising a dispersin and a protease, wherein the dispersin comprises or consists of the polypeptide comprising the amino acid sequence shown in SEQ ID NO: 9 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9. One embodiment relates to a cleaning composition, as defined herein, comprising a dispersin and a protease, wherein the dispersin comprises or consists of the polypeptide comprising the amino acid sequence shown in SEQ ID NO: 9 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10. One embodiment relates to a cleaning composition, as defined herein, comprising a dispersin and a protease, wherein the dispersin comprises or consists of the polypeptide comprising the amino acid sequence shown in SEQ ID NO: 10 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10. One embodiment relates to a cleaning composition, as defined herein, comprising a dispersin and a protease, wherein the dispersin comprises or consists of the polypeptide comprising the amino acid sequence shown in SEQ ID NO: 10 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10. One embodiment relates to a cleaning composition, as defined herein, comprising a dispersin and a protease, wherein the dispersin comprises or consists of the polypeptide comprising the amino acid sequence shown in SEQ ID NO: 10 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11. One embodiment relates to a cleaning composition, as defined herein, comprising a dispersin and a protease, wherein the dispersin comprises or consists of the polypeptide comprising the amino acid sequence shown in SEQ ID NO: 11 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11. One embodiment relates to a cleaning composition, as defined herein, comprising a dispersin and a protease, wherein the dispersin comprises or consists of the polypeptide comprising the amino acid sequence shown in SEQ ID NO: 11 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11. One embodiment relates to a cleaning composition, as defined herein, comprising a dispersin and a protease, wherein the dispersin comprises or consists of the polypeptide comprising the amino acid sequence shown in SEQ ID NO: 11 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12. One embodiment relates to a cleaning composition, as defined herein, comprising a dispersin and a protease, wherein the dispersin comprises or consists of the polypeptide comprising the amino acid sequence shown in SEQ ID NO: 12 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12. One embodiment relates to a cleaning composition, as defined herein, comprising a dispersin and a protease, wherein the dispersin comprises or consists of the polypeptide comprising the amino acid sequence shown in SEQ ID NO: 12 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12. One embodiment relates to a cleaning composition, as defined herein, comprising a dispersin and a protease, wherein the dispersin comprises or consists of the polypeptide comprising the amino acid sequence shown in SEQ ID NO: 12 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13. One embodiment relates to a cleaning composition, as defined herein, comprising a dispersin and a protease, wherein the dispersin comprises or consists of the polypeptide comprising the amino acid sequence shown in SEQ ID NO: 13 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13. One embodiment relates to a cleaning composition, as defined herein, comprising a dispersin and a protease, wherein the dispersin comprises or consists of the polypeptide comprising the amino acid sequence shown in SEQ ID NO: 13 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13. One embodiment relates to a cleaning composition, as defined herein, comprising a dispersin and a protease, wherein the dispersin comprises or consists of the polypeptide comprising the amino acid sequence shown in SEQ ID NO: 13 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14. One embodiment relates to a cleaning composition, as defined herein, comprising a dispersin and a protease, wherein the dispersin comprises or consists of the polypeptide comprising the amino acid sequence shown in SEQ ID NO: 14 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14. One embodiment relates to a cleaning composition, as defined herein, comprising a dispersin and a protease, wherein the dispersin comprises or consists of the polypeptide comprising the amino acid sequence shown in SEQ ID NO: 14 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14. One embodiment relates to a cleaning composition, as defined herein, comprising a dispersin and a protease, wherein the dispersin comprises or consists of the polypeptide comprising the amino acid sequence shown in SEQ ID NO: 14 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15. One embodiment relates to a cleaning composition, as defined herein, comprising a dispersin and a protease, wherein the dispersin comprises or consists of the polypeptide comprising the amino acid sequence shown in SEQ ID NO: 15 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15. One embodiment relates to a cleaning composition, as defined herein, comprising a dispersin and a protease, wherein the dispersin comprises or consists of the polypeptide comprising the amino acid sequence shown in SEQ ID NO: 15 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15. One embodiment relates to a cleaning composition, as defined herein, comprising a dispersin and a protease, wherein the dispersin comprises or consists of the polypeptide comprising the amino acid sequence shown in SEQ ID NO: 15 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16. One embodiment relates to a cleaning composition, as defined herein, comprising a dispersin and a protease, wherein the dispersin comprises or consists of the polypeptide comprising the amino acid sequence shown in SEQ ID NO: 16 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16. One embodiment relates to a cleaning composition, as defined herein, comprising a dispersin and a protease, wherein the dispersin comprises or consists of the polypeptide comprising the amino acid sequence shown in SEQ ID NO: 16 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16. One embodiment relates to a cleaning composition, as defined herein, comprising a dispersin and a protease, wherein the dispersin comprises or consists of the polypeptide comprising the amino acid sequence shown in SEQ ID NO: 16 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17. One embodiment relates to a cleaning composition, as defined herein, comprising a dispersin and a protease, wherein the dispersin comprises or consists of the polypeptide comprising the amino acid sequence shown in SEQ ID NO: 17 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17. One embodiment relates to a cleaning composition, as defined herein, comprising a dispersin and a protease, wherein the dispersin comprises or consists of the polypeptide comprising the amino acid sequence shown in SEQ ID NO: 17 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17. One embodiment relates to a cleaning composition, as defined herein, comprising a dispersin and a protease, wherein the dispersin comprises or consists of the polypeptide comprising the amino acid sequence shown in SEQ ID NO: 17 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18. One embodiment relates to a cleaning composition, as defined herein, comprising a dispersin and a protease, wherein the dispersin comprises or consists of the polypeptide comprising the amino acid sequence shown in SEQ ID NO: 18 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18. One embodiment relates to a cleaning composition, as defined herein, comprising a dispersin and a protease, wherein the dispersin comprises or consists of the polypeptide comprising the amino acid sequence shown in SEQ ID NO: 18 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18. One embodiment relates to a cleaning composition, as defined herein, comprising a dispersin and a protease, wherein the dispersin comprises or consists of the polypeptide comprising the amino acid sequence shown in SEQ ID NO: 18 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19. One embodiment relates to a cleaning composition, as defined herein, comprising a dispersin and a protease, wherein the dispersin comprises or consists of the polypeptide comprising the amino acid sequence shown in SEQ ID NO: 19 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19. One embodiment relates to a cleaning composition, as defined herein, comprising a dispersin and a protease, wherein the dispersin comprises or consists of the polypeptide comprising the amino acid sequence shown in SEQ ID NO: 19 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19. One embodiment relates to a cleaning composition, as defined herein, comprising a dispersin and a protease, wherein the dispersin comprises or consists of the polypeptide comprising the amino acid sequence shown in SEQ ID NO: 19 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20. One embodiment relates to a cleaning composition, as defined herein, comprising a dispersin and a protease, wherein the dispersin comprises or consists of the polypeptide comprising the amino acid sequence shown in SEQ ID NO: 20 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20. One embodiment relates to a cleaning composition, as defined herein, comprising a dispersin and a protease, wherein the dispersin comprises or consists of the polypeptide comprising the amino acid sequence shown in SEQ ID NO: 20 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20. One embodiment relates to a cleaning composition, as defined herein, comprising a dispersin and a protease, wherein the dispersin comprises or consists of the polypeptide comprising the amino acid sequence shown in SEQ ID NO: 20 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21. One embodiment relates to a cleaning composition, as defined herein, comprising a dispersin and a protease, wherein the dispersin comprises or consists of the polypeptide comprising the amino acid sequence shown in SEQ ID NO: 21 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21. One embodiment relates to a cleaning composition, as defined herein, comprising a dispersin and a protease, wherein the dispersin comprises or consists of the polypeptide comprising the amino acid sequence shown in SEQ ID NO: 21 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21. One embodiment relates to a cleaning composition, as defined herein, comprising a dispersin and a protease, wherein the dispersin comprises or consists of the polypeptide comprising the amino acid sequence shown in SEQ ID NO: 21 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22. One embodiment relates to a cleaning composition, as defined herein, comprising a dispersin and a protease, wherein the dispersin comprises or consists of the polypeptide comprising the amino acid sequence shown in SEQ ID NO: 22 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22. One embodiment relates to a cleaning composition, as defined herein, comprising a dispersin and a protease, wherein the dispersin comprises or consists of the polypeptide comprising the amino acid sequence shown in SEQ ID NO: 22 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22. One embodiment relates to a cleaning composition, as defined herein, comprising a dispersin and a protease, wherein the dispersin comprises or consists of the polypeptide comprising the amino acid sequence shown in SEQ ID NO: 22 and wherein the protease comprises or consists of the polypeptide comprising the amino acid sequence shown in SEQ ID NO: 26.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23. One embodiment relates to a cleaning composition, as defined herein, comprising a dispersin and a protease, wherein the dispersin comprises or consists of the polypeptide comprising the amino acid sequence shown in SEQ ID NO: 23 and wherein the protease comprises or consists of the polypeptide comprising the amino acid sequence shown in SEQ ID NO: 24.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23. One embodiment relates to a cleaning composition, as defined herein, comprising a dispersin and a protease, wherein the dispersin comprises or consists of the polypeptide comprising the amino acid sequence shown in SEQ ID NO: 23 and wherein the protease comprises or consists of the polypeptide comprising the amino acid sequence shown in SEQ ID NO: 25.

One embodiment relates to a cleaning composition, as defined herein, comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23. One embodiment relates to a cleaning composition, as defined herein, comprising a dispersin and a protease, wherein the dispersin comprises or consists of the polypeptide comprising the amino acid sequence shown in SEQ ID NO: 23 and wherein the protease comprises or consists of the polypeptide comprising the amino acid sequence shown in SEQ ID NO: 26.

One embodiment of the invention relates to a cleaning composition, as defined herein, comprising a protease and a polypeptide having dispersin activity, wherein the polypeptide is selected from the group consisting of:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13, n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14, o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15, p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16, q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17, r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18, s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19, t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20, u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21, v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22, and w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, and wherein the composition preferably comprises at least one cleaning component.

One embodiment of the invention relates to a cleaning composition, as defined herein, comprising a protease and a polypeptide having dispersin activity, wherein the polypeptide is selected from the group consisting of:

a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1, b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2, c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3, d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4, e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5, f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6, g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7, h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8, i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9, j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10, k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11, l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12, m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19,
t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20,
u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21,
v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22, and
w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23,
wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 25, and wherein the composition preferably comprises at least one cleaning component.

One embodiment of the invention relates to a cleaning composition, as defined herein, comprising a protease and a polypeptide having dispersin activity, wherein the polypeptide is selected from the group consisting of:
a) a polypeptide having at least 60%, at least 65%, at least 70%, at least 75% at least 80%, at least 85%, at least 90%, at least 95%, at least 98% or 100% sequence identity to the polypeptide shown in SEQ ID NO: 1,
b) a polypeptide having at least 60%, at least 65%, at least 70%, at least 75% at least 80%, at least 85%, at least 90%, at least 95%, at least 98% or 100% sequence identity to the polypeptide shown in SEQ ID NO: 2,
c) a polypeptide having at least 60%, at least 65%, at least 70%, at least 75% at least 80%, at least 85%, at least 90%, at least 95%, at least 98% or 100% sequence identity to the polypeptide shown in SEQ ID NO: 3,
d) a polypeptide having at least 60%, at least 65%, at least 70%, at least 75% at least 80%, at least 85%, at least 90%, at least 95%, at least 98% or 100% sequence identity to the polypeptide shown in SEQ ID NO: 4,
e) a polypeptide having at least 60%, at least 65%, at least 70%, at least 75% at least 80%, at least 85%, at least 90%, at least 95%, at least 98% or 100% sequence identity to the polypeptide shown in SEQ ID NO: 5,
f) a polypeptide having at least 60%, at least 65%, at least 70%, at least 75% at least 80%, at least 85%, at least 90%, at least 95%, at least 98% or 100% sequence identity to the polypeptide shown in SEQ ID NO: 6,
g) a polypeptide having at least 60%, at least 65%, at least 70%, at least 75% at least 80%, at least 85%, at least 90%, at least 95%, at least 98% or 100% sequence identity to the polypeptide shown in SEQ ID NO: 7,
h) a polypeptide having at least 60%, at least 65%, at least 70%, at least 75% at least 80%, at least 85%, at least 90%, at least 95%, at least 98% or 100% sequence identity to the polypeptide shown in SEQ ID NO: 8,
i) a polypeptide having at least 60%, at least 65%, at least 70%, at least 75% at least 80%, at least 85%, at least 90%, at least 95%, at least 98% or 100% sequence identity to the polypeptide shown in SEQ ID NO: 9,
j) a polypeptide having at least 60%, at least 65%, at least 70%, at least 75% at least 80%, at least 85%, at least 90%, at least 95%, at least 98% or 100% sequence identity to the polypeptide shown in SEQ ID NO: 10,
k) a polypeptide having at least 60%, at least 65%, at least 70%, at least 75% at least 80%, at least 85%, at least 90%, at least 95%, at least 98% or 100% sequence identity to the polypeptide shown in SEQ ID NO: 11,
l) a polypeptide having at least 60%, at least 65%, at least 70%, at least 75% at least 80%, at least 85%, at least 90%, at least 95%, at least 98% or 100% sequence identity to the polypeptide shown in SEQ ID NO: 12,
m) a polypeptide having at least 60%, at least 65%, at least 70%, at least 75% at least 80%, at least 85%, at least 90%, at least 95%, at least 98% or 100% sequence identity to the polypeptide shown in SEQ ID NO: 13,
n) a polypeptide having at least 60%, at least 65%, at least 70%, at least 75% at least 80%, at least 85%, at least 90%, at least 95%, at least 98% or 100% sequence identity to the polypeptide shown in SEQ ID NO: 14,
o) a polypeptide having at least 60%, at least 65%, at least 70%, at least 75% at least 80%, at least 85%, at least 90%, at least 95%, at least 98% or 100% sequence identity to the polypeptide shown in SEQ ID NO: 15,
p) a polypeptide having at least 60%, at least 65%, at least 70%, at least 75% at least 80%, at least 85%, at least 90%, at least 95%, at least 98% or 100% sequence identity to the polypeptide shown in SEQ ID NO: 16,
q) a polypeptide having at least 60%, at least 65%, at least 70%, at least 75% at least 80%, at least 85%, at least 90%, at least 95%, at least 98% or 100% sequence identity to the polypeptide shown in SEQ ID NO: 17,
r) a polypeptide having at least 60%, at least 65%, at least 70%, at least 75% at least 80%, at least 85%, at least 90%, at least 95%, at least 98% or 100% sequence identity to the polypeptide shown in SEQ ID NO: 18,
s) a polypeptide having at least 60%, at least 65%, at least 70%, at least 75% at least 80%, at least 85%, at least 90%, at least 95%, at least 98% or 100% sequence identity to the polypeptide shown in SEQ ID NO: 19,
t) a polypeptide having at least 60%, at least 65%, at least 70%, at least 75% at least 80%, at least 85%, at least 90%, at least 95%, at least 98% or 100% sequence identity to the polypeptide shown in SEQ ID NO: 20, u) a polypeptide having at least 60%, at least 65%, at least 70%, at least 75% at least 80%, at least 85%, at least 90%, at least 95%, at least 98% or 100% sequence identity to the polypeptide shown in SEQ ID NO: 21, v) a polypeptide having at least 60%, at least 65%, at least 70%, at least 75% at least 80%, at least 85%, at least 90%, at least 95%, at least 98% or 100% sequence identity to the polypeptide shown in SEQ ID NO: 22, and w) a polypeptide having at least 60%, at least 65%, at least 70%, at least 75% at least 80%, at least 85%, at least 90%, at least 95%, at least 98% or 100% sequence identity to the polypeptide shown in SEQ ID NO: 23, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 26, and wherein the composition preferably comprises at least one cleaning component.

One embodiment relates to a cleaning composition, as defined herein, comprising a dispersin and a protease, wherein the dispersin comprises or consists of a polypeptide selected from the group of polypeptides comprising the amino acid sequence shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23 and wherein the protease comprises or consists of the polypeptide comprising the amino acid sequence shown in SEQ ID NO: 24.

One embodiment relates to a cleaning composition, as defined herein, comprising a dispersin and a protease, wherein the dispersin comprises or consists of a polypeptide selected from the group of polypeptides comprising the amino acid sequence shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23 and wherein the protease comprises or consists of the polypeptide comprising the amino acid sequence shown in SEQ ID NO: 25.

One embodiment relates to a cleaning composition, as defined herein, comprising a dispersin and a protease, wherein the dispersin comprises or consists of a polypeptide selected from the group of polypeptides comprising the amino acid sequence shown in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22 and SEQ ID NO: 23 and wherein the protease comprises or consists of the polypeptide comprising the amino acid sequence shown in SEQ ID NO: 26.

One embodiment relates to a composition, as defined herein, comprising a) at least 0.001 ppm of at least one polypeptide having dispersin activity, wherein the dispersin is selected from the group consisting of:

i. a dispersin obtained from *Terribacillus;* ii. a dispersin obtained from *Curtobacterium;* iii. a dispersin obtained from *Aggregatibacter;* iv. a dispersin obtained from *Haemophilus;* v. a dispersin obtained from *Actinobacillus;* vi. a dispersin obtained from *Lactobacillus;* vii. a dispersin obtained from or *Staphylococcus;* viii. a polypeptide having hexosaminidase activity selected from: a polypeptide having at least 60%, at least 70%, at least 75%, at least 80%, at least 85%, at least 90%, at least 95%, at least 98%, at least 99% or 100% sequence identity to the polypeptide shown in SEQ ID NO: 1, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 2, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 3, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 4, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 5, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 6, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 7, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 8, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 9, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 10, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 11, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 12, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 13, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 92, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 15, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 16, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 17, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 18, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 19, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 20, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 21, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 22, a polypeptide having at least 60%, at least 70%, at least 75%, at least 80%, at least 85%, at least 90%, at least 95%, at least 98%, at least 99% or 100% sequence identity to the polypeptide shown in SEQ ID NO: 23, and b) at least 0.01 ppm of at least one protease, wherein the protease is selected from, i) a protease variant of a protease parent, wherein the protease variant comprises one or more alteration(s) compared to a protease shown in SEQ ID NO: 24 or SEQ ID NO: 25 in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269, wherein the positions correspond to the positions of the protease shown in SEQ ID NO: 24 and wherein the protease variant has at least 60%, at least 65%, at least 70%, at least 75% at least 80%, at least 85%, at least 90%, at least 95%, at least 98% but less than 100% sequence identity to SEQ ID NO: 24 or SEQ ID NO: 25;

ii) a protease variant of a protease parent, wherein the protease variant comprises one or more mutation selected from the group consisting of X3T, X4I, X9R, X9E, X15T, X24G, X24R, X27R, X42R, X55P, X59E, X59D, X60D, X60E, X66A, X74D, X85R, X96S, X97G, X97D, X97A, X97XD, X99E, X99D, X99G, X99M, X99N, X99R, X99H, X101A, X102I, X102Y, X102N, X104A, X116V, X116R, X118D, X118N, X120S, X126L, X127Q, X128A, X154D, X156E, X157D, X157P, X158E, X161A, X164S, X176E, X179E, X182E, X185N, X188P, X189E, X193M, X198D, X1991, X203W, X206G, X211Q, X211D, X212D, X212S, X216S, X226V, X229L, X230H, X239R, X246K, X255W, X255D, X255E, X256E, X256D X268A and X269H, wherein the positions correspond to the positions of the protease shown in SEQ ID NO: 24, wherein the protease variant has at least 60%, at least 65%, at least 70%, at least 75% at least 80%, at least 85%, at least 90%, at least 95%, at least 98% but less than 100% sequence identity to SEQ ID NO: 24 or SEQ ID NO: 25;

iii) a protease comprising a substitution at one or more positions corresponding to positions 171, 173, 175, 179, or 180 of SEQ ID NO: 26, compared to the protease shown in SEQ ID NO: 26, wherein the protease variant has a sequence identity of at least 60%, at least 65%, at least 70%, at least 75% at least 80%, at least 85%, at least 90%, at least 95%, at least 98% but less than 100% identity to amino acid sequence 1 to 311 of SEQ ID NO: 26, iv) a protease comprising the amino acid sequence shown in SEQ ID NO: 24, 25, 26 or a protease having at least 60%, at least 65%, at least 70%, at least 75% at least 80%, at least 85%, at least 90%, at least 95%, at least 98% or 100% sequence identity to; the polypeptide comprising amino acids 1-269 of SEQ ID NO: 24, the polypeptide comprising amino acids 1-311 of SEQ ID NO: 26, the polypeptide comprising amino acids 1-275 of SEQ ID NO: 25;

v) a protease comprising the amino acid sequence shown in SEQ ID NO: 27, SEQ ID NO: 28, SEQ ID NO: 29, SEQ ID NO: 30, SEQ ID NO: 31 or a protease having at least 60%, at least 65%, at least 70%, at least 75% at least 80%, at least 85%, at least 90%, at least 95%, at least 98%, preferably 100% sequence identity hereto; and vi) one or more of the following protease variants selected from the group consisting of:

SEQ ID NO: 24+T22R+S99G+S101A+V102I+A226V+Q239R;

SEQ ID NO: 25+S24G+S53G+S78N+S101N+G128A+Y217Q;

SEQ ID NO: 25+S24G+S53G+S78N+S101N+G128S+Y217Q;

SEQ ID NO: 24+S9E+N42R+N74D+V199I+Q200L+Y203W+S253D+N255W+L256E;

SEQ ID NO: 24+S9E+N42R+N74D+H118V+Q176E+A188P+V199I+Q200L+Y203W+S250D+S253D+N255W+L256E;

SEQ ID NO: 24+S9E+N42R+N74D+Q176E+A188P+V199I+Q200L+Y203W S250D+S253D+N255W+L256E;

SEQ ID NO: 24+S3V+N74D+H118V+Q176E+N179E+S182E+V199I+Q200L Y203W+S210V+S250D+S253D+N255W+L256E;

SEQ ID NO: 24+T22A+N60D+S99G+S101A+V102I+N114L+G157D+S182D+T207A+A226V+Q239R+N242D+E265F;

SEQ ID NO: 24+S9E+N42R+N74D+H118V+Q176E+A188P+V199I+Q200L+Y203W+S250D+S253D+N255W+L256E,

SEQ ID NO: 24+S9E+N42R+N74D+Q176E+A188P+V199I+Q200L+Y203W+S250D+S253D+N255W+L256E,

SEQ ID NO: 24+S9E+N42R+N74D+H118V+Q176E+A188P+V199I+Q200L+Y203W+S250D+N255W+L256E+*269aH+*269bH,

SEQ ID NO: 24+S3V+N74D+H118V+Q176E+N179E+S182E+V199I+Q200L+Y203W+S210V+S250D+N255W+L256E,

SEQ ID NO: 24+S9E+N74D+G113W+G157P+Q176E+V199I+Q200L+Y203W+S250D+T254E+N255W+L256E,

SEQ ID NO: 24+S3V+S9R+N74D+H118V+Q176E+N179E+S182E+V199I+Q200L+Y203W+S212V+S250D+N255W+L256E,

SEQ ID NO: 24+S99E,

SEQ ID NO: 25+L217D.

The protease and dispersin may be included in the cleaning composition of the present invention at a level of from 0.01 to 1000 ppm, from 1 ppm to 1000 ppm, from 10 ppm to 1000 ppm, from 50 ppm to 1000 ppm, from 100 ppm to 1000 ppm, from 150 ppm to 1000 ppm, from 200 ppm to 1000 ppm, from 250 ppm to 1000 ppm, from 250 ppm to 750 ppm, from 250 ppm to 500 ppm.

The dispersins above may be combined with proteases to form a blend to be added to the wash liquor solution. The concentration of the dispersin in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm. The concentration of the protease in the wash liquor solution is typically in the range of wash liquor from 0.00001 ppm to 10 ppm, from 0.00002 ppm to 10 ppm, from 0.0001 ppm to 10 ppm, from 0.0002 ppm to 10 ppm, from 0.001 ppm to 10 ppm, from 0.002 ppm to 10 ppm, from 0.01 ppm to 10 ppm, from 0.02 ppm to 10 ppm, 0.1 ppm to 10 ppm, from 0.2 ppm to 10 ppm, from 0.5 ppm to 5 ppm.

The dispersins may be combined with any of the proteases below to form a blend to be added to a composition according to the invention.

One embodiment relates to a cleaning composition, as defined herein, comprising a dispersin and a protease, wherein the amount of dispersin in the composition is from 0.01 to 1000 ppm and the amount of protease is from 0.01 to 1000 ppm.

In addition to the protease and dispersin, the cleaning composition may further comprise at least one cleaning component. One embodiment relates to a cleaning composition, as defined herein, comprising a dispersin, a protease and at least one cleaning component, wherein the cleaning component is selected from surfactants, preferably anionic and/or nonionic, builders and bleach components.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Surfactants

The cleaning composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 0.1% to about 15% or about 3% to about 10%. "About", as used herein in relation to a numerical value means said value ±10%, preferably ±5%. "About 5 wt %" thus means from 4.5 to 5.5 wt %, preferably from 4.75 to 5.25 wt %. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weight of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0.01 to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.01% to about 10% by weight of a zwitterionic surfactant. Non-limiting examples of zwitterionic surfactants include betaines such as alkyldimethylbetaines, sulfobetaines, and combinations thereof.

Preferred anionic surfactants are sulfate surfactants and in particular alkyl ether sulfates, especially C9-C15 alcohol ether sulfates, preferably ethoxylates or mixed ethoxylates/propoxylates, such as those with 1 to 30 EO, C12-C15 primary alcohol ethoxylate, such as those with 1 to 30 EO, C8-C16 ester sulfates and C10-C14 ester sulfates, such as mono dodecyl ester sulphates. Non-limiting examples of anionic surfactants include sulfates and sulfonates, in particular, linear alkylbenzenesulfonates (LAS), in particular C12-C13 alkyl benzene sulfonates, isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ether sulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof. The anionic surfactants are preferably added to the detergent in the form of salts. Suitable cations in these salts are alkali metal ions, such as sodium, potassium and lithium and ammonium salts, for example (2-hydroxyethyl) ammonium, bis(2-hydroxyethyl) ammonium and tris(2-hydroxyethyl) ammonium salts. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof. Commercially available nonionic surfactants include Plurafac™, Lutensol™ and Pluronic™ range from BASF, Dehypon™ series from Cognis and Genapol™ series from Clariant.

In various embodiments, said surfactant preferably comprises at least one alkyl ether sulfate. Preferred alkyl ether sulfates are those of formula (I)

$$R^1\text{—O-(AO)}_n\text{—SO}_3\text{-X}^+ \quad \text{(I).}$$

In formula (I) $R^1$ represents a linear or branched, substituted or unsubstituted alkyl group, preferably a linear, unsubstituted alkyl group, more preferably a fatty alcohol moiety. Preferred $R^1$ moieties are selected from the group consisting of decyl, undecyl, dodecyl, tridecyl, tetradecyl, pentadecyl, hexadecyl, heptadecyl, octadecyl, nonadecyl, eicosyl moieties and mixtures thereof, wherein those groups with an even number of carbon atoms are preferred. Particularly preferred $R^1$ moieties are derived from $C_{10}$-$C_{18}$ fatty alcohols, such as those derived from coconut oil alcohols, tallow fatty alcohols, lauryl, myristyl, cetyl or stearyl alcohol or from $C_{10}$-$C_{20}$ oxoalcohols.

AO represents an ethyleneoxide (EO) or propyleneoxide (PO) group, preferably an ethyleneoxide group. The index n represents an integer from 1 to 50, preferably from 1 to 20 and more preferably from 1 to 10. Particularly preferably, n is 1, 2, 3, 4, 5, 6, 7 or 8. X represents a monovalent cation or the n-th part of an n-valent cation, preferred are alkali metal cations, specifically $Na^+$ and $K^+$, most preferably $Na^+$. Further cations $X^+$ may be selected from $NH_4^+$, ½$Zn^{2+}$, ½$Mg^{2+}$, ½$Ca^{2+}$, ½$Mn^{2+}$, and combinations thereof.

In various preferred embodiments, the detergent compositions comprise an alkyl ether sulfate selected from fatty alcohol ether sulfates of formula (II)

(II)

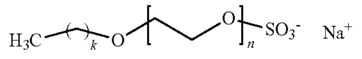

wherein k=9 to 19, and n=1, 2, 3, 4, 5, 6, 7 or 8. Preferred are $C_{10-16}$ fatty alcohol ether sulfates with 1-7 EO (k=9-15, n=1-7), such as the $C_{12-14}$ fatty alcohol ether sulfates with 1-3, particularly 2 EO (k=11-13, n=1-3 or 2), more particularly the sodium salts thereof. One specific embodiment thereof is lauryl ether sulfate sodium salt with 2 EO. The level of ethoxylation is an average value and can, for a specific compound, be an integer or fractional number.

In various embodiments, the surfactant comprises at least one alkyl benzene sulfonate. Said alkyl benzene sulfonate may be present alternatively to the above alkyl ether sulfate or, preferably, in addition to it.

Exemplary alkyl benzene sulfonates include, but are not limited to linear and branched alkyl benzene sulfonates, preferably linear alkyl benzene sulfonates. Exemplary compounds are those of formula (III)

(III)

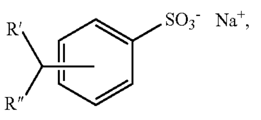

wherein R' and R" are independently H or alkyl and combined comprise 9 to 19, preferably 9 to 15 and more preferably 9 to 13 carbon atoms. Particularly preferred are dodecyl and tridecyl benzene sulfonates, in particular the sodium salts thereof.

In addition or alternatively, the compositions of the invention may further comprise one or more nonionic surfactants. Preferred nonionic surfactants are those of formula (IV)

$$R^2\text{—O-(AO)}_m\text{—H} \quad \text{(IV),}$$

wherein $R^2$ represents a linear or branched substituted or unsubstituted alkyl moiety, AO represents an ethylene oxide (EO) or propylene oxide (PO) group and m is an integer from 1 to 50.

In formula (IV) $R^2$ preferably represents a linear or branched, substituted or unsubstited alkyl group, preferably a linear, unsubstituted alkyl group, particularly preferred a fatty alcohol group. Preferred groups of $R^2$ are selected from decyl, undecyl, dodecyl, tridecyl, tetradecyl, pentadecyl, hexadecyl, heptadecyl, octadecyl, nonadecyl, eicosyl groups and combinations thereof, wherein those groups with an even number of carbon atoms are preferred. Particularly preferred are $R^2$ groups derived from $C_{12}$-$C_{18}$ fatty alcohols, such as coconut oil alcohol, tallow oil alcohol, lauryl, myristyl, cetyl or stearyl alcohol or from $C_{10}$-$C_{20}$ oxoalcohols.

AO represents an ethyleneoxide (EO) or propyleneoxide (PO) group, preferably an ethyleneoxide group. The index m represents an integer from 1 to 50, preferably from 1 to 20 and more preferably from 1 to 6. Particularly preferably, m is 1, 2, 3, 4 or 5, most preferably 3-5, as higher degrees of ethoxylation may negatively influence viscosity and stability.

In various preferred embodiments, the detergent compositions comprise an alkyl ether selected from fatty alcohol ethers of formula (V)

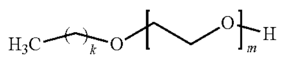

(V)

wherein k=11 to 19, m=1, 2, 3, 4, 5, 6, 7 or 8. Preferred are $C_{12-18}$ fatty alcohols with 1-6 EO (k=11-17, m=1-5 in formula (V)). More preferred are $C_{12-14}$ alcohols having 1-5 EO, most preferred are $C_{12-14}$ alkyl ethers with 3-5 EO, in particular lauryl ether with 5 EO.

The detergent compositions may further include other nonionic surfactants, such as alkyl glucosides of the general formula $RO(G)_x$, where R is a primary linear or 2-methyl-branched aliphatic radical containing 8 to 22 and preferably 12 to 18 carbon atoms and G stands for a glucose unit. The degree of oligomerization x, which indicates the distribution of monoglucosides and oligoglucosides, is a number of 1 to 10 and preferably a number of 1.2 to 1.4.

In various embodiments, the composition comprises at least two anionic surfactants, e.g. at least one alkyl ether sulfate and preferably at least one alkyl benzene sulfonate, and optionally an alkyl ether.

Suitable amphoteric surfactants comprise betains. Preferred betaines are the alkylbetaines, the alkylamidobetaines, the imidazolinium betaines, the sulfobetaines (INCI Sultaines) and the phosphobetaines. Examples of suitable betaines and sulfobetaines are the following compounds designated as INCI: almondamidopropyl betaines, apricotam idopropyl betaines, avocadamidopropyl betaines, babassuamidopropyl betaines, behenamide idopropyl betaines, behenyl betaines, betaines, canola idopropyl betaines, caprylic/capram idopropyl betaines, carnitines, cetyl betaines, cocamidoethyl betaines, cocamidopropyl betaines, cocam idopropyl hydroxysultaines, cocobetaines, coco-hydroxysultaines, coco/oleam idopropyl betaines, coco-sultaines, decyl betaines, dihydroxyethyl oleyl glycinates, dihydroxyethyl soy glycinates, dihydroxyethyl stearyl glycinates, dihydroxyethyl tallow glycinates, dimethicones propyl PG Betaines, erucam idopropyl hydroxysultaines, hydrogenated tallow betaines, isostearam idopropyl betaines, lauram idopropyl betaines, lauryl betaines, lauryl hydroxysultaine, lauryl sultaines, milkamidopropyl betaines, minkam idopropyl betaines, myristamine idopropyl betaines, myristyl betaines, oleam idopropyl betaines, oleam idropy Hydroxysultain, Oleyl Betaine, Olivamidopropyl Betaine, Palmam Idopropyl Betaine, Palm Itam Idopropyl Betaine, Palmitoyl Carnitine, Palm Kernelamidopropyl Betaine, Polytetrafluoroethylene Acetoxypropyl Betaine, Ricinoleam Idopropyl Betaine, Sesamidopropyl Betaine, Soyamidopropyl Betaine, Stearam Idopropyl Betaine, Stearyl Betaine, Tallowam Idopropyl Betaine, Tallowamidopropyl Hydroxysultaine, Tallow Betaine, Tallow Dihydroxyethyl Betaine, Undecylenamidopropyl Betaine and Wheat Germamidopropyl Betaine. A preferred betaine is, for example, cocamidopropyl betaine (cocoamidopropylbetaine). The betaines are particularly preferred for dishwashing compositions, most preferably hand dishwashing detergent compositions.

Further suitable surfactants include the amine oxides. The amine oxides suitable in accordance with the invention include alkylamine oxides, in particular alkyldimethylamine oxides, alkylamidoamine oxides and alkoxyalkylamine oxides. Examples of suitable amine oxides are the following compounds designated as INCI: Almond amidopropylamine oxides, Babassu amidopropylamine oxides, Behenamine oxides, Cocamidopropyl Amine oxides, Cocamidopropylamine oxides, Cocamine oxides, Coco-Morpholine oxides, Decylamine oxides, Decyltetradecylamine oxides, Diaminopyrimidine oxides, Dihydroxyethyl C8-10 alkoxypropylamines oxides, Dihydroxyethyl C9-11 alkoxypropylamines oxides, dihydroxyethyl C12-15 alkoxypropylamines oxides, dihydroxyethyl cocamine oxides, dihydroxyethyl lauramine oxides, dihydroxyethyl stearamines oxides, dihydroxyethyl tallowamine oxides, hydrogenated palm kernel amine oxides, hydrogenated tallowamine oxides, hydroxyethyl hydroxypropyl C12-15 alkoxypropylamines oxides, isostearamidopropylamines Oxides, isostearamidopropyl morpholine oxides, lauram idopropylamine oxides, lauramine oxides, methyl morpholine oxides, milkamidopropyl amine oxides, mincamidopropylamine oxides, myristamine idopropylamine oxides, myristamine oxides, myristyl/cetyl amines Oxides, Oleam idopropylamine oxides, Oleamine oxides, Olivam idopropylamine oxides, Palmitamidopropylamine oxides, Palmitamine oxides, PEG-3 Lauramine oxides, Potassium dihydroxyethyl Cocamine oxides phosphates, Potassium Trisphosphonomethylamine oxides, Sesamidopropylamine oxides, Soyamidopropylamine oxides, Stearam idopropylamine oxides, stearamines Oxides, Tallowam idopropylamine oxides, Tallowamine oxides, Undecylenamidopropylamine oxides and Wheat Germam idopropylamine oxides. A preferred amine oxide is, for example, cocamidopropylamine oxides (cocoamidopropylamine oxide).

For automatic dishwashing applications, low-foaming nonionic surfactants are preferably used, in particular alkoxylated, especially ethoxylated, low-foaming nonionic surfactants. With particular preference, the automatic dishwashing detergents contain nonionic surfactants from the group of the alkoxylated alcohols. Particular preference is given to nonionic surfactants which have a melting point above room temperature. Nonionic surfactants having a melting point above 20° C., preferably above 25° C., more preferably between 25 and 60° C. and especially between 26.6 and 43.3° C., are particularly preferred. Preferably used surfactants are those from the groups of alkoxylated nonionic surfactants, in particular the ethoxylated primary alcohols and mixtures of these surfactants with structurally more complex surfactants such as polyoxypropylene/polyoxyethylene/polyoxypropylene ((PO/EO/PO) surfactants). Such (PO/EO/PO) nonionic surfactants are also characterized by good foam control. Particularly preferred nonionic surfactants are those containing alternating ethylene oxide and different alkylene oxide units. Among these, in turn, surfactants with EO-AO-EO-AO blocks are preferred, with one to ten EO or AO groups before one block from the other group follows. Exemplary nonionic surfactants are those having a C9-alkyl group with 1 to 4 ethylene oxide units followed by 1 to 4 propylene oxide units, followed by 1 to 4 ethylene oxide units followed by 1 to 4 propylene oxide units. Preference is given in particular to end-capped, poly (oxy-alkylated) nonionic surfactants with the end-cap being a linear or branched, saturated or unsaturated, aliphatic or aromatic hydrocarbon radical R having 1 to 30 carbon atoms. The alkyl groups may also comprise hydroxyl groups. The group of these nonionic surfactants include, for example, the C4-22 fatty alcohol $(EO)_{10-50}$-2- hydroxyalkyl ethers, in particular also the C8-12 fatty alcohol $(EO)_{22}$-2-hydroxydecyl ethers and the C4-22 fatty alcohol $(EO)_{40-80}$-2-hydroxyalkyl ethers.

Builders and Co-Builders

The cleaning composition may contain about 0-65% by weight, such as about 5% to about 50%, such as about 0.5% to about 20% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053.

Generally and if not indicated otherwise, the builder may be preferably selected from citrate, carbonate, silicate, aluminosilicate (zeolite) and combinations thereof. Suitable builders also include phosphonates, polyphosphonates, bicarbonates, borates, and further polycarboxylates. Citrate builders, e.g., citric acid and soluble salts thereof (particularly sodium salt), are particularly suitable water-soluble organic builders. Citrates can be used in combination with zeolite, silicates like the BRITESIL types, and/or layered silicate builders. The builder and/or co-builder may be any chelating agent that forms water-soluble complexes with Ca and Mg. Any builder and/or co-builder known in the art for use in cleaning detergents may be utilized. Non-limiting examples of builders include zeolites, in particular zeolite A or P or X, carbonates such as sodium carbonate, soluble silicates such as sodium metasilicate, layered silicates (e.g., SKS-6 from Hoechst), and (carboxymethyl)inulin (CMI), and combinations thereof. Further non-limiting examples of builders include aminocarboxylates, aminopolycarboxylates, and alkyl- or alkenylsuccinic acid. Additional specific examples include 2,2',2-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N'-(2-hydroxyethyl)ethylenediamine-N,N,N'-triacetic acid (HEDTA), diethanolglycine (DEG), and combinations and salts thereof. Phosphonates suitable for use herein include 1-hydroxyethane-1,1-diphosphonic acid (HEDP), ethylenediaminetetrakis (methylenephosphonic acid) (EDTMPA), diethylenetriaminepentakis (methylenephosphonic acid) (DTMPA or DTPMPA or DTPMP), nitrilotris (methylenephosphonic acid) (ATMP or NTMP), 2-phosphonobutane-1,2,4-tricarboxylic acid (PBTC), hexamethylenediaminetetrakis (methylenephosphonic acid) (HDTMP). Particularly preferred are HEDP and DTPMP.

Suitable silicates are crystalline, layered sodium silicates of the general formula $NaMSi_xO_{2x+1}*yH_2O$, wherein M is sodium or H, x a number of from 1.9 to 4 and y a number of from 0 to 20 and x is preferably 2, 3 or 4. Such silicates are for example disclosed in EP-A-0 164 514. Preferred are silicates in which M is sodium and is 2 or 3. Particularly preferred are β- and δ-sodium disilicate $Na_2Si_2O_5*yH_2O$.

Although not preferred, the compositions may also comprise phosphates, diphosphates (pyrophosphates) and/or triphosphates such as sodium triphosphate (STP or STPP). It is however preferred that all compositions disclosed herein are phosphate-free, i.e. do not contain deliberately added phosphate, in particular the phosphate content is below 1 wt %, more preferably less than 0.5 wt %, even more preferably less than 0.1 wt %, relative to the total weight of the composition. In alternative embodiments, the invention also relates to phosphate-free cleaning compositions in general that contain the polypeptides of the invention. In one embodiment, the invention thus features a phosphate-free cleaning composition comprising any one or more of the polypeptides having hexosaminidase activity disclosed herein.

If not indicated otherwise, the composition may also contain 0-50% by weight, such as about 5% to about 30%, of a detergent co-builder. The composition may include a co-builder alone, or in combination with a builder, for example a zeolite builder. Non-limiting examples of co-builders include homopolymers of polyacrylates or copolymers thereof, such as poly (acrylic acid) (PAA) or copoly (acrylic acid/maleic acid) (PAA/PMA) or polyaspartic acid. Further exemplary builders and/or co-builders are described in, e.g., WO 09/102854, U.S. Pat. No. 5,977,053.

Preferred as co-builders are acrylate-containing water-soluble polymers, such as alkali metal salts of polyacrylic acid or polymethacrylic acid, for example those having a molecular weight $M_w$ in the range of 600 to 750,000 g/mol, as determined by gel permeation chromatography (GPC) according to DIN 55672-1:2007-08 with THE as an eluent.

Preferred polymers are polyacrylates with a molecular weight $M_w$ of 1,000 to 15,000 g/mol, more preferred, due to their solubility, are short-chain polyacrylates with a molecular weight $M_w$ of 1,000 to 10,000 g/mol, most preferred from 1,000 to 5,000 g/mol.

Preferred acrylates for use in the present invention are alkali metal salts of polymers of acrylic acid, preferably the sodium salts, in particular those with molecular weights in the range of 1,000 to 10,000 g/mol or 1,000 to 5,000 g/mol. Suitable acrylates are commercially available, for example under the tradename Acusol® from Dow Chemical. Suitable are also copolymers of acrylates, in particular those of acrylic acid and methacrylic acid, and acrylic acid or methacrylic acid and maleic acid.

In preferred embodiments, the compositions of the invention comprise a sulfopolymer, preferably a copolymer comprising an ethylenically unsaturated sulfonate/sulfonic acid as a co-monomer. Particularly suitable are monomers of allyl sulfonic acids, such as allyloxybenzene sulfonic acid and methallyl sulfonic acid. Particularly preferred sulfonic acid group-containing monomers are 1-acrylamido propane sulfonic acid-1, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxy-propanesulfonic acid, allylsulfonic acid, methallylsulfonic acid, allyloxybenzenesulfonic acid, methallyloxybenzolsulfonsäure, 2-hydroxy-3-(2-propenyloxy) propanesulfonic acid, 2-methyl-2-propenl-sulfonic acid, styrenesulfonic acid, vinylsulfonic acid, 3-sulfopropyl, sulfomethacrylamide, sulfomethylmethacrylamide and mixtures of said acids or their water-soluble salts.

The sulfopolymers are preferably copolymers of the afore-described monomers with unsaturated carboxylic acids, Especially preferred unsaturated carboxylic acids are acrylic acid, methacrylic acid, ethacrylic acid, chloroacrylic acid, alpha-cyanoacrylic acid, crotonic acid, alpha-phenylacrylic acid, maleic acid, maleic anhydride, fumaric acid, itaconic acid, citraconic acid, methylenemalonic acid, sorbic acid, cinnamic acid or mixtures thereof. Usable are of course also the unsaturated dicarboxylic acids. Preferred are copolymers with acrylates, in particular with acrylic acid and methacrylic acid, and acrylic acid or methacrylic acid and maleic acid.

Such polymers are, for example, commercially available under the trade names Acusol®590 or Acusol®588 from Dow Chemical.

In one embodiment of the invention, the cleaning compositions of the invention comprise a polypeptide as defined herein and at least one sulfopolymer, as defined above. Such compositions are preferably dishwashing compositions.

In one preferred embodiment, the builder is a non-phosphorus based builder such as citric acid and/or methylglycine-N,N-diacetic acid (MGDA) and/or glutamic-N,N-diacetic acid (GLDA) and/or salts thereof.

Bleaching Systems

The cleaning composition, as defined herein, may contain 0-30% by weight, such as about 1% to about 20%, such as about 0.01% to about 10% of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.

a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.

b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy) benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-KN-methanylylidene)triphenolato-K30]manganese(III). The bleach catalysts may also be other metal compounds; such as iron or cobalt complexes.

In some embodiments, where a source of a peracid is included, an organic bleach catalyst or bleach booster may be used having one of the following formulae:

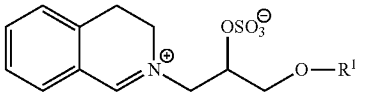

(i)

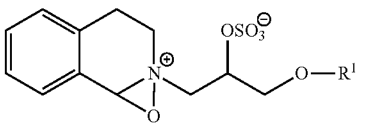

(ii)

(iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Metal Care Agents

Metal care agents may prevent or reduce the tarnishing, corrosion or oxidation of metals, including aluminium, stainless steel and non-ferrous metals, such as silver and copper. Suitable examples include one or more of the following:

(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain C1-C20-alkyl groups (e.g., C1-C20- alkyl groups) and hydroxyl, thio, phenyl or halogen such as fluorine, chlorine, bromine and iodine.

(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one embodiment, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate.

(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859. Preferably the composition of the invention comprises from 0.1 to 5% by weight of the composition of a metal care agent, preferably the metal care agent is a zinc salt.

Hydrotropes

The cleaning composition, as defined herein, may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Polymers

The cleaning composition, as defined herein, may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

Fabric Hueing Agents

The cleaning compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The cleaning composition, as defined herein, may comprise one or more additional enzymes such as one or more enzyme selected from lipases, cutinases, amylases, carbohydrases, cellulases, pectinases, mannanases, arabinases, galactanases, xylanases, oxidases, e.g., a laccase and/or peroxidase. In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259. Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544. Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. Suitable mannanases are described in WO 1999/064619. A commercially available mannanase is Mannaway (Novozymes A/S).

Lipases and Cutinases

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147). Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades). Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444. Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T491+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184. Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264. Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201 L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;

N128C+K178L+T182G+F202Y+Y305R+D319T+G475K;

S125A+N128C+K178L+T182G+Y305R+G475K; or

S125A+N128C+T131I+T165I+K178L+T182G+Y305R+G475K wherein the variants are C-terminally truncated and optionally further comprises a substitution at position 243 and/or a deletion at position 180 and/or position 181.

Further suitable amylases are amylases having SEQ ID NO: 1 of WO13184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K

E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO10104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21 D+D97N+V128I wherein the variants optionally further comprise a substitution at position 200 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™ Stainzyme Plus™, Natalase™, Liquozyme X and BAN™ (from Novozymes A/S), and Rapidase™ Purastar™/Effectenz™, Powerase, Preferenz S1000, Preferenz S100 and Preferenz S110 (from Genencor International Inc./DuPont).

Peroxidases/Oxidases

Typically, a peroxidase according to the invention is a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257. Commercially available peroxidases include Guardzyme™ (Novozymes A/S).

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as *Caldariomyces*, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO 92/01046), or *Coriolus*, e.g., *C. hirsutus* (JP 2238885). Suitable examples from bacteria include a laccase derivable from a strain of *Bacillus*. A laccase derived from *Coprinopsis* or *Myceliophthora* is preferred; in particular, a laccase derived from *Coprinopsis cinerea*, as disclosed in WO 97/08325; or from *Myceliophthora thermophila*, as disclosed in WO 95/33836.

Dispersants

The cleaning compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are, for example, described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Aquent

The cleaning compositions of the present invention will preferably also contain additional components that may tint articles being cleaned, such as fluorescent whitening agent or optical brighteners. Where present, the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers

The cleaning compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers is amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore, random graft co-polymers are suitable soil release polymers. Suitable graft co-polymers are described in more detail in WO 2007/138054, WO 2006/108856 and WO 2006/113314 (hereby incorporated by reference). Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan HP22. Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The cleaning compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The cleaning composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific embodiment, the present invention provides a detergent additive comprising one or more enzymes as described herein. The cleaning composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1. Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Granular Cleaning Formulations

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The dispersin may be formulated as a granule, for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry is disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt % zeolite (anhydrous basis); and (c) less than 10 wt % phosphate salt (anhydrous basis), wherein said enzyme co-granule comprises from 10 to 98 wt % moisture sink component and the composition additionally comprises from 20 to 80 wt % detergent moisture sink component. The multi-enzyme co-granule may comprise an enzyme of the invention and one or more enzymes selected from the group consisting of proteases, lipases, cellulases, xyloglucanases, perhydrolases, peroxidases, lipoxygenases, laccases, hemicellulases, proteases, cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, mannanases and amylases, and mixtures thereof. WO 2013/188331 also relates to a method of treating and/or cleaning a surface, preferably a fabric surface comprising the steps of (i) contacting said surface with the detergent composition as claimed and described herein in aqueous wash liquor, (ii) rinsing and/or drying the surface.

An embodiment of the invention relates to an enzyme granule/particle comprising the dispersin and protease. The granule is composed of a core, and optionally one or more coatings (outer layers) surrounding the core. Typically, the granule/particle size, measured as equivalent spherical diameter (volume based average particle size), of the granule is 20-2000 μm, particularly 50-1500 μm, 100-1500 μm or 250-1200 μm. The core may include additional materials such as fillers, fibre materials (cellulose or synthetic fibres), stabilizing agents, solubilising agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 μm, particularly 50-1500 μm, 100-1500 μm or 250-1200 μm. The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA). Examples of enzyme granules with multiple coatings are shown in WO 93/07263 and WO 97/23606. The coating may be applied in an amount of at least 0.1% by weight of the core, e.g., at least 0.5%, 1% or 5%. The amount may be at most 100%, 70%, 50%, 40% or 30%. The coating is preferably at least 0.1 μm thick, particularly at least 0.5 μm, at least 1 μm or at least 5 μm. In a one embodiment, the thickness of the coating is below 100 μm. In another embodiment, the thickness of the coating is below 60 μm. In an even more particular embodiment, the total thickness of the coating is below 40 μm. The coating should encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness. The coating can further contain other materials as known in the art, e.g., fillers, antisticking agents, pigments, dyes, plasticizers and/or binders, such as titanium dioxide, kaolin, calcium carbonate or talc. A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 μm, such as less than 10 μm or less than 5 μm. The salt coating may comprise a single salt or a mixture of two or more salts. The salt may be water soluble, and may have a solubility at least 0.1 grams in 100 g of water at 20° C., preferably at least 0.5 g per 100 g water, e.g., at least 1 g per 100 g water, e.g., at least 5 g per 100 g water. The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. The salt in the coating may have a constant humidity at 20° C. above 60%, particularly above 70%, above 80% or above 85%, or it may be another hydrate form of such a salt (e.g., anhydrate). The salt coating may be as described in WO 00/01793 or WO 2006/034710. Specific examples of suitable salts are NaCl ($CH_{20° C.}$=76%), $Na_2CO_3$($CH_{20° C.}$=92%), $NaNO_3$ ($CH_{20° C.}$=73%), $Na_2HPO_4$ ($CH_{20° C.}$=95%), $NaPO_4$ ($CH_{25° C.}$=92%), $NH_4Cl$ ($CH_{20° C.}$=79.5%), $(NH_4)_2HPO_4$ ($CH_{20° C.}$=93.0%), $NH_4H_2PO_4$ ($CH_{20° C.}$=93.1%), $(NH_4)_2SO_4$ ($CH_{20° C.}$=81.1%), KCl ($CH_{20° C.}$=85%), $K_2HPO_4$ ($CH_{20° C.}$=92%), $KH_2PO_4$ ($CH_{20° C.}$=96.5%), $KNO_3$ ($CH_{20° C.}$=93.5%), $Na_2SO_4$ ($CH_{20° C.}$=93%), $K_2SO_4$ ($CH_{20° C.}$=98%), $KHSO_4$ ($CH_{20° C.}$=86%), $MgSO_4$ ($CH_{20° C.}$=90%), $ZnSO_4$ ($CH_{20° C.}$=90%) and sodium citrate ($CH_{25° C.}$=86%). Other examples include $NaH_2PO_4$, $(NH_4)H_2PO_4$, $CuSO_4$, $Mg(NO_3)_2$ and magnesium acetate. The salt may be in anhydrous form, or it may be a hydrated salt, i.e. a crystalline salt hydrate with bound water(s) of crystallization, such as described in WO 99/32595. Specific examples include anhydrous sodium sulfate ($Na_2SO_4$), anhydrous magnesium sulfate ($MgSO_4$), magnesium sulfate heptahydrate ($MgSO_4.7H_2O$), zinc sulfate heptahydrate ($ZnSO_4.7H_2O$), sodium phosphate dibasic heptahydrate ($Na_2HPO_4.7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

One embodiment of the present invention provides a granule, which comprises:

(a) a core comprising a dispersin and a protease according to the invention, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22, and (b) optionally a coating consisting of one or more layer(s) surrounding the core.

One embodiment of the invention relates to a granule, which comprises:

(a) a core comprising a dispersin and a protease, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23, and (b) optionally a coating consisting of one or more layer(s) surrounding the core.

Uses

The present invention is also directed to methods for using the compositions of the invention in e.g. laundry/textile/fabric (House hold laundry washing, Industrial laundry washing) and hard surface cleaning (ADW, car wash, Industrial surface). The cleaning e.g. detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations. In a specific embodiment, the present invention provides a detergent additive comprising one or more enzymes as described herein.

The compositions of the invention comprise a blend of dispersin and protease and effectively reduce or remove organic components, such as protein and PNAG from surfaces such as textiles and hard surfaces e.g. dishes.

One embodiment of the invention relates to the use of a composition comprising a dispersin and protease for reduction of redeposition. One embodiment of the invention relates to the use of a cleaning composition, as defined herein, comprising a dispersin and protease for reduction of redeposition.

One embodiment of the invention relates to the use of a cleaning composition, as defined herein, comprising a dispersin and protease for reduction of redeposition when the cleaning composition is applied in e.g. laundry process. One embodiment of the invention relates to the use of a cleaning composition, as defined herein, comprising a dispersin and protease for reduction of redeposition on an item e.g. textile. In one embodiment, the composition is an anti-redeposition composition.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Terribacillus*.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Curtobacterium*.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Aggregatibacter*.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Haemophilus*.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Actinobacillus*.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Lactobacillus*.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Staphylococcus*.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2.

One embodiment of the invention relates to the use of a cleaning composition. as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22.

One embodiment of the invention relates to the use of a cleaning composition, as defined herein, comprising a dispersin and protease for reduction of redeposition, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23.

The compositions of the invention may comprise a blend of dispersin and protease and effectively reduce or limit malodor of e.g. textiles or hard surfaces such as dishes.

One embodiment of the invention relates to the use of a composition comprising a dispersin and protease for reduction of malodor. One embodiment of the invention relates to the use of a cleaning composition, as defined herein, comprising a dispersin and protease for reduction of malodor.

One embodiment of the invention relates to the use of a cleaning composition, as defined herein, comprising a dispersin and protease for reduction of malodor when the cleaning composition is applied in e.g. laundry process. One embodiment of the invention relates to the use of a cleaning composition, as defined herein, comprising a dispersin and protease for reduction of malodor on an item e.g. textile.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Terribacillus*.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Curtobacterium*.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Aggregatibacter*.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Haemophilus*.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Actinobacillus*.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Lactobacillus*.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Staphylococcus*.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22.

One embodiment of the invention relates to the use of a cleaning composition, as defined herein, comprising a dispersin and protease for reduction of malodor, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23.

The compositions of the invention comprise a blend of dispersin and protease and improve whiteness of textile. One embodiment of the invention relates to the use of a composition, as defined herein, comprising a dispersin and protease for improvement of whiteness of an item e.g. a textile. One embodiment of the invention relates to the use of a cleaning composition, as defined herein, comprising a dispersin and protease for improvement of whiteness. One embodiment of the invention relates to the use of a cleaning composition, as defined herein, comprising a dispersin and protease improve whiteness when the cleaning composition is applied in e.g. laundry process. One embodiment of the invention relates to the use of a cleaning composition, as defined herein, comprising a dispersin and protease improve whiteness on an item e.g. textile.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Terribacillus*.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Curtobacterium*.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Aggregatibacter*.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Haemophilus*.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Actinobacillus*.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Lactobacillus*.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Staphylococcus*.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22.

One embodiment of the invention relates to the use of a cleaning composition, as defined herein, comprising a dispersin and protease for improvement of whiteness, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23.

The compositions of the invention comprise a blend of dispersin and protease and effectively reduce or remove organic components, such as protein and PNAG from surfaces such as textiles and hard surfaces e.g. dishes. One embodiment of the invention relates to the use of a cleaning composition, as defined herein, comprising a dispersin and a protease for reduction or removal of biofilm and components of biofilm, such as PNAG and protease, of an item, wherein the item is a textile or a hard surface.

One embodiment of the invention relates to the use of a cleaning composition, as defined herein, comprising a dispersin, a protease and at least one cleaning component for deep cleaning of an item, wherein the item is a textile or a surface.

One embodiment of the invention relates to the use of a composition, as defined herein, comprising a dispersin and protease for reduction or removal of biofilm compounds such as PNAG and protease of an item. One embodiment of the invention relates to the use of a cleaning composition, as defined herein, comprising a dispersin and protease for reduction or removal of biofilm compounds such as PNAG and protease of an item such as textile. One embodiment of the invention relates to the use of a cleaning composition, as defined herein, comprising a dispersin and protease for deep cleaning e.g. reduction or removal of biofilm compounds such as PNAG and protease when the cleaning composition is applied in e.g. laundry process.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Terribacillus*.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Curtobacterium*.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Aggregatibacter*.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Haemophilus*.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Actinobacillus*.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Lactobacillus*.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin is obtained from *Staphylococcus*.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO:

29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22.

One embodiment of the invention relates to the use of a cleaning composition, as defined herein, comprising a dispersin and protease for deep cleaning of an item, wherein the protease has at least 60%, at least 65%, at least 70%, at least 75%, at least 80%, at least 85%, at least 90%, at least 95%, at least 98% or 100% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23.

The invention further relates to a method of deep cleaning of an item, comprising the steps of:

a) contacting the item with a cleaning composition according to the invention; and b) optionally rinsing the item, wherein the item is preferably a textile.

One embodiment of the invention relates to a method of deep cleaning on an item, comprising the steps of:

a) contacting the item with a composition of the invention comprising an enzyme mixture comprising a dispersin and a protease; and b) optionally rinsing the item, wherein the item is preferably a textile.

One embodiment of the invention relates to a method of deep cleaning on an item, comprising the steps of:

a) contacting the item with a composition of the invention comprising an enzyme mixture comprising a dispersin and a protease; and b) optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 1.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 2.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 3.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 4.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 5.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 6.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 7.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 8.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 9.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 10.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 11.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 12.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 13.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 14.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 15.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 16.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 17.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 18.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 19.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 20.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 21.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 22.

One embodiment of the invention relates to a method of deep cleaning on an item, comprising the steps of:

a) contacting the item with a composition of the invention comprising an enzyme mixture comprising a dispersin and a protease; and b) and optionally rinsing the item, wherein the item is preferably a textile, wherein the protease has at least 60%, at least 65%, at least 70%, at least 75%, at least 80%, at least 85%, at least 90%, at least 95% or at least 98% sequence identity to the amino acid sequence shown in SEQ ID NO: 24, SEQ ID NO: 25, SEQ ID NO: 26, SEQ ID NO: 27, SEQ ID NO: 28, SEQ ID NO: 29, SEQ ID NO: 30 or SEQ ID NO: 31 and wherein the dispersin has at least 60%, at least 65%, at least 70%, at least 75%, at least 80%, at least 85%, at least 90%, at least 95%, at least 98% or 100% sequence identity to the amino acid sequence shown in SEQ ID NO: 23.

Definitions

"Biofilm" is produced by any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community.

On laundry and textiles, examples of biofilm-producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp. On hard surfaces, examples of biofilm-producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis, Staphylococcus aureus* and *Stenotrophomonas* sp. In one embodiment, the biofilm producing strain is *Brevundimonas* sp. In one embodiment, the biofilm producing strain is *Pseudomonas alcaliphila* or *Pseudomonas fluorescens*. In one embodiment, the biofilm producing strain is *Staphylococcus aureus.*

By the term "deep cleaning" is meant reduction, disruption or removal of components which may be comprised in organic matter, e.g. biofilm, such as polysaccharides, proteins, DNA, soil or other components present in the organic matter.

Cleaning composition: The term "cleaning composition" refers to compositions that find use in the removal of undesired compounds from items to be cleaned, such as textiles. The cleaning composition may be used to e.g. clean textiles for both household cleaning and industrial cleaning. The terms encompasses any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pre-treatment). In addition to containing the enzymes, the cleaning composition may contain one or more additional enzymes (such as amylases, lipases, cutinases, cellulases, endoglucanases, xyloglucanases, pectinases, pectin lyases, xanthanases, peroxidases, haloperoxygenases, catalases and mannanases, or any mixture thereof), and/or cleaning components e.g. detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers, all of which are as defined herein.

The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides. Textile care benefits, which are not directly related to catalytic stain removal or prevention of redeposition of soils, are also important for enzyme detergency benefits. Examples of such textile care benefits are prevention or reduction of dye transfer from one textile to another textile or another part of the same textile (an effect that is also termed dye transfer inhibition or anti-backstaining), removal of protruding or broken fibers from a textile surface to decrease pilling tendencies or remove already existing pills or fuzz (an effect that also is termed anti-pilling), improvement of the textile-softness, colour clarification of the textile and removal of particulate soils which are trapped in the fibers of the textile. Enzymatic bleaching is a further enzyme detergency benefit where the catalytic activity generally is used to catalyze the formation of bleaching component such as hydrogen peroxide or other peroxides or other bleaching species."

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, cutlery such as spoons, knives, forks, serving utensils, ceramics, plastics, metals, china, glass and acrylics.

The term "wash performance" is used as an enzyme's ability to remove stains present on the object to be cleaned during e.g. wash or hard surface cleaning.

The term "whiteness" is defined herein as a measure of the greying or yellowing of a textile. Loss of whiteness may be due to removal of optical brighteners/hueing agents. Greying and yellowing can be due to soil redeposition, body soils, colouring from e.g. iron and copper ions or dye transfer. Loss of whiteness can be related to one or several issues from the list below: colourant or dye effects; incomplete stain removal (e.g. body soils, sebum etc.); redeposition (greying, yellowing or other discolourations of the object) (removed soils reassociate with other parts of textile, soiled or unsoiled); chemical changes in textile during application; and clarification or brightening of colours.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhered to the item. One example of malodor is due to compounds with an unpleasant smell, which may be produced by microorganisms. Another example of unpleasant smells can be sweat or body odor adhered to an item which has been in contact with human or animal. Another example of malodor can be the odor from spices, which sticks to items for example curry or other exotic spices which smells strongly.

The term "mature polypeptide" means a polypeptide in its final form following translation and any post-translational modifications, such as N-terminal processing, C-terminal truncation, glycosylation, phosphorylation, etc.

The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used, it is intended to include the broader term textiles as well.

The term "variant" means a polypeptide having the activity of the parent or precursor polypeptide and comprising an alteration, i.e., a substitution, insertion, and/or deletion, at one or more positions compared to the precursor or parent polypeptide. A substitution means replacement of the amino acid occupying a position with a different amino acid; a deletion means removal of the amino acid occupying a position; and an insertion means adding an amino acid adjacent to and immediately following the amino acid occupying a position.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 6.6.0 or later. The parameters used are a gap open penalty of 10, a gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment−Total Number of Gaps in Alignment)

Nomenclature: For purposes of the present invention, the nomenclature [E/Q] means that the amino acid at this position may be a glutamic acid (Glu, E) or a glutamine (Gln, Q). Likewise, the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

For an amino acid substitution, the following nomenclature is used: Original amino acid, position, substituted amino acid. For example, the substitution of a threonine at position 220 with alanine is designated as "T220A". Multiple substitutions may be separated by addition marks ("+"), e.g., "T220A+G229V", representing substitutions at positions 220 and 229 of threonine (T) with alanine (A) and glycine (G) with valine (V), respectively. Multiple substitutions may alternatively be listed with individual mutations separated by a space or a comma. Alternative substitutions in a particular position may be indicated with a slash ("/"). For example, substitution of threonine in position 220 with either alanine, valine or leucine many be designated "T220A/V/L".

The invention is further disclosed in the following non-limited examples.

EXAMPLES

Assays

Assay I: Testing of Protease Activity

Proteolytic activity can be determined by a method employing Suc-AAPF-PNA as the substrate. Suc-AAPF- PNA is an abbreviation for N-Succinyl-Alanine-Alanine-Proline-Phenylalanine-p-Nitroanilide, and is a blocked peptide which can be cleaved by endo-proteases. Following cleavage a free PNA molecule is liberated, which has a yellow color and thus can be measured by visible spectrophotometry at wavelength 405 nm. The Suc-AAPF-PNA substrate is manufactured by Bachem (cat. no. L1400, dissolved in DMSO). The protease sample to be analyzed is diluted in residual activity buffer (100 mM Tris pH 8.6). The assay is performed by transferring 30 μl of diluted enzyme samples to 96 well microtiter plate and adding 70 μl substrate working solution (0.72 mg/ml in 100 mM Tris pH8.6). The solution was mixed at room temperature and absorption is measured every 20 seconds over 5 minutes at OD 405 nm. The slope (absorbance per minute) of the time dependent absorption-curve is directly proportional to the activity of the protease in question under the given set of conditions. The protease sample is diluted to a level where the slope is linear.

Assay II: Testing of Hexosaminidase Activity

The hexosaminidase activity may be determined using 4-nitrophenyl N-acetyl-β-D-glucosaminide (Sigma-Aldrich) as substrate. The enzymatic reaction is performed in triplicate in a 96 well flat bottom polystyrene microtiter plate (Thermo Scientific) with the following conditions: 50 mM 2-(N-morpholino)ethanesulfonic acid pH 6 buffer, 1.5 mg/ml 4-nitrophenyl N-acetyl-β-D-glucosaminide and 20 μg/ml purified enzyme sample in a total reaction volume of 100 μl. Blank samples without polypeptide are run in parallel. The reactions are carried out at 37° C. in a Thermomixer comfort (Eppendorf). After 10 minutes of incubation, 5 μl 1 M NaOH is added to each reaction mixture to stop the enzymatic reaction. The absorbance is read at 405 nm using a POLARstar Omega plate reader (BMG LABTECH) to estimate the formation of 4-nitrophenolate ion released due to enzymatic hydrolysis of the 4-nitrophenyl N-acetyl-β-D-glucosaminide substrate.

Example 1

Synergistic Effect Between a Dispersin and Proteases on Deep-Cleaning in Liquid Model Detergent on EPS Swatches A PNAG-producing *Pseudomonas fluorescens* isolate was used as a model microorganism in the present example. The strain was restreaked on Tryptone Soya Agar (TSA) (pH 7.3) (CM0131; Oxoid Ltd, Basingstoke, UK) and incubated at 23° C. A pre-culture was then established in TSB (grown for 16 h at 30° C., 200 ppm), and used to inoculate biofilm cultures in TSBG (Tryptic soy broth with 1% glucose) in sterile 6-well microplates (Thermo Scientific, #150239). The biofilm cultures were incubated statically for 3 days at 30° C. prior to harvesting. The biofilm cultures were subsequently retrieved and pelleted by centrifugation (10 min, 8000 g, 21° C.), resuspended in 3M NaCl and incubated for 15 min at 30° C. Then cells were then pelleted again, resuspended in 3M NaCl and incubated for 15 min at 30° C. The EPS-containing supernatants obtained after a final centrifugation step (10 min, 8000 g, 21° C.) were pooled and stored at −20° C. until further use (termed crude EPS).

For testing wash performance, 50 ul aliquots of the crude EPS were spotted on sterile textile swatches (WFK20A, Wfk Testgewebe GmbH, Germany) and incubated for 15 min at ambient temperature. The swatches (sterile or with EPS) were placed in 50 mL test tubes and 10 mL of wash liquor (15°dH water with 0.7 g/L WFK 09V pigment soil (Wfk Testgewebe GmbH, #00500) and 3.33 g/L liquid model A detergent (12% LAS, 11% AEO Biosoft N25-7 (NI), 5% AEOS (SLES), 6% MPG (monopropylene glycol), 3% ethanol, 3% TEA, 2.75% coco soap, 2.75% soya soap, 2% glycerol, 2% sodium hydroxide, 2% sodium citrate, 1% sodium formate, 0.2% DTMPA and 0.2% PCA (copoly (acrylic acid/maleic acid) (all percentages are w/w))) and 0.02 μg/ml dispersin (SEQ ID NO: 17) and/or 0.02 μg/ml protease (either Savinase®, SEQ ID NO: 24, or BPN', SEQ ID NO: 25) was added to each tube. Washes without enzyme were included as controls. The test tubes were placed in a Stuart rotator and incubated for 1 hour at 30° C. at 20 rpm. The wash liquor was then removed, and the swatches were rinsed twice with 15°dH water and dried on filter paper over night. The remission ($REM^{460nm}$) values, measured using a Datacolor 800V spectrophotometer, are displayed in Table 1 below. Delta values ($REM^{460nm}_{(swatches\ washed\ with\ enzyme)}-REM^{460nm}_{(swatches\ washed\ without\ enzyme)}$) and the wash performance synergies, $WP_{synergy\ synergy}$ ($\Delta REM^{460nm}_{(cocktail)}-\Delta REM^{460nm}_{(sum\ of\ individual\ enzyme\ treatments)}$) are also indicated.

TABLE 1

Synergistic effect of dispersin and protease on cleaning in model A detergent on EPS swatches.

| Swatch | Enzyme concentration (μg/ml) | Average Rem460 nm | WP (delta Rem460 nm) | $WP_{syn}$ |
|---|---|---|---|---|
| WFK20A, clean textile | 0 | 77.1 | | |
| *P. fluorescens* EPS, no enzyme | 0.02 | 31.4 | | |
| *P. fluorescens* EPS, dispersin (SEQ ID NO: 17) | 0.02 | 48.9 | 17.5 | |
| *P. fluorescens* EPS, protease (SEQ ID NO: 25) | 0.02 | 34.7 | 3.3 | |
| *P. fluorescens* EPS, protease (SEQ ID NO: 24) | 0.02 | 32.6 | 1.2 | |
| *P. fluorescens* EPS, dispersin (SEQ ID NO: 17) + protease (SEQ ID NO: 25) | 0.02 + 0.02 | 55.3 | 23.9 | 3.1 |
| *P. fluorescens* EPS, dispersin (SEQ ID NO: 17) + protease (SEQ ID NO: 24) | 0.02 + 0.02 | 54.5 | 23.1 | 4.4 |

As seen in Table 1, an enzyme cocktail comprising dispersin and a protease provides superior deep-cleaning cleaning properties in model A detergent as compared to the individual enzymes. Given that the wash performance of the enzyme cocktail (WP (cocktail)) exceeds the sum of the performances seen for of the individual enzymes (WP (enzyme 1)+WP (enzyme 2)), i.e. $WP_{syn}>0$, this suggests that there is a synergistic effect between the two enzymes on the deep-cleaning properties in model A. This could suggest that the different EPS components targeted by these enzymes are localized in complex macromolecular structures, which shield each other from enzymatic hydrolysis, and that the individual enzymes can increase the accessibility to other biofilm components, either by exposing shielded target substances or by allowing an increased penetration of the other enzyme into the biofilm matrix.

The invention claimed is:

1. A composition, comprising:

a cleaning composition with a dispersin and a protease;

wherein the dispersin comprises a polypeptide with at least 90% conservative sequence identity to SEQ ID NO: 17;

wherein the protease has at least 90% conservative sequence identity to the amino acid sequence shown in SEQ ID NO: 24, SEQ ID NO: 25, or SEQ ID NO: 26;

wherein the amount of dispersin in the composition ranges from 0.01 to 1000 ppm, and wherein the amount of protease ranges from 0.01 to 1000 ppm; and, wherein the cleaning composition exhibits a synergistic effect on the removal of protein and polysaccharide biofilms when measured using remission values taken at 460 nm.

2. The cleaning composition according to claim 1, wherein the dispersin is obtained from *Terribacillus, Curtobacterium, Aggregatibacter, Haemophilus, Actinobacillus, Lactobacillus, Staphylococcus, Neisseria, Otariodibacter, Lactococcus, Frigoribacterium, Basfia, Weissella, Macrococcus*, or *Leuconostoc.*

3. The composition according to claim 1, wherein the dispersin catalyzes the hydrolysis of β-1,6-glycosidic linkages of N-acetyl-glucosamine polymers.

4. The composition according to claim 1, wherein the amount of dispersin in the composition ranges from 0.01 to 0.03 ppm, and wherein the amount of protease ranges from 0.01 to 0.03 ppm.

5. The composition according to claim 1, wherein said composition:

(a) is a solid, and further comprises
(a1) at least one zeolite builder;
(a2) at least one phosphonate builder;
(a3) at least one further enzyme; and
(a4) at least one polymer; or (b) is a solid laundry detergent composition and further comprises
(b1) at least one silicate builder;
(b2) optionally carboxymethylcellulose;
(b3) at least one further enzyme;
(b4) optionally at least one soil release polymer in an amount of 0.1 to 3 wt; and
(b5) at least one bleaching system, comprising a bleaching agent, a bleach activator and a bleach catalyst; or (c) is liquid laundry detergent composition and further comprises
(c1) at least one surfactant;
(c2) optionally at least one phosphonate builder
(c3) optionally at least one further enzyme; and
(c4) optionally at least one organic solvent; or (d) is a liquid laundry detergent in unit dose form, and further comprises
(d1) water in an amount of up to 20 wt;
(d2) optionally at least one bittering agent;
(d3) optionally at least one optical brightener; and
(d4) optionally at least one polymer; or (e) is a fabric finisher and further comprises
(e1) at least one softening silicone;
(e2) at least one perfume;
(e3) optionally polyquaternium 10 in an amount ranging from 0.1 to 20 wt;
(e4) optionally polyquaternium 37 in an amount ranging from 0.1 to 20 wt;
(e5) optionally a plant-based esterquat; and
(e6) optionally adipic acid, in an amount ranging from 0.1 to 20 wt; or (f) is an acidic cleaning agent, and further comprises
(f1) plant-based or bio-based surfactants;
(f2) at least one acidic biocide; and
(f3) at least one soil release, water repellant, or water spreading polymer; or (g) is a neutral cleaning agent, and further comprises
(g1) plant-based or bio-based surfactants;
(g2) at least one biocide; and
(g3) at least one soil release, water repellant, or water spreading polymer; or (h) is an alkaline cleaning agent, and further comprises
(h1) plant-based or bio-based surfactants; or (i) is a hand dishwashing agent, and further comprises
(i1) at least one anionic surfactant;
(i2) at least one amphoteric surfactant;
(i3) at least one nonionic surfactant;
(i4) at least one further enzyme; or (j) is an automatic dishwashing composition and further comprises
(j1) at least one builder selected from citrate, aminocarboxylates, and combinations thereof;
(j2) at least one phosphonate builder;
(j3) at least one nonionic surfactant;
(j4) at least one bleaching system, comprising a bleaching agent, a bleach activator, and a bleach catalyst;
(j5) at least one polymer selected from sulfopolymers, cationic polymers, and polyacrylates; or (k) further comprises
(k1) at least one sulfopolymer; or (l) further comprises at least one adjunct ingredient selected from probiotics; or (m) is in unit dose form, and comprises at least 2 separate compartments; or (n) is a phosphate-free composition.

6. The composition of claim 1 wherein the protein and polysaccharide biofilm is a poly-β(1-6)-N-acetylglucosamine) (PNAG) containing biofilm.

7. The composition of claim 1 wherein the ratio of the concentration of the dispersin to the protease is 1:1.

8. A method, comprising:

a) contacting an item with a cleaning composition according to claim 1; and, b) rinsing the item;

wherein the item is a textile.

* * * * *

SEQUENCE LISTING

```
<160> NUMBER OF SEQ ID NOS: 31

<210> SEQ ID NO 1
<211> LENGTH: 359
<212> TYPE: PRT
<213> ORGANISM: Aggregatibacter actinomycetemcomitans

<400> SEQUENCE: 1

Cys Val Lys Gly Asn Ser Ile His Pro Gln Lys Thr Ser Thr Lys Gln
1               5                   10                  15

Thr Gly Leu Met Leu Asp Ile Ala Arg His Phe Tyr Ser Pro Glu Val
            20                  25                  30

Ile Lys Ser Phe Ile Asp Thr Ile Ser Leu Ser Gly Gly Asn Phe Leu
        35                  40                  45

His Leu His Phe Ser Asp His Glu Asn Tyr Ala Ile Glu Ser His Leu
    50                  55                  60

Leu Asn Gln Arg Ala Glu Asn Ala Val Gln Gly Lys Asp Gly Ile Tyr
65                  70                  75                  80

Ile Asn Pro Tyr Thr Gly Lys Pro Phe Leu Ser Tyr Arg Gln Leu Asp
                85                  90                  95

Asp Ile Lys Ala Tyr Ala Lys Ala Lys Gly Ile Glu Leu Ile Pro Glu
            100                 105                 110

Leu Asp Ser Pro Asn His Met Thr Ala Ile Phe Lys Leu Val Gln Lys
        115                 120                 125

Asp Arg Gly Ile Lys Tyr Leu Gln Gly Leu Lys Ser Arg Gln Val Asp
    130                 135                 140

Asp Glu Ile Asp Ile Thr Asn Ala Asp Ser Ile Ala Phe Met Gln Ser
145                 150                 155                 160

Leu Met Ser Glu Val Ile Asp Ile Phe Gly Asp Thr Ser Gln His Phe
                165                 170                 175

His Ile Gly Gly Asp Glu Phe Gly Tyr Ser Val Glu Ser Asn His Glu
            180                 185                 190

Phe Ile Thr Tyr Ala Asn Lys Leu Ser Tyr Phe Leu Glu Lys Lys Gly
        195                 200                 205

Leu Lys Thr Arg Met Trp Asn Asp Gly Leu Ile Lys Ser Thr Phe Glu
    210                 215                 220

Gln Ile Asn Pro Asn Ile Glu Ile Thr Tyr Trp Ser Tyr Asp Gly Asp
225                 230                 235                 240

Thr Gln Asp Lys Asn Glu Ala Ala Glu Arg Arg Asp Met Arg Val Ser
                245                 250                 255

Leu Pro Glu Leu Leu Ala Lys Gly Phe Thr Val Leu Asn Tyr Asn Ser
            260                 265                 270

Tyr Tyr Leu Tyr Ile Val Pro Lys Ala Ser Pro Thr Phe Ser Gln Asp
        275                 280                 285

Ala Ala Phe Ala Ala Lys Asp Val Ile Lys Asn Trp Asp Leu Gly Val
    290                 295                 300

Trp Asp Gly Arg Asn Thr Lys Asn Arg Val Gln Asn Thr His Glu Ile
305                 310                 315                 320
```

```
Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
            340                 345                 350

His Lys Ala Asn Gly Asp Glu
        355


<210> SEQ ID NO 2
<211> LENGTH: 346
<212> TYPE: PRT
<213> ORGANISM: Haemophilus sputorum

<400> SEQUENCE: 2

Gln Asn Ser Thr Lys Gln Ser Gly Leu Met Leu Asp Ile Ser Arg Arg
1               5                   10                  15

Phe Tyr Ser Val Glu Thr Ile Lys Gln Phe Ile Asp Asp Ile Ala Gln
            20                  25                  30

Ala Asn Gly Thr Phe Leu His Leu His Phe Ala Asp His Glu Asn Tyr
        35                  40                  45

Ala Leu Glu Ser Thr Phe Leu Asn Gln Arg Ala Glu Asn Ala Ile Val
    50                  55                  60

Gln Asn Gly Ile Tyr Ile Asn Pro Lys Thr Asn Lys Pro Phe Leu Thr
65                  70                  75                  80

Tyr Glu Gln Ile Asp Gln Ile Ile Arg Tyr Ala Gln Glu Lys Gln Ile
                85                  90                  95

Glu Leu Ile Pro Glu Val Asp Ser Pro Ala His Ile Lys Gly Ile Leu
            100                 105                 110

Thr Leu Leu Arg Leu Glu Lys Gly Glu Asp Tyr Val Asn Gln Ile Ala
        115                 120                 125

Leu Asn Gln Asp Glu Leu Asn Leu Asp Ser Pro Glu Ser Leu Thr Met
    130                 135                 140

Met Lys Thr Leu Val Asp Glu Val Cys Tyr Ile Phe Gly Tyr Ser Ala
145                 150                 155                 160

Gln His Phe His Ile Gly Gly Asp Glu Phe Asn Tyr Ala Ser Asn Phe
                165                 170                 175

Ile Arg Tyr Val Asn Ala Leu Asn Gln His Ile Asn Gln Lys Gly Leu
            180                 185                 190

Ile Thr Arg Met Trp Asn Asp Gly Leu Leu Gln Gln Asn Ile Asp Glu
        195                 200                 205

Leu Asp Lys Asn Ile Glu Ile Thr Tyr Trp Ser Phe Asp Gly Asp Ala
    210                 215                 220

Gln Glu Lys Asn Asp Ile Val Glu Arg Arg Ala Thr Arg Ile Ser Leu
225                 230                 235                 240

Pro Thr Leu Leu Asp Lys Gly Phe Lys Ala Leu Asn Tyr Asn Ser Tyr
                245                 250                 255

Tyr Leu Tyr Phe Ile Pro Lys Asp Asn Gly Asn Ile Ala Thr Asp Ala
            260                 265                 270

Lys Phe Ala Leu Asn Asp Leu Lys Gln Asn Trp Gln Leu Leu Arg Trp
        275                 280                 285

Asp Gly Asn Tyr Glu Thr Gln Pro Ile Gln Gln Ala Glu Asn Leu Ile
    290                 295                 300

Gly Ala Ala Phe Ser Ile Trp Gly Glu His Ala Gly Lys Leu Ser Asp
305                 310                 315                 320

Asp Val Ile His Gln Ala Thr Ser Pro Leu Ile Gln Ala Thr Ile Ile
```

```
                325                 330                 335

Gln Thr Asn Ala Lys Thr Thr Gly Pro Asn
            340                 345


<210> SEQ ID NO 3
<211> LENGTH: 352
<212> TYPE: PRT
<213> ORGANISM: Actinobacillus suis

<400> SEQUENCE: 3

Met Asn His Ser Gln Ile Lys Glu Ala Gly Leu Thr Leu Asp Ile Ala
1               5                   10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
        35                  40                  45

Asn Tyr Ala Leu Glu Ser Thr Tyr Leu Asp Gln Ser Glu Ala Asn Ala
    50                  55                  60

Ile Val Lys Asp Gly Thr Tyr Tyr Asn Pro Lys Thr Asn Lys Pro Phe
65                  70                  75                  80

Leu Thr Tyr Lys Gln Ile His Asp Ile Ile Tyr Tyr Ala Lys Ser Lys
                85                  90                  95

Asn Ile Glu Leu Val Pro Glu Val Asp Thr Pro Asn His Met Thr Ala
            100                 105                 110

Ile Phe Arg Leu Leu Glu Ala Lys His Gly Lys Asp Tyr Val Lys Lys
        115                 120                 125

Leu Lys Ser Lys Met Asn Asp Glu Glu Ile Asp Ile Thr Asn Pro Glu
    130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
                165                 170                 175

Ser Val Glu Thr Asn His Glu Phe Ile Ser Tyr Val Asn Thr Leu Asn
            180                 185                 190

Gln Phe Ile Asn Glu Lys Gly Lys Ile Thr Arg Ile Trp Asn Asp Gly
        195                 200                 205

Leu Ile Lys Asn Asn Leu Asn Gln Leu Asn Lys Asn Val Glu Ile Thr
    210                 215                 220

Tyr Trp Ser Tyr Asp Gly Asp Ala Gln Glu Ser Gln Asp Ile Ala Glu
225                 230                 235                 240

Arg Arg Lys Ile Arg Ala Asn Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys Tyr Ala Thr Glu Asp Val Leu
        275                 280                 285

Asn Asn Trp Lys Leu Gly Leu Trp Asp Gly Gln Asn Lys Glu Asn Met
    290                 295                 300

Val Glu Asn Thr Lys Asn Ile Ile Gly Ser Ser Leu Ser Ile Trp Gly
305                 310                 315                 320

Glu Arg Ser Gly Ser Leu Ser Ser Glu Val Ile Glu Glu Ser Thr Gln
                325                 330                 335

Asp Leu Leu Lys Ala Val Ile Gln Lys Thr Asn Asp Pro Lys Ser His
            340                 345                 350
```

<210> SEQ ID NO 4
<211> LENGTH: 352
<212> TYPE: PRT
<213> ORGANISM: Actinobacillus capsulatus

<400> SEQUENCE: 4

```
Met Asn His Ser Gln Ile Lys Glu Ala Gly Leu Thr Leu Asp Ile Ala
1               5                   10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
        35                  40                  45

Asn Tyr Ala Leu Glu Ser Thr Tyr Leu Asp Gln Leu Glu Ala Asn Ala
    50                  55                  60

Ile Val Lys Asp Gly Thr Tyr Tyr Asn Pro Thr Thr Asn Lys Pro Phe
65                  70                  75                  80

Leu Thr Tyr Lys Gln Ile Asn Asp Ile Ile Tyr Tyr Ala Lys Ser Lys
                85                  90                  95

Asn Ile Glu Leu Val Pro Glu Val Asp Thr Pro Asn His Met Thr Ala
            100                 105                 110

Ile Phe Arg Leu Leu Glu Ala Lys His Ser Lys Asp Tyr Val Lys Arg
        115                 120                 125

Leu Lys Ser Lys Met Asn Asp Glu Glu Ile Asp Ile Thr Asn Leu Glu
    130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
                165                 170                 175

Ser Val Glu Thr Asn His Glu Phe Ile Thr Tyr Val Asn Thr Leu Asn
            180                 185                 190

Gln Phe Ile Asn Asn Lys Gly Lys Ile Thr Arg Ile Trp Asn Asp Gly
        195                 200                 205

Leu Ile Lys Asn Asn Leu Asn Gln Leu Asn Lys Asn Val Glu Ile Thr
    210                 215                 220

Tyr Trp Ser Tyr Asp Gly Asp Ala Gln Glu Ser Gln Asp Ile Ala Glu
225                 230                 235                 240

Arg Arg Lys Ile Arg Val Asn Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys His Ala Thr Glu Asp Val Leu
        275                 280                 285

Lys Asn Trp Lys Leu Gly Leu Trp Asp Gly Gln Asn Lys Glu Asn Ile
    290                 295                 300

Val Glu Asn Thr Lys Asn Ile Ile Gly Ser Ser Leu Ser Ile Trp Gly
305                 310                 315                 320

Glu His Ser Gly Ser Leu Ser Ser Ala Val Ile Glu Glu Ser Thr Gln
                325                 330                 335

Glu Leu Leu Lys Ala Val Ile Gln Lys Thr Asn Asp Pro Lys Ser His
            340                 345                 350
```

<210> SEQ ID NO 5
<211> LENGTH: 352
<212> TYPE: PRT
<213> ORGANISM: Actinobacillus equuli

<400> SEQUENCE: 5

Met Asn His Ser Gln Ile Lys Glu Ala Gly Leu Thr Leu Asp Ile Ala
1               5                   10                  15

Arg Arg Phe Tyr Pro Val Glu Thr Ile Lys Gln Phe Ile Asp Thr Ile
            20                  25                  30

His His Ala Gly Gly Thr Phe Leu His Leu His Phe Ser Asp His Glu
        35                  40                  45

Asn Tyr Ala Leu Glu Ser Ser Tyr Leu Asp Gln Ser Glu Glu Asn Ala
    50                  55                  60

Ile Val Lys Asp Gly Thr Tyr Tyr Asn Pro Lys Thr Asn Lys Pro Phe
65                  70                  75                  80

Leu Thr Tyr Lys Gln Ile Asp Asp Ile Ile Tyr Tyr Ala Lys Ser Lys
                85                  90                  95

Asn Ile Glu Leu Val Pro Glu Val Asp Thr Pro Asn His Met Thr Ala
            100                 105                 110

Ile Phe Asn Leu Leu Glu Ile Lys His Gly Glu Ala Tyr Val Lys Asn
        115                 120                 125

Leu Lys Ser Lys Met Asn Asp Glu Glu Ile Asp Ile Thr Asn Pro Glu
    130                 135                 140

Ser Ile Glu Val Ile Lys Thr Leu Ile Ala Glu Val Ile Tyr Ile Phe
145                 150                 155                 160

Gly His Ala Ser Glu His Phe His Ile Gly Gly Asp Glu Phe Gly Tyr
                165                 170                 175

Ser Val Glu Thr Asn His Glu Phe Ile Ser Tyr Val Asn Thr Leu Asn
            180                 185                 190

Gln Phe Ile Asn Glu Lys Gly Lys Ile Thr Arg Ile Trp Asn Asp Gly
        195                 200                 205

Leu Ile Lys Asn Asn Leu Asn Gln Leu Asn Lys Asn Val Glu Ile Thr
    210                 215                 220

Tyr Trp Ser Tyr Asp Gly Asp Ala Gln Lys Ser Gln Asp Ile Ala Glu
225                 230                 235                 240

Arg Arg Lys Ile Arg Ala Asp Leu Pro Glu Leu Leu Glu Asn Gly Phe
                245                 250                 255

Lys Val Leu Asn Tyr Asn Ser Tyr Tyr Leu Tyr Phe Val Pro Lys Gly
            260                 265                 270

Asn Ala Asn Ile Thr His Asp Ser Lys Tyr Ala Thr Glu Asp Val Leu
        275                 280                 285

Asn Asn Trp Lys Leu Gly Leu Trp Asp Gly Lys Asn Lys Glu Asn Glu
    290                 295                 300

Val Lys Asn Thr Lys Asn Ile Ile Gly Ser Ser Leu Ser Ile Trp Gly
305                 310                 315                 320

Glu Arg Ser Gly Ser Leu Ser Ser Glu Val Ile Glu Glu Ser Thr Gln
                325                 330                 335

Asp Leu Leu Lys Ala Val Ile Gln Lys Thr Asn Asp Pro Lys Ser His
            340                 345                 350

<210> SEQ ID NO 6
<211> LENGTH: 359
<212> TYPE: PRT
<213> ORGANISM: Aggregatibacter actinomycetemcomitans

<400> SEQUENCE: 6

Cys Val Lys Gly Asn Ser Ile Tyr Pro Gln Lys Ile Ser Thr Lys Gln
1               5                   10                  15

```
Thr Gly Leu Met Leu Asp Ile Ala Arg His Phe Tyr Ser Pro Glu Val
            20                  25                  30

Ile Lys Ser Phe Ile Asp Thr Ile Ser Leu Ser Gly Gly Asn Phe Leu
        35                  40                  45

His Leu His Phe Ser Asp His Glu Asn Tyr Ala Ile Glu Ser His Leu
    50                  55                  60

Leu Asn Gln Arg Ala Glu Asn Ala Val Gln Gly Lys Asp Gly Ile Tyr
65                  70                  75                  80

Ile Asn Pro Tyr Thr Gly Lys Pro Phe Leu Ser Tyr Arg Gln Leu Asp
                85                  90                  95

Asp Ile Lys Ala Tyr Ala Lys Ala Lys Gly Ile Glu Leu Ile Pro Glu
            100                 105                 110

Leu Asp Ser Pro Asn His Met Thr Ala Ile Phe Lys Leu Val Gln Lys
        115                 120                 125

Asp Arg Gly Val Lys Tyr Leu Gln Gly Leu Lys Ser Arg Gln Val Asp
    130                 135                 140

Asp Glu Ile Asp Ile Thr Asn Ala Asp Ser Ile Ala Phe Met Gln Ser
145                 150                 155                 160

Leu Met Asn Glu Val Ile Asp Ile Phe Gly Asp Thr Ser Gln His Phe
                165                 170                 175

His Ile Gly Gly Asp Glu Phe Gly Tyr Ser Val Glu Ser Asn His Glu
            180                 185                 190

Phe Ile Thr Tyr Ala Asn Lys Leu Ser Tyr Phe Leu Glu Lys Lys Gly
        195                 200                 205

Leu Lys Thr Arg Met Trp Asn Asp Gly Leu Ile Lys Ser Thr Phe Glu
    210                 215                 220

Gln Ile Asn Pro Asn Ile Glu Ile Thr Tyr Trp Ser Tyr Asp Gly Asp
225                 230                 235                 240

Thr Gln Asp Lys Asn Glu Ala Ala Glu Arg Arg Asp Met Arg Val Ser
                245                 250                 255

Leu Pro Glu Leu Leu Ala Lys Gly Phe Thr Val Leu Asn Tyr Asn Ser
            260                 265                 270

Tyr Tyr Leu Tyr Ile Val Pro Lys Ala Ser Pro Thr Phe Ser Gln Asp
        275                 280                 285

Ala Ala Phe Ala Ala Lys Asp Val Ile Lys Asn Trp Asp Leu Gly Val
    290                 295                 300

Trp Asp Gly Arg Asn Thr Lys Asn Arg Val Gln Asn Thr His Glu Ile
305                 310                 315                 320

Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
            340                 345                 350

His Lys Thr Asn Gly Asp Glu
        355
```

<210> SEQ ID NO 7
<211> LENGTH: 359
<212> TYPE: PRT
<213> ORGANISM: Aggregatibacter actinomycetemcomitans

<400> SEQUENCE: 7

```
Cys Val Lys Gly Asn Ser Ile Tyr Pro Gln Lys Thr Ser Thr Lys Gln
1               5                   10                  15

Thr Gly Leu Met Leu Asp Ile Ala Arg His Phe Tyr Ser Pro Glu Val
```

```
            20                  25                  30

Ile Lys Ser Phe Ile Asp Thr Ile Ser Leu Ser Gly Gly Asn Phe Leu
        35                  40                  45

His Leu His Phe Ser Asp His Glu Asn Tyr Ala Ile Glu Ser His Leu
    50                  55                  60

Leu Asn Gln Arg Ala Glu Asn Ala Val Gln Gly Lys Asp Gly Ile Tyr
65                  70                  75                  80

Ile Asn Pro Tyr Thr Gly Lys Pro Phe Leu Ser Tyr Arg Gln Leu Asp
                85                  90                  95

Asp Ile Lys Ala Tyr Ala Lys Ala Lys Gly Ile Glu Leu Ile Pro Glu
            100                 105                 110

Leu Asp Ser Pro Asn His Met Thr Ala Ile Phe Lys Leu Val Gln Lys
        115                 120                 125

Asp Arg Gly Val Lys Tyr Leu Gln Gly Leu Lys Ser Arg Gln Val Asp
    130                 135                 140

Asp Glu Ile Asp Ile Thr Asn Ala Asp Ser Ile Thr Phe Met Gln Ser
145                 150                 155                 160

Leu Met Ser Glu Val Ile Asp Ile Phe Gly Asp Thr Ser Gln His Phe
                165                 170                 175

His Ile Gly Gly Asp Glu Phe Gly Tyr Ser Val Glu Ser Asn His Glu
            180                 185                 190

Phe Ile Thr Tyr Ala Asn Lys Leu Ser Tyr Phe Leu Glu Lys Lys Gly
        195                 200                 205

Leu Lys Thr Arg Met Trp Asn Asp Gly Leu Ile Lys Asn Thr Phe Glu
    210                 215                 220

Gln Ile Asn Pro Asn Ile Glu Ile Thr Tyr Trp Ser Tyr Asp Gly Asp
225                 230                 235                 240

Thr Gln Asp Lys Asn Glu Ala Ala Glu Arg Arg Asp Met Arg Val Ser
                245                 250                 255

Leu Pro Glu Leu Leu Ala Lys Gly Phe Thr Val Leu Asn Tyr Asn Ser
            260                 265                 270

Tyr Tyr Leu Tyr Ile Val Pro Lys Ala Ser Pro Thr Phe Ser Gln Asp
        275                 280                 285

Ala Ala Phe Ala Ala Lys Asp Val Ile Lys Asn Trp Asp Leu Gly Val
    290                 295                 300

Trp Asp Gly Arg Asn Thr Lys Asn Arg Val Gln Asn Thr His Glu Ile
305                 310                 315                 320

Ala Gly Ala Ala Leu Ser Ile Trp Gly Glu Asp Ala Lys Ala Leu Lys
                325                 330                 335

Asp Glu Thr Ile Gln Lys Asn Thr Lys Ser Leu Leu Glu Ala Val Ile
            340                 345                 350

His Lys Thr Asn Gly Asp Glu
        355


<210> SEQ ID NO 8
<211> LENGTH: 351
<212> TYPE: PRT
<213> ORGANISM: Actinobacillus pleuropneumoniae

<400> SEQUENCE: 8

Met Asp Leu Pro Lys Lys Glu Ser Gly Leu Thr Leu Asp Ile Ala Arg
1               5                   10                  15

Arg Phe Tyr Thr Val Asp Thr Ile Lys Gln Phe Ile Asp Thr Ile His
            20                  25                  30
```

-continued

```
Gln Ala Gly Gly Thr Phe Leu His Leu His Phe Ser Asp His Glu Asn
        35                  40                  45

Tyr Ala Leu Glu Ser Ser Tyr Leu Glu Gln Arg Glu Glu Asn Ala Thr
    50                  55                  60

Glu Lys Asn Gly Thr Tyr Phe Asn Pro Lys Thr Asn Lys Pro Phe Leu
65                  70                  75                  80

Thr Tyr Lys Gln Leu Asn Glu Ile Ile Tyr Tyr Ala Lys Glu Arg Asn
                85                  90                  95

Ile Glu Ile Val Pro Glu Val Asp Ser Pro Asn His Met Thr Ala Ile
            100                 105                 110

Phe Asp Leu Leu Thr Leu Lys His Gly Lys Glu Tyr Val Lys Gly Leu
        115                 120                 125

Lys Ser Pro Tyr Ile Ala Glu Glu Ile Asp Ile Asn Asn Pro Glu Ala
    130                 135                 140

Val Glu Val Ile Lys Thr Leu Ile Gly Glu Val Ile Tyr Ile Phe Gly
145                 150                 155                 160

His Ser Ser Arg His Phe His Ile Gly Gly Asp Glu Phe Ser Tyr Ala
                165                 170                 175

Val Glu Asn Asn His Glu Phe Ile Arg Tyr Val Asn Thr Leu Asn Asp
            180                 185                 190

Phe Ile Asn Ser Lys Gly Leu Ile Thr Arg Val Trp Asn Asp Gly Leu
        195                 200                 205

Ile Lys Asn Asn Leu Ser Glu Leu Asn Lys Asn Ile Glu Ile Thr Tyr
    210                 215                 220

Trp Ser Tyr Asp Gly Asp Ala Gln Ala Lys Glu Asp Ile Gln Tyr Arg
225                 230                 235                 240

Arg Glu Ile Arg Ala Asp Leu Pro Glu Leu Leu Ala Asn Gly Phe Lys
                245                 250                 255

Val Leu Asn Tyr Asn Ser Tyr Tyr Leu Tyr Phe Val Pro Lys Ser Gly
            260                 265                 270

Ser Asn Ile His Asn Asp Gly Lys Tyr Ala Ala Glu Asp Val Leu Asn
        275                 280                 285

Asn Trp Thr Leu Gly Lys Trp Asp Gly Lys Asn Ser Ser Asn His Val
    290                 295                 300

Gln Asn Thr Gln Asn Ile Ile Gly Ser Ser Leu Ser Ile Trp Gly Glu
305                 310                 315                 320

Arg Ser Ser Ala Leu Asn Glu Gln Thr Ile Gln Gln Ala Ser Lys Asn
                325                 330                 335

Leu Leu Lys Ala Val Ile Gln Lys Thr Asn Asp Pro Lys Ser His
            340                 345                 350


<210> SEQ ID NO 9
<211> LENGTH: 461
<212> TYPE: PRT
<213> ORGANISM: Curtobacterium oceanosedimentum

<400> SEQUENCE: 9

Ala Asp Arg Asn Thr Ser Ala Ala Glu Ala Ala Val Thr Ser Ile Ala
1               5                   10                  15

Pro Arg Ala Thr Ile Thr Gly Val Ala Ala Ile Ser Ala Ala Thr Ser
            20                  25                  30

Ser Arg Thr Thr Val Arg Thr Thr Leu Thr Leu Glu Asn Arg Ser Gly
        35                  40                  45

Glu Arg Glu Ser Ala Ala Asp Ala Trp Leu Tyr Leu Ala Gly Gly Gly
    50                  55                  60
```

```
Ala Arg Tyr Ala Leu Gly His Ala Pro Val Arg Ala Leu Ala Ala Gly
65                  70                  75                  80

Ala Arg Ala Thr Val Arg Thr Thr Leu Arg Val Pro Ser Arg Ala Pro
                85                  90                  95

Ala Gly Lys Tyr Ala Val Leu Ala Cys Ala Gly Pro Tyr Ser Lys Gln
            100                 105                 110

Ala Cys Arg Thr Ser Gly Thr Thr Val Thr Val Gly Thr Ala Ala Arg
        115                 120                 125

Ala Arg Pro Glu Thr Gly Val Met Leu Asp Val Ala Arg Ala Tyr Tyr
    130                 135                 140

Pro Val Ser Leu Ile Glu Gln Tyr Val Asp Leu Leu Ala Glu His Gly
145                 150                 155                 160

Gly Gly Phe Leu His Leu His Leu Thr Asp Asp Gln Asn Val Gly Ile
                165                 170                 175

Glu Ser Ala Val Leu Gly Gln Thr Pro Ala Asn Ala Val Leu Arg Asn
            180                 185                 190

Gly Val Tyr Thr Ser Arg Val Thr Gly Arg Pro Phe Leu Ser Ala Ala
        195                 200                 205

Gln Ala Arg Ala Ile Ser Ala Tyr Ala Ala Lys Arg Gly Ile Ala Ile
    210                 215                 220

Val Pro Glu Val Asp Ser Pro Gly His Met Ala Ala Ala Phe Ala Leu
225                 230                 235                 240

Leu Glu Ala Arg His Gly Ala Thr Trp Val Asp Arg Ile Arg Ser Gly
                245                 250                 255

Glu Ser Glu Leu Asp Thr Ser Val Pro Glu Ser Ala Thr Leu Ala Ala
            260                 265                 270

Glu Leu Leu Arg Glu Val Thr Gln Thr Phe Pro Ser Ser Arg Thr Val
        275                 280                 285

His Ile Gly Gly Asp Glu Trp Gly Ala Asp Val Ser Ala Asp Glu Arg
    290                 295                 300

Val Gly Trp Met Asn Ala Met Ala Ala Ala Ile Gly Asp Arg Glu Val
305                 310                 315                 320

Trp Ala Trp Asn Asp Gly Ile Asp Arg Ala Ser Val Gly Arg Leu Asp
                325                 330                 335

Pro Arg Ile His Val Thr Tyr Trp Ser Phe Asp Gly Asp Thr Glu Asp
            340                 345                 350

Ala Ala Glu Arg Arg Glu Arg Arg Ala Arg Arg Ala Ser Ala Thr Asp
        355                 360                 365

Leu Gln Arg Ala Gly Ile Asp Leu Leu Asn Tyr Asn Ser Tyr Tyr Leu
    370                 375                 380

Tyr Glu Val Pro Thr Asp Leu Asp Pro Ala Asp Ser Glu Tyr Thr Val
385                 390                 395                 400

Ala Asp Leu Arg Glu His Trp Ser Leu Arg Ala Trp Asp Gly Asp Ser
                405                 410                 415

Gly Ala Arg Leu Ala Ala Pro Met Ser Gly Ala Ala Val Ala Ile Trp
            420                 425                 430

Gly Glu Asp Leu Asp Gly Ala Pro Ser Glu Ala Leu Leu Arg Trp Ser
        435                 440                 445

Ala Pro His Val Thr Ala Met Ile Glu Thr Ala Ala Ser
    450                 455                 460
```

<210> SEQ ID NO 10
<211> LENGTH: 445

<212> TYPE: PRT
<213> ORGANISM: Curtobacterium flaccumfaciens

<400> SEQUENCE: 10

Asp Thr Ala Val Ser Ala Val Thr Val Thr Lys Val Thr Ala Ser Thr
1 5 10 15

Thr Gly Thr Val Val Arg Thr Thr Leu Lys Val Glu Asn Thr Ala Pro
20 25 30

Val Arg Lys Pro Ala Ser Ser Val Trp Leu Tyr Leu Ser Ala Gly Thr
35 40 45

Glu Lys Tyr Thr Leu Gly Arg Val Ala Val Lys Ala Leu Ala Ala Gly
50 55 60

Ser Ser Thr Ser Val Thr Ala Val Arg Gly Thr Pro Ser Arg Ala Ala
65 70 75 80

Ala Gly Lys Tyr Ser Val Leu Ala Cys Ala Gly Ala Tyr Ser Ala Lys
85 90 95

Gln Cys Arg Thr Ser Thr Ala Thr Val Thr Thr Lys Pro Thr Lys Arg
100 105 110

Ala Arg Pro Glu Thr Gly Val Met Leu Asp Val Ala Arg Ala Tyr Tyr
115 120 125

Pro Val Ala Leu Ile Lys Arg Tyr Ile Asp Leu Leu Ala Asp Asp Gly
130 135 140

Gly Arg Phe Leu His Leu His Leu Thr Asp Asp Gln Asn Val Gly Ile
145 150 155 160

Glu Ser Thr Val Leu Gly Gln Thr Pro Ala Asn Ala Asp Leu Asp His
165 170 175

Gly Val Tyr Thr Ser Arg Val Thr His Arg Pro Phe Leu Ser Ala Ala
180 185 190

Gln Ala Arg Thr Ile Ser Ala Tyr Gly Ala Glu Arg Gly Val Ala Ile
195 200 205

Val Pro Glu Ile Asp Thr Pro Gly His Met Ala Ala Ala Phe Ala Leu
210 215 220

Leu Glu Ala Gln His Gly Thr Lys Trp Val Asp Arg Ile Arg Ser Gly
225 230 235 240

Glu Asn Glu Leu Asp Thr Ser Ala Pro Glu Ser Leu Ala Leu Ala Lys
245 250 255

Lys Leu Tyr Ala Glu Val Gln Arg Thr Phe Pro Ser Ser Arg Thr Val
260 265 270

His Ile Gly Gly Asp Glu Trp Gly Asp Asp Val Thr Ala Ala Gln Arg
275 280 285

Val Thr Trp Met Asn Ala Met Ala Ala Ala Leu Asp Asp Arg Glu Val
290 295 300

Trp Ala Trp Asn Asp Gly Ile Asp Arg Val Ala Val Gly Arg Leu Asp
305 310 315 320

Pro Arg Ile His Val Thr Tyr Trp Ser Phe Asp Gly Asp Thr Glu Asp
325 330 335

Ala Ala Glu Arg Arg Glu Arg Arg Ala Arg Arg Ala Ser Ala Val Asp
340 345 350

Leu Gln Gln Ala Gly Ile Asp Gln Leu Asn Tyr Asn Ser Tyr Tyr Leu
355 360 365

Tyr Glu Val Pro Thr Asp Leu Asp Pro Ala Asp Ser Asp Tyr Thr Val
370 375 380

Ala Asp Leu Arg Glu Asn Trp Ser Leu Arg Ala Trp Asp Gly Asp Ser
385 390 395 400

```
Gly Ser Leu Leu Ala Ala Pro Met Ser Gly Ala Ala Val Ala Ile Trp
                405                 410                 415

Gly Glu Asp Leu Glu Asp Pro Pro Ser Asp Ala Leu Leu Arg Trp Ser
            420                 425                 430

Ala Pro His Val Thr Ala Met Ile Glu Thr Ala Ala Ser
        435                 440                 445


<210> SEQ ID NO 11
<211> LENGTH: 445
<212> TYPE: PRT
<213> ORGANISM: Curtobacterium luteum

<400> SEQUENCE: 11

Asp Thr Ala Val Ser Ala Val Thr Val Thr Lys Val Thr Ala Ser Thr
1               5                   10                  15

Thr Gly Thr Ala Val Arg Thr Thr Leu Lys Val Glu Asn Thr Ala Pro
            20                  25                  30

Val Arg Lys Pro Ala Ser Ser Val Trp Leu Tyr Leu Ser Ala Gly Thr
        35                  40                  45

Glu Lys Tyr Thr Leu Gly Arg Val Ala Val Lys Ala Leu Ser Ala Gly
    50                  55                  60

Ser Ser Thr Ser Val Thr Ala Val Arg Gly Thr Pro Ser Arg Ala Ala
65                  70                  75                  80

Ala Gly Lys Tyr Trp Val Leu Ala Cys Ala Gly Ala Tyr Ser Ala Lys
                85                  90                  95

Gln Cys Arg Thr Ser Thr Ala Thr Val Thr Thr Lys Pro Thr Lys Arg
            100                 105                 110

Ala Arg Pro Glu Thr Gly Val Met Leu Asp Val Ala Arg Ala Tyr Tyr
        115                 120                 125

Pro Val Ala Leu Ile Lys Arg Tyr Ile Asp Leu Leu Ala Asp Asp Gly
    130                 135                 140

Gly Arg Phe Leu His Leu His Leu Thr Asp Asp Gln Asn Val Gly Ile
145                 150                 155                 160

Glu Ser Thr Val Leu Gly Gln Thr Pro Ala Asn Ala Asp Leu Asp His
                165                 170                 175

Gly Val Tyr Thr Ser Arg Val Thr His Arg Pro Phe Leu Ser Ala Ala
            180                 185                 190

Gln Ala Arg Thr Ile Ser Glu Tyr Gly Ala Glu Arg Gly Val Thr Ile
        195                 200                 205

Val Pro Glu Ile Asp Thr Pro Gly His Met Ala Ala Ala Phe Ala Leu
    210                 215                 220

Leu Glu Ala Gln His Gly Thr Lys Trp Val Asp Arg Ile Arg Ser Gly
225                 230                 235                 240

Glu Asn Glu Leu Asp Thr Ser Ala Pro Glu Ser Leu Val Leu Ala Lys
                245                 250                 255

Lys Leu Tyr Ala Glu Val Gln Arg Thr Phe Pro Ser Ser Arg Thr Val
            260                 265                 270

His Ile Gly Gly Asp Glu Trp Gly Asp Asp Val Thr Ala Ala His Arg
        275                 280                 285

Val Ala Trp Met Asn Glu Met Ala Ala Thr Leu Gly Asn Arg Glu Val
    290                 295                 300

Trp Ala Trp Asn Asp Gly Ile Asp Arg Val Ala Val Gly Arg Leu Asp
305                 310                 315                 320

Pro Arg Ile His Val Thr Tyr Trp Ser Phe Asp Gly Asp Thr Glu Asp
```

```
                325                 330                 335

Ala Ala Glu Arg Arg Glu Arg Arg Ala Arg Arg Ala Ser Ala Val Asp
            340                 345                 350

Leu Gln Gln Ala Gly Ile Asp Gln Leu Asn Tyr Asn Ser Tyr Tyr Leu
        355                 360                 365

Tyr Glu Val Pro Thr Asp Leu Asp Pro Ala Asp Ser Asp Tyr Thr Val
    370                 375                 380

Ala Asp Leu Arg Glu Asn Trp Ser Leu Arg Ala Trp Asp Gly Asp Ser
385                 390                 395                 400

Gly Ser Leu Leu Ala Ala Pro Met Ser Gly Ala Ala Val Ala Ile Trp
                405                 410                 415

Gly Glu Asp Leu Glu Asp Pro Pro Ser Asp Ala Leu Leu Arg Trp Ser
            420                 425                 430

Ala Pro His Val Thr Ala Met Ile Glu Thr Ala Ala Ser
        435                 440                 445


<210> SEQ ID NO 12
<211> LENGTH: 458
<212> TYPE: PRT
<213> ORGANISM: Curtobacterium oceanosedimentum

<400> SEQUENCE: 12

Ile Gly Gly Ser Ala Gly Thr Ala Asp Ala Ser Gly Ala Pro Arg Leu
1               5                   10                  15

Val Val Thr Lys Val Thr Ala Ser Ser Thr Thr Thr Ser Thr Arg Thr
            20                  25                  30

Thr Val Arg Thr Thr Leu Thr Val Lys Asn Thr Ser Val Ala Arg Lys
        35                  40                  45

Pro Ala Ala Asp Ala Trp Leu Ser Leu Thr Ala Gly Ser Lys Arg Tyr
    50                  55                  60

Thr Leu Gly His Val Ser Val Gln Ser Leu Ala Ala Gly Ala Ser Ala
65                  70                  75                  80

Thr Ile His Ala Thr His Thr Ala Pro Pro Arg Ala Pro Ala Gly Lys
                85                  90                  95

Tyr Ala Val Leu Ala Cys Thr Gly Ala Phe Ser Leu Ser Lys Cys Gly
            100                 105                 110

Thr Ser Ala Thr Thr Val Thr Thr Ala Arg Ala Thr Arg Ala Arg Pro
        115                 120                 125

Asp Thr Gly Val Met Leu Asp Val Ala Arg Ala Tyr Tyr Pro Val Ala
    130                 135                 140

Leu Ile Glu Gln Tyr Ile Ala Leu Leu Ala Asp His Gly Gly Arg Phe
145                 150                 155                 160

Leu His Leu His Leu Thr Asp Asp Gln Asn Val Gly Ile Glu Ser Glu
                165                 170                 175

Val Leu Gly Gln Thr Leu Ala Asn Ala Asp Leu Arg Asp Gly Val Tyr
            180                 185                 190

Thr Ser Arg Ile Thr Gly Arg Pro Phe Leu Ser Ala Ala Gln Ala Arg
        195                 200                 205

Glu Ile Ser Arg Tyr Ala Ala Gln Arg Gly Ile Ala Ile Ile Pro Glu
    210                 215                 220

Ile Asp Thr Pro Gly His Met Ala Ala Ala Phe Ala Leu Leu Glu Ala
225                 230                 235                 240

Gly His Gly Lys Gln Trp Val Asp Arg Ile Arg Ser Gly Glu Ser Glu
                245                 250                 255
```

-continued

```
Leu Asp Thr Ser Ala Pro Gly Ser Ser Ala Leu Ala Ala Arg Leu Leu
            260                 265                 270

Gln Glu Val Thr Arg Thr Phe Pro Ser Ser Arg Thr Val His Ile Gly
        275                 280                 285

Gly Asp Glu Trp Gly Asp Asp Val Thr Ala Asp Glu Arg Val Gln Trp
    290                 295                 300

Leu Asn Thr Met Ala Ala Ala Val Gly Asn Arg Ala Val Trp Ala Trp
305                 310                 315                 320

Asn Asp Gly Ile Asp Arg Ala Ala Ile Gly Arg Leu Asp Pro Arg Ile
                325                 330                 335

His Val Thr Tyr Trp Ser Phe Asp Gly Asp Thr Glu Asp Ala Thr Glu
            340                 345                 350

Arg Arg Glu Arg Arg Glu Arg Arg Ala Gly Ala Asn Asp Leu Tyr Ala
        355                 360                 365

Ala Gly Ile Asp Leu Leu Asn Tyr Asn Ser Tyr Tyr Leu Tyr Glu Val
    370                 375                 380

Pro Thr Asp Leu Asp Ala Ala Asp Ser Glu Tyr Thr Val Ala Asp Leu
385                 390                 395                 400

Arg Glu Asn Trp Ser Leu Arg Thr Trp Asp Gly Asp Ser Gly Ala Arg
                405                 410                 415

Leu Ala Gly Pro Thr Ser Gly Ala Ala Val Ala Ile Trp Gly Glu Asp
            420                 425                 430

Leu Glu Ala Pro Pro Ser Asp Ala Leu Leu Arg Trp Ser Ala Pro His
        435                 440                 445

Val Leu Ala Met Ile Glu Thr Ala Gly Ser
    450                 455


<210> SEQ ID NO 13
<211> LENGTH: 450
<212> TYPE: PRT
<213> ORGANISM: Curtobacterium leaf154

<400> SEQUENCE: 13

Ala Gly Ser Thr Thr Ser Thr Val Thr Val Thr Gln Val Thr Ala Thr
1               5                   10                  15

Thr Thr Ala Ser Ser Thr Gly Thr Ala Val Arg Thr Thr Leu Lys Ile
            20                  25                  30

Lys Asn Thr Ala Ala Val Arg Lys Pro Ala Ser Ser Ala Trp Leu Tyr
        35                  40                  45

Leu Ser Ala Gly Thr Lys Lys Tyr Thr Leu Gly Arg Val Ala Val Lys
    50                  55                  60

Ala Leu Ala Ala Gly Ser Ser Thr Ser Val Thr Ala Val Arg Gly Thr
65                  70                  75                  80

Pro Ser Arg Ala Thr Ala Gly Glu Tyr Ser Val Leu Ala Cys Ala Gly
                85                  90                  95

Ala Tyr Ser Ala Lys Gln Cys Arg Thr Ser Thr Ala Thr Val Thr Thr
            100                 105                 110

Lys Pro Thr Lys Arg Ala Arg Pro Glu Thr Gly Val Met Leu Asp Val
        115                 120                 125

Ala Arg Ala Tyr Tyr Pro Val Ala Leu Ile Lys Arg Tyr Ile Asp Leu
    130                 135                 140

Leu Ala Asp Asp Gly Gly Arg Phe Leu His Leu His Leu Thr Asp Asp
145                 150                 155                 160

Gln Asn Val Gly Ile Glu Ser Thr Val Leu Gly Gln Thr Leu Ala Asn
                165                 170                 175
```

```
Ala Asp Leu Asp Glu Gly Val Tyr Thr Ser Arg Val Thr Arg Arg Pro
            180                 185                 190

Phe Leu Ser Ala Ala Gln Ala Arg Thr Ile Ser Asp Tyr Ala Ala Arg
        195                 200                 205

Arg Gly Val Ala Ile Val Pro Glu Ile Asp Thr Pro Gly His Met Thr
    210                 215                 220

Ala Ala Phe Asp Leu Leu Glu Ala Gln His Gly Thr Lys Trp Val Asp
225                 230                 235                 240

Arg Ile Arg Ser Gly Glu Asn Glu Leu Asp Thr Ser Thr Pro Gly Ser
                245                 250                 255

Leu Ala Leu Ala Lys Lys Leu Tyr Ala Glu Val Gln Arg Thr Phe Pro
            260                 265                 270

Ala Ser Arg Thr Val His Ile Gly Gly Asp Glu Trp Gly Asp Asp Val
        275                 280                 285

Ser Ala Ala Glu Arg Val Ala Trp Met Asn Ala Met Ala Ala Ala Leu
    290                 295                 300

Gly Asn Arg Glu Val Trp Ala Trp Asn Asp Gly Ile Asp Arg Val Ala
305                 310                 315                 320

Val Gly Arg Leu Asp Pro Arg Ile His Val Thr Tyr Trp Ser Phe Asp
                325                 330                 335

Gly Asp Thr Glu Asp Ala Ala Glu Arg Arg Glu Arg Arg Ala Arg Arg
            340                 345                 350

Ala Ser Ala Val Asp Leu Gln Gln Ala Gly Ile Asp Met Leu Asn Tyr
        355                 360                 365

Asn Ser Tyr Tyr Leu Tyr Glu Val Pro Thr Asp Leu Asp Pro Ala Asp
    370                 375                 380

Ser Glu Tyr Thr Val Ala Asp Leu Arg Glu Asn Trp Ser Leu Arg Thr
385                 390                 395                 400

Trp Asp Gly Asp Ser Gly Ser Leu Leu Ala Ala Pro Met Ser Gly Ala
                405                 410                 415

Ala Val Ala Ile Trp Gly Glu Asp Leu Glu Asp Pro Pro Ser Asp Ala
            420                 425                 430

Leu Leu Arg Trp Ser Ala Pro His Val Thr Ala Met Ile Glu Thr Ala
        435                 440                 445

Ala Ser
    450


<210> SEQ ID NO 14
<211> LENGTH: 324
<212> TYPE: PRT
<213> ORGANISM: Terribacillus saccharophilus

<400> SEQUENCE: 14

Gln Asp Gln Glu Lys Gly Ile Thr Ile Asp Ile Ser Arg Lys Tyr Tyr
1               5                   10                  15

Ser Ile Lys Thr Leu Lys Ala Ile Val Asp Glu Ile Ser Ala Asn Gly
            20                  25                  30

Gly Asp Tyr Leu Gln Leu His Phe Ser Asp Asn Glu Ser Tyr Ala Ile
        35                  40                  45

Ala Ser Glu Phe Leu Gly Gln Asn Ser Glu Asn Pro Asn Ser Ala Tyr
    50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
```

```
                85                  90                  95

Trp Leu Asn Ile Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Val
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Ala Lys Thr Ala Lys Ala Ser Asn Tyr Glu Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Asn Gly Ala Gln
    210                 215                 220

Ser Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Pro
        275                 280                 285

Asn Val Lys Gly Ser Ser Leu Val Phe Trp Gly Glu His Ala Asn Asp
    290                 295                 300

Leu Ser Gln Glu Gly Leu Leu Lys Gln Glu Lys Pro Leu Ile Gln Asn
305                 310                 315                 320

Phe Leu Gly Leu


<210> SEQ ID NO 15
<211> LENGTH: 324
<212> TYPE: PRT
<213> ORGANISM: Terribacillus goriensis

<400> SEQUENCE: 15

Gln Asp Gln Glu Lys Gly Ile Thr Ile Asp Ile Ser Arg Lys Tyr Tyr
1               5                   10                  15

Ser Ile Glu Thr Leu Lys Ser Ile Ile Asp Glu Ile Ser Ala Asn Gly
            20                  25                  30

Gly Asp Tyr Leu Gln Leu His Phe Ser Asp Asn Glu Arg Tyr Ala Ile
        35                  40                  45

Ala Ser Glu Phe Leu Gly Gln Asn Gly Glu Asn Pro Asn Ser Thr Tyr
    50                  55                  60

Leu Thr Lys Lys Glu Leu Leu Ser Leu Ile Ala Tyr Ser Asn Asp Arg
65                  70                  75                  80

Asp Ile Met Val Ile Pro Asp Ile Asp Leu Pro Ala His Ser Arg Gly
                85                  90                  95

Trp Leu Asn Ile Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Val
        115                 120                 125

Ala Leu Tyr Thr Ala Asn Gln Leu Leu Asp Glu Val Leu Asp Leu Phe
```

-continued

```
    130                 135                 140

Tyr Gln Pro Lys Phe Ala Gly Lys Gln Arg Ile Val Leu Gly Gly Asp
145                 150                 155                 160

Glu Val Pro Gly Ser Gly Val His Gln Thr Asp Phe Ile Arg Phe Met
                165                 170                 175

Asn Gln Ile Ala Glu Thr Ala Lys Ala Ser Asn Tyr Lys Pro Gln Met
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Asn Gly Ala Gln
    210                 215                 220

Gly Leu Asp Val Gln Asp Phe Glu Glu Asn Gly Leu Ser Val Tyr Asn
225                 230                 235                 240

Tyr Asn Ala Tyr Ser Leu Tyr Phe Leu Pro Ala Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
        275                 280                 285

Asn Val Lys Gly Ser Ser Leu Val Phe Trp Gly Glu His Ala Asn Asp
    290                 295                 300

Leu Ser Gln Glu Gly Leu Leu Lys Gln Glu Lys Pro Leu Ile Gln Asn
305                 310                 315                 320

Phe Leu Gly Leu


<210> SEQ ID NO 16
<211> LENGTH: 324
<212> TYPE: PRT
<213> ORGANISM: Terribacillus saccharophilus

<400> SEQUENCE: 16

Lys Asp Gln Glu Lys Gly Ile Thr Ile Asp Ile Ser Arg Lys Tyr Tyr
1               5                   10                  15

Ser Ile Gly Thr Leu Lys Ala Ile Val Asp Glu Ile Asn Ala Asn Gly
            20                  25                  30

Gly Asp Tyr Leu Gln Leu His Phe Ser Asp Asn Glu Ser Tyr Ala Ile
        35                  40                  45

Ala Ser Glu Phe Leu Gly Gln Asn Ser Glu Asn Pro Asn Ser Thr Tyr
    50                  55                  60

Leu Thr Lys Lys Glu Leu Leu Ser Leu Ile Ala Tyr Ser Asn Asp Arg
65                  70                  75                  80

Asn Ile Met Val Ile Pro Asp Ile Asp Leu Pro Ala His Ser Lys Gly
                85                  90                  95

Trp Leu Asn Val Met Lys Glu Lys Asp Ser Gly Leu Tyr Thr Asp Ile
            100                 105                 110

Val Thr Asp Tyr Ser Glu Asp Thr Leu Asp Tyr His Asn Asn Ala Ala
        115                 120                 125

Ala Leu Tyr Thr Ala Asn Gln Leu Leu Asp Glu Val Leu Asp Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Gly Ala His Gln Thr Asp Phe Ile Arg Phe Met
                165                 170                 175

Asn Gln Ile Asp Glu Thr Ala Lys Ala Ser Asn Tyr Glu Pro Gln Met
```

```
            180                 185                 190

Trp Asn Asp Ser Ile Thr Pro Glu Gly Ile Gln Asn Leu Asp Arg Ser
        195                 200                 205

Phe Ser Ile Leu Tyr Trp Lys Gln Ser Thr Leu Ser Ser Gly Ala Gln
    210                 215                 220

Gly Leu Asp Val Gln Asn Phe Glu Glu Lys Gly Phe Ser Val Tyr Asn
225                 230                 235                 240

Tyr Asn Ala Tyr Ser Leu Tyr Phe Leu Pro Ser Thr Arg Phe Thr Gln
                245                 250                 255

Glu Asp Ile Thr Glu Gln Ile Asp Tyr Met Lys Trp Ala Tyr Ala Tyr
            260                 265                 270

Asn Lys Phe Phe Tyr Ile Ser Asp Tyr Tyr Lys Gln Val Asp Thr Ser
        275                 280                 285

Asn Val Lys Gly Ser Ser Leu Val Phe Trp Gly Glu His Ala Asn Asp
    290                 295                 300

Leu Ser Gln Glu Gly Leu Leu Glu Gln Glu Lys Pro Leu Ile Gln Asn
305                 310                 315                 320

Phe Leu Ser Leu


<210> SEQ ID NO 17
<211> LENGTH: 324
<212> TYPE: PRT
<213> ORGANISM: Terribacillus saccharophilus

<400> SEQUENCE: 17

Gln Asp Gln Glu Lys Gly Ile Thr Ile Asp Ile Ser Arg Lys His Tyr
1               5                   10                  15

Thr Val Glu Thr Leu Lys Ser Leu Val Asp Glu Ile Ser Tyr Asn Gly
            20                  25                  30

Gly Asn Tyr Val Gln Leu His Phe Ser Asp Asn Glu Asn Tyr Ala Ile
        35                  40                  45

Ala Ser Glu Tyr Leu Gly Gln Ser Ser Glu Asn Thr Asn Asn Thr Tyr
    50                  55                  60

Leu Thr Lys Asn Glu Leu Leu Ser Leu Ile Ala Tyr Ser Asn Asp Lys
65                  70                  75                  80

Asp Ile Leu Val Ile Pro Asp Ile Asp Leu Pro Ala His Ser Lys Gly
                85                  90                  95

Trp Leu Glu Leu Ile Lys Lys Lys Asp Val Lys Leu Tyr Asn Asp Ile
            100                 105                 110

Val Thr Asp Tyr Ser Glu Glu Thr Leu Asp Tyr Tyr Asp Asn Arg Val
        115                 120                 125

Ala Leu Asp Thr Val Asn Gln Leu Leu Asp Glu Val Leu Asp Leu Phe
    130                 135                 140

Tyr Gln Pro Lys Phe Glu Gly Lys Gln Arg Ile Val Leu Gly Gly Asp
145                 150                 155                 160

Glu Val Ser Gly Ser Glu Val His Gln Leu Asp Phe Ile Asp Phe Met
                165                 170                 175

Asn Gln Ile Ala Ser Thr Val Lys Glu Ser Lys Tyr Glu Pro Gln Met
            180                 185                 190

Trp Asn Asp Ser Ile Thr Ser Glu Gly Ile Ala Asn Leu Asp Asp Ser
        195                 200                 205

Phe Ser Ile Leu Tyr Trp Gln Gln Ser Thr Leu Ser Ser Gly Glu Glu
    210                 215                 220

Ser Leu Asn Val Glu Asp Phe Glu Asn Trp Gly Phe Ser Val Tyr Asn
```

```
225                 230                 235                 240

Tyr Asn Ala Tyr Ser Leu Tyr Phe Leu Pro Ser Asn Gly Phe Thr Gln
                245                 250                 255

Glu Asp Ile Asn Glu Gln Met Asp Tyr Met Asn Trp Ala Tyr Ala His
            260                 265                 270

Asn Lys Phe Phe Tyr Ile Ser Asp Tyr Tyr His Ala Val Glu Thr Ser
        275                 280                 285

Asn Val Lys Gly Ser Ser Leu Thr Phe Trp Gly Glu His Ala Thr Asp
    290                 295                 300

Leu Ser Gln Lys Lys Leu Leu Lys Gln Glu Leu Pro Leu Ile Arg His
305                 310                 315                 320

Tyr Leu Asn Leu


<210> SEQ ID NO 18
<211> LENGTH: 324
<212> TYPE: PRT
<213> ORGANISM: Terribacillus saccharophilus

<400> SEQUENCE: 18

Lys Asp Gln Glu Lys Gly Ile Ser Ile Asp Ile Ser Arg Lys Tyr Tyr
1               5                   10                  15

Ser Ile Gly Thr Leu Lys Ala Ile Ile Asp Glu Ile Ser Ala Asn Gly
            20                  25                  30

Gly Asp Tyr Leu Gln Leu His Phe Ser Asp Asn Glu Ser Tyr Ala Ile
        35                  40                  45

Ala Ser Asp Tyr Leu Gly Gln Ile Ser Asp Thr Pro Asn Asn Thr Tyr
    50                  55                  60

Leu Thr Lys Asn Asp Leu Leu Ser Leu Ile Ala Tyr Ser Asn Asp Arg
65                  70                  75                  80

Asn Ile Leu Ile Ile Pro Asp Met Asp Leu Pro Ala His Ser Arg Gly
                85                  90                  95

Trp Leu Glu Leu Met Lys Val Lys Asp Arg Glu Leu Tyr Thr Asp Ile
            100                 105                 110

Val Thr Asp Tyr Ser Asn Glu Thr Leu Asp Tyr His Asn Asn Thr Asp
        115                 120                 125

Ala Leu Asn Thr Ala Asn Gln Leu Leu Asn Glu Ile Leu Glu Leu Phe
    130                 135                 140

Tyr Gln Pro Lys Phe Ala Gly Lys Gln Arg Ile Val Leu Gly Gly Asp
145                 150                 155                 160

Glu Val Pro Gly Ser Glu Ile His Gln Leu Asp Phe Ile Arg Phe Ile
                165                 170                 175

Asn Gln Ile Ala Ser Thr Ala Lys Ala Ser Asn Tyr Ala Pro Gln Met
            180                 185                 190

Trp Asn Asp Ser Ile Thr Ala Glu Gly Ile Gln Asn Leu Asp Lys Ser
        195                 200                 205

Phe Ser Ile Leu Tyr Trp Lys Gln Ser Thr Leu Ser Asn Gly Ala Gln
    210                 215                 220

Ser Leu Glu Val Gln Asp Phe Glu Asp Trp Asp Phe Pro Val Tyr Asn
225                 230                 235                 240

Tyr Asn Ala Tyr Ser Leu Tyr Phe Leu Pro Ser Ile Arg Phe Thr Asp
                245                 250                 255

Glu Asp Ile Thr Glu Gln Met Asn Tyr Met Lys Trp Ala Tyr Ala Tyr
            260                 265                 270

Asn Lys Phe Phe Tyr Ile Ser Asp Tyr Tyr Lys Ser Val Asp Ala Ser
```

```
        275                 280                 285

Asn Val Lys Gly Ser Ser Leu Thr Phe Trp Gly Glu His Ala Thr Asp
    290                 295                 300

Leu Ser Gln Glu Glu Leu Leu Glu Gln Glu Leu Pro Leu Ile Lys Lys
305                 310                 315                 320

Phe Leu Ser Leu


<210> SEQ ID NO 19
<211> LENGTH: 331
<212> TYPE: PRT
<213> ORGANISM: Lactobacillus paraplantarum

<400> SEQUENCE: 19

Asn Ser Ser Thr Leu Asn Thr Ser Gln Gly Val Met Leu Asp Leu Gly
1               5                   10                  15

Arg His Pro Leu Asp Glu Thr Ala Ile Lys Ala Val Ile Ser Ala Ala
            20                  25                  30

Ala Glu Gln His Met Gln Tyr Val Glu Leu His Leu Ser Asp Asn Glu
        35                  40                  45

His Leu Cys Phe Gln Ser Ala Tyr Leu Gly Asn Ala Ala Ser Ala Thr
    50                  55                  60

Val Leu Ser Ala Thr Thr Leu Glu Gln Leu Val Ala Tyr Ala Asn Gln
65                  70                  75                  80

Leu Asn Ile Glu Leu Val Pro Asp Val Asp Leu Pro Ser His Ala Gly
                85                  90                  95

Ala Ile Leu Arg Gln Leu Gln Gln Thr His Pro Asp Ile Tyr Asn Thr
            100                 105                 110

Val Lys Leu Asp Asp Glu Thr Ile Asp Tyr Thr Lys Pro Ala Ala Ile
        115                 120                 125

Ser Leu Ala Thr Thr Leu Tyr Gly Glu Leu Asp Ala Ser Phe Asn Asn
    130                 135                 140

Gln Ser Gln His Asp Leu Met Leu Gly Ala Asp Glu Val Pro Gly Ser
145                 150                 155                 160

Ala Ser Ala Tyr Ile Glu Leu Thr Thr Phe Ile Asn Gln Val Ser Arg
                165                 170                 175

Phe Gln Asn Gln His Gly Phe Asn Thr Ser Ile Trp Asn Asp Ser Leu
            180                 185                 190

Leu Lys Asn Glu Leu Thr Arg Leu Asp Ser Asn Ile Thr Ile Asn Tyr
        195                 200                 205

Trp Ser Gln Ser Gly Asn Asn Thr Asp Val Ala Ile Ile Ala Asp Arg
    210                 215                 220

Tyr Ala Asn Arg Val Ser Val Pro Asp Ile Leu Ala Ser Gly His Pro
225                 230                 235                 240

Ile Val Asn Cys Asn Ser Tyr Ala Thr Tyr Tyr Gln Ile Lys Asn Ile
                245                 250                 255

Gly Asn Val Asn Asp Asp Asp Tyr Phe Ile Asn Tyr Leu Asn His Thr
            260                 265                 270

Phe Arg Pro Asn Ile Phe Asn Glu Ile Asp Thr Asn Gly His Asn Gln
        275                 280                 285

Asp Trp Thr Ile Glu Asp Gly Val Thr Thr Asn Gly Ile Leu Val Ser
    290                 295                 300

Leu Trp Gly Ala Asp Ser Glu His Val Thr Pro Thr Ala Ile Val Asn
305                 310                 315                 320

Phe Ile Lys Arg Met Thr Ile Pro Arg Ser Phe
```

325 330

<210> SEQ ID NO 20
<211> LENGTH: 353
<212> TYPE: PRT
<213> ORGANISM: Lactobacillus apinorum

<400> SEQUENCE: 20

Thr Leu Ala Asp Thr Ser Asn Asp Thr Lys Arg Ile Gly Leu Ser Leu
1 5 10 15

Asp Cys Ser Arg Thr Tyr Tyr Ser Pro Ser Thr Ile Lys Lys Tyr Ile
20 25 30

Asp Leu Leu Lys Lys Asp His Gly Thr Tyr Leu Gln Leu His Leu Asn
35 40 45

Asp Asn Glu Arg Tyr Gly Val Glu Ser Ser Thr Leu Gly Gln Thr Thr
50 55 60

Gln Asn Ala Thr Leu Lys Asp Gly Val Tyr Tyr Asn Asn Lys Thr His
65 70 75 80

Leu Ala Phe Leu Ser Lys Asn Gln Leu Leu Asp Val Ile Gln Tyr Gly
85 90 95

Tyr Thr His Gly Ile Glu Val Ile Pro Glu Ile Asp Leu Pro Gly His
100 105 110

Ala Gln Ser Ile Phe Lys Leu Leu Ser Tyr Thr Ser Glu Gly Lys Lys
115 120 125

Leu Val Lys Glu Leu Glu Asn Lys Asp Gly Tyr Asn Glu Met Tyr Tyr
130 135 140

Asn Lys Gln Ala Thr Ile Asp Phe Ser Lys Lys Leu Leu Ser Glu Tyr
145 150 155 160

Val Gly Met Leu Pro Ser Gly Tyr His Ile Ile Val Gly Ala Asp Glu
165 170 175

Ile Thr Ile Ser Asp Lys Ser Asp Gln Glu Ala Val Val Lys Tyr Ile
180 185 190

Asn Ala Ile Asp Asp Tyr Val Asn Ala Asn His Leu Lys Leu Glu Met
195 200 205

Trp Asn Asp Ser Phe His Lys Ala Val Leu Ser Lys Tyr His Lys Asp
210 215 220

Ile Leu Ile Asn Tyr Trp Ser Leu Thr Gly Glu Val Ser Ser Ser Lys
225 230 235 240

Asp Arg Lys Asp Asn Ile Arg Met Arg Ala Thr Leu Pro Glu Leu Asn
245 250 255

Lys Ala Gly Phe Lys Thr Ile Asn Tyr Asn Ser Tyr Tyr Leu Tyr Met
260 265 270

Ile Thr Asp Pro Thr Ser Phe Thr Asn Glu Ser Lys Lys Ile Trp Thr
275 280 285

Ser Glu Phe Lys Lys Trp Lys Met Asn Met Trp Asn Asp Glu Ser Thr
290 295 300

Lys Asp Ile Thr Lys Ser Ala Asn Asn Ile Gly Ala Ala Ile Ser Ile
305 310 315 320

Trp Gly Glu Tyr Pro Asn Gln Tyr Thr Gly Asp Gln Thr Tyr Asn Lys
325 330 335

Thr Tyr Tyr Tyr Val Asp Thr Phe Leu Lys Ala Gln Asp Lys Phe Thr
340 345 350

Lys

-continued

<210> SEQ ID NO 21
<211> LENGTH: 331
<212> TYPE: PRT
<213> ORGANISM: Lactobacillus paraplantarum

<400> SEQUENCE: 21

```
Asn Ser Ser Thr Leu Asn Thr Ser Gln Gly Val Met Leu Asp Leu Gly
1               5                   10                  15

Arg His Pro Leu Asp Glu Thr Ala Ile Lys Ala Val Ile Ser Ala Ala
            20                  25                  30

Ala Glu Gln His Met Gln Tyr Val Glu Leu His Leu Ser Asp Asn Glu
        35                  40                  45

His Leu Cys Phe Gln Ser Ala Tyr Leu Gly Asn Ala Ala Ser Ala Thr
    50                  55                  60

Val Leu Ser Ala Thr Thr Leu Glu Gln Leu Val Ala Tyr Ala Asn Gln
65                  70                  75                  80

Leu Asn Ile Glu Leu Val Pro Asp Val Asp Leu Pro Ser His Ala Gly
                85                  90                  95

Ala Ile Leu Arg Gln Leu Gln Gln Thr His Pro Asp Ile Tyr Asn Thr
            100                 105                 110

Val Lys Leu Asp Asp Glu Thr Ile Asp Tyr Thr Lys Pro Ala Ala Val
        115                 120                 125

Ser Leu Ala Thr Thr Leu Tyr Gly Glu Leu Asp Ala Ser Phe Asn Asn
    130                 135                 140

Gln Ser Gln His Asp Leu Met Leu Gly Ala Asp Glu Val Ser Gly Ser
145                 150                 155                 160

Ala Ser Ala Tyr Ile Glu Leu Thr Thr Phe Ile Asn Gln Val Ser Arg
                165                 170                 175

Phe Gln Asn Gln Asn Gly Phe Asn Thr Ser Ile Trp Asn Asp Ser Leu
            180                 185                 190

Leu Lys Asn Glu Leu Asn Arg Leu Asp Ser Asn Ile Thr Ile Asn Tyr
        195                 200                 205

Trp Ser Gln Ser Gly Asn Asn Thr Asp Ala Ala Ile Ile Ala Asp Arg
    210                 215                 220

Tyr Ala Asn Arg Ala Ser Val Pro Asp Ile Leu Ala Ser Gly His Pro
225                 230                 235                 240

Ile Val Asn Cys Asn Ser Tyr Ala Thr Tyr Tyr Gln Phe Lys Asn Ile
                245                 250                 255

Gly Asn Val Asn Asp Asp Asn Tyr Phe Ile Asn Tyr Leu Asn His Thr
            260                 265                 270

Phe Arg Pro Asn Ile Phe Asn Glu Ile Asp Thr Asn Gly His Asn Gln
        275                 280                 285

Asp Trp Thr Ile Glu Asp Gly Val Thr Thr Asn Gly Ile Leu Val Ser
    290                 295                 300

Leu Trp Gly Ala Asp Ser Glu His Val Thr Pro Thr Ala Ile Val Asn
305                 310                 315                 320

Phe Ile Lys Arg Met Ala Ile Pro Arg Ser Phe
                325                 330
```

<210> SEQ ID NO 22
<211> LENGTH: 323
<212> TYPE: PRT
<213> ORGANISM: Staphylococcus cohnii

<400> SEQUENCE: 22

```
Gln Asp Phe Gln Lys Gly Ile Asn Val Asp Ile Ala Arg Lys Asp Tyr
```

```
1               5                   10                  15

Ser Leu Lys Ser Leu Lys Lys Ile Val Asp Thr Ile His Glu Asn Asn
            20                  25                  30

Gly Asp Tyr Leu Gln Leu His Phe Ser Asp Asn Glu Asn Tyr Ala Ile
        35                  40                  45

Glu Ser Gln Phe Phe Lys His Glu Asn Ile Ala Ser Gln Asn Tyr Leu
    50                  55                  60

Ser Gln Gln Glu Leu Lys Asn Leu Ile His Tyr Ser Asn Lys Leu Asn
65                  70                  75                  80

Ile Met Val Val Pro Glu Phe Asp Leu Pro Ser His Ser Lys Ala Trp
                85                  90                  95

Leu Leu Leu Leu Lys Asn Glu Asn Ser Asn Leu His Glu Asn Ile Val
            100                 105                 110

Ser Asp Tyr Ser Asp Glu Thr Ile Asp Phe Phe Ser Asn Gln Lys Ala
        115                 120                 125

Leu Glu Ile Ser Lys Arg Gln Ile Lys Glu Ile Leu Asn Leu Phe His
    130                 135                 140

Gln Pro Asn Phe Gln Lys Glu Gln Arg Ile Val Leu Gly Gly Asp Glu
145                 150                 155                 160

Val Pro Gly Gly Lys Ser Tyr Gln Asn Asp Phe Ile Asn Phe Met Asn
                165                 170                 175

Glu Ile Gly Glu Tyr Ala Tyr Gln Asn Gly Tyr Glu Pro Gln Ile Trp
            180                 185                 190

Asn Asp Ser Ile Thr Lys Asn Gly Leu Lys Leu Leu Lys Asn Tyr Phe
        195                 200                 205

Ser Val Ile Phe Trp Lys Gln Ser Asn Asn Glu Asn Asn Glu Pro Gly
    210                 215                 220

Ile Thr Val Glu Asp Phe Leu Asp Tyr Asn Phe Lys Val Tyr Asn Tyr
225                 230                 235                 240

Asn Phe Tyr Ser Leu Tyr Phe Leu Pro Ser Lys Asn Tyr Ser Pro Thr
                245                 250                 255

Asp Ile Glu Glu Gln Thr Ser Tyr Ile Ser Trp Ala Tyr Asn His Asn
            260                 265                 270

Ser Phe Tyr Tyr Leu Lys Asn Pro Tyr Tyr Glu Val Asp Ser Leu Asn
        275                 280                 285

Ile Gln Gly Ser Ala Leu Ser Phe Trp Gly Glu His Ala Thr Gly Met
    290                 295                 300

Arg Glu Glu Glu Val Leu Asn Gln Glu Leu Pro Leu Ile Arg Thr Tyr
305                 310                 315                 320

Leu Asn Lys


<210> SEQ ID NO 23
<211> LENGTH: 321
<212> TYPE: PRT
<213> ORGANISM: Staphylococcus fleurettii

<400> SEQUENCE: 23

Glu Ser Ile Gln Glu Gly Val Ser Val Asp Ile Ala Arg Lys Glu Tyr
1               5                   10                  15

Ser Leu Glu Ser Leu Lys Gln Ile Val Asp Thr Ile His Glu Asn Asn
            20                  25                  30

Gly Gln Tyr Leu Gln Leu His Phe Ser Asp Asp Glu Asn Tyr Ala Ile
        35                  40                  45

Glu Ser Asp Tyr Phe Ser His Gln Gly Ile Pro Asn Glu Asn Tyr Leu
```

```
    50                  55                  60

Thr Lys Ala Glu Ile Lys Ser Leu Ile Ala Tyr Ser Asn Glu Leu Asn
65                  70                  75                  80

Val Met Val Val Pro Asp Ile Asp Phe Pro Ser His Ser Lys Ala Leu
                85                  90                  95

Leu Ser Leu Ile Lys Asn Glu Asp Lys Asp Leu Tyr Asn Gln Ile Ile
            100                 105                 110

Ser Asp Tyr Ser Asp Asn Thr Phe Asp Phe Phe Ser Asn Asp Lys Ala
        115                 120                 125

Leu Ala Ile Ser Lys Arg His Ile Gly Glu Ile Thr Thr Leu Phe Asn
    130                 135                 140

Gln Pro Lys Tyr Asn Gly Gln Gln Arg Ile Val Leu Gly Gly Asp Glu
145                 150                 155                 160

Val Pro Gly Gly Gly Ala Tyr Gln Ser Asp Phe Ile Ser Tyr Met Asn
                165                 170                 175

Asn Ile Gly Ser Tyr Ala Ala Gly Gln Gly Tyr Glu Pro Gln Met Trp
            180                 185                 190

Asn Asp Met Ile Ser His Glu Gly Ile Lys Ser Leu Asn Asp Thr Phe
        195                 200                 205

Ser Ile Leu Tyr Trp Lys Gln Asn Glu Asn Ser Lys Ser Asp Leu Thr
    210                 215                 220

Val Glu Asp Phe Ala Glu Tyr Asp Phe Lys Ile Tyr Asn Tyr Asn Phe
225                 230                 235                 240

Tyr Ser Leu Tyr Phe Leu Pro Ser Asn Gln Phe Thr Asn Ala Asp Ile
                245                 250                 255

Glu Glu Gln Ala Asp Tyr Ile Ser Trp Ala Tyr Ala Tyr Asn Lys Phe
            260                 265                 270

Phe Tyr Thr Asn Glu Pro Tyr Gln Glu Val Asp Ser Asp Asn Val Lys
        275                 280                 285

Gly Ser Ala Leu Ser Phe Trp Gly Glu Asp Ala Leu Asn Met Ser Gln
    290                 295                 300

Thr Glu Leu Ile Asn Gln Glu Ile Pro Leu Ile Lys Ala Tyr Phe Ser
305                 310                 315                 320

Ser


<210> SEQ ID NO 24
<211> LENGTH: 269
<212> TYPE: PRT
<213> ORGANISM: Bacillus lentus

<400> SEQUENCE: 24

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
```

```
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 25
<211> LENGTH: 275
<212> TYPE: PRT
<213> ORGANISM: Bacillus amyloliquefaciens

<400> SEQUENCE: 25

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205
```

```
Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275


<210> SEQ ID NO 26
<211> LENGTH: 311
<212> TYPE: PRT
<213> ORGANISM: Bacillus sp.

<400> SEQUENCE: 26

Ala Val Pro Ser Thr Gln Thr Pro Trp Gly Ile Lys Ser Ile Tyr Asn
1               5                   10                  15

Asp Gln Ser Ile Thr Lys Thr Thr Gly Gly Ser Gly Ile Lys Val Ala
            20                  25                  30

Val Leu Asp Thr Gly Val Tyr Thr Ser His Leu Asp Leu Ala Gly Ser
        35                  40                  45

Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ala Ile Arg His Val Ala Asp Glu Ala
        115                 120                 125

Ser Arg Thr Gly Ser Lys Val Val Ile Asn Met Ser Leu Gly Ser Ser
    130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Ser Gly Ser Gly Ser Asn
                165                 170                 175

Thr Ile Gly Phe Pro Gly Gly Leu Val Asn Ala Val Ala Val Ala Ala
            180                 185                 190

Leu Glu Asn Val Gln Gln Asn Gly Thr Tyr Arg Val Ala Asp Phe Ser
        195                 200                 205

Ser Arg Gly Asn Pro Ala Thr Ala Gly Asp Tyr Ile Ile Gln Glu Arg
    210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
        275                 280                 285

Ile Lys Gly Gly Ile Gly Ala Gly Thr Gly Asp Asp Tyr Ala Ser Gly
    290                 295                 300
```

```
Phe Gly Tyr Pro Arg Val Lys
305                 310


<210> SEQ ID NO 27
<211> LENGTH: 269
<212> TYPE: PRT
<213> ORGANISM: Bacillus lentus

<400> SEQUENCE: 27

Ala Gln Ser Val Pro Trp Gly Ile Glu Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Arg Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asp Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Leu Ser Thr Trp Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Asp Thr Trp Glu
                245                 250                 255

Tyr Gly Ser Gly Leu Val Asn Ala Glu Ala Ala Thr Arg
            260                 265


<210> SEQ ID NO 28
<211> LENGTH: 311
<212> TYPE: PRT
<213> ORGANISM: Bacillus sp.

<400> SEQUENCE: 28

Ala Val Pro Ser Thr Gln Thr Pro Trp Gly Ile Lys Ser Ile Tyr Asn
1               5                   10                  15

Asp Gln Ser Ile Thr Lys Thr Thr Gly Gly Lys Gly Ile Lys Val Ala
            20                  25                  30

Val Leu Asp Thr Gly Val Tyr Thr Ser His Leu Asp Leu Ala Gly Ser
        35                  40                  45
```

```
Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Lys Gly Glu Gly
            100                 105                 110

Tyr Ser Asp Asp Ile Ala Ala Ala Ile Arg His Val Ala Asp Glu Ala
        115                 120                 125

Ser Arg Thr Gly Ser Lys Val Val Ile Asn Met Ser Leu Gly Ser Ser
    130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Glu Gly Pro Lys Pro Asn
                165                 170                 175

Thr Ile Gly Tyr Pro Ala Gly Phe Val Asn Ala Val Ala Val Ala Ala
            180                 185                 190

Leu Glu Asn Val Gln Glu Lys Gly Thr Tyr Arg Val Ala Asp Phe Ser
        195                 200                 205

Ser Arg Gly Asn Pro Ala Thr Ala Gly Asp Tyr Ile Ile Gln Glu Arg
    210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
        275                 280                 285

Ile Lys Gly Gly Ile Gly Ala Gly Pro Gly Asp Asp Tyr Ala Ser Gly
    290                 295                 300

Phe Gly Tyr Pro Arg Val Lys
305                 310


<210> SEQ ID NO 29
<211> LENGTH: 269
<212> TYPE: PRT
<213> ORGANISM: Bacillus lentus

<400> SEQUENCE: 29

Ala Gln Thr Ile Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Glu Gly Ala Ile Ser Ser Ile Ala Gln Gly Leu Glu Trp Ala
```

```
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Ile Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 30
<211> LENGTH: 269
<212> TYPE: PRT
<213> ORGANISM: Bacillus lentus

<400> SEQUENCE: 30

Ala Gln Ser Val Pro Trp Gly Ile Ser Arg Val Gln Ala Pro Ala Ala
1               5                   10                  15

His Asn Arg Gly Leu Ala Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asp Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Gly Gly Ala Ile Ser Ser Ile Ala Gln Gly Leu Glu Trp Ala
            100                 105                 110

Gly Leu Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Asp Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Asp Phe Ser Gln Tyr Gly Ala Gly Leu Asp Ile
            180                 185                 190

Val Ala Pro Gly Val Asn Val Gln Ser Thr Tyr Pro Gly Ser Ala Tyr
        195                 200                 205
```

-continued

```
Ala Ser Leu Asn Gly Thr Ser Met Ala Thr Pro His Val Ala Gly Ala
    210                 215                 220

Ala Val Leu Val Lys Gln Lys Asn Pro Ser Trp Ser Asn Val Arg Ile
225                 230                 235                 240

Arg Asp His Leu Lys Asn Thr Ala Thr Ser Leu Gly Ser Thr Asn Leu
                245                 250                 255

Tyr Gly Ser Gly Leu Val Asn Ala Phe Ala Ala Thr Arg
            260                 265


<210> SEQ ID NO 31
<211> LENGTH: 269
<212> TYPE: PRT
<213> ORGANISM: Bacillus lentus

<400> SEQUENCE: 31

Ala Gln Ser Val Pro Trp Gly Ile Ser Arg Val Gln Ala Pro Ala Ala
1               5                   10                  15

His Asn Arg Gly Leu Arg Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Gly Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Val Leu Val Lys Gln Lys Asn Pro Ser Trp Ser Asn Val Arg Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```